US012807972B2

(12) United States Patent
Doudna et al.

(10) Patent No.: US 12,807,972 B2
(45) Date of Patent: Nov. 24, 2026

(54) COMPOSITIONS AND METHODS FOR INCREASING HOMOLOGY-DIRECTED REPAIR

(71) Applicant: The Regents of the University of California, Oakland, CA (US)

(72) Inventors: Jennifer A. Doudna, Berkeley, CA (US); Enrique Lin-Shiao, Berkeley, CA (US); Rachel Lew, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 834 days.

(21) Appl. No.: 18/014,700

(22) PCT Filed: Jul. 7, 2021

(86) PCT No.: PCT/US2021/040652

§ 371 (c)(1),
(2) Date: Jan. 5, 2023

(87) PCT Pub. No.: WO2022/010991

PCT Pub. Date: Jan. 13, 2022

(65) Prior Publication Data

US 2023/0323404 A1 Oct. 12, 2023

Related U.S. Application Data

(60) Provisional application No. 63/049,316, filed on Jul. 8, 2020.

(51) Int. Cl.

| | |
|---|---|
| ***C12N 15/11*** | (2006.01) |
| ***C12N 9/22*** | (2006.01) |
| ***C12N 15/10*** | (2006.01) |
| ***C12N 15/90*** | (2006.01) |

(52) U.S. Cl.

CPC ............. *C12N 15/907* (2013.01); *C12N 9/22* (2013.01); *C12N 15/1082* (2013.01); *C12N 15/11* (2013.01); *C12N 2310/20* (2017.05); *C12N 2800/80* (2013.01)

(58) Field of Classification Search

CPC .... C12N 15/907; C12N 9/22; C12N 15/1082; C12N 15/11; C12N 2310/20; C12N 15/90

See application file for complete search history.

(56) References Cited

U.S. PATENT DOCUMENTS

2013/0224859 A1 8/2013 Bachelet et al.
2015/0218204 A1 8/2015 Yin et al.
2018/0127787 A1 5/2018 Gurumurthy et al.
2019/0003973 A1 1/2019 Lin et al.
2019/0156911 A1 5/2019 Veneziano et al.
2019/0240340 A1 8/2019 Fleming et al.

FOREIGN PATENT DOCUMENTS

WO WO2020051507 A1 * 3/2020

OTHER PUBLICATIONS

Balakrishnan, et al.; Delivering DNA origami to cells; Nanomedicine; vol. 14, No. 7, pp. 911-925 (Mar. 22, 2019).
Castro, et al.; "A primer to scaffolded DNA origami"; Nature Methods; vol. 8, No. 3, pp. 221-229 (Mar. 2011).
Dietz, et al.; "Folding DNA into Twisted and Curved Nanoscale Shapes"; Science; vol. 325, No. 5941, 11 pages (Aug. 7, 2009).
Endo, et al.; "DNA Origami Nanomachines"; Molecules; vol. 23, No. 1766, 14 pages (Jul. 18, 2018).
Lin-Shiao, et al.; "CRISPR-Cas9-mediated nuclear transport and genomic integration of nanostructured genes in human primary cells"; Nucleic Acids Research; vol. 50, No. 3, pp. 1256-1268 (Feb. 22, 2022).
Jiao, et al.; "Programming Switchable Transcription of Topologically Constrained DNA"; Journal of the American Chemical Society; vol. 142, No. 24, pp. 10739-10746 (2020).
Li, et al.; "A DNA nanorobot functions as a cancer therapeutic in response to a molecular trigger in vivo"; Nature Biotechnology; vol. 36, pp. 258-264 (2018).
Li, et al.; "Smart Drug Delivery Nanocarriers with Self-Assembled DNA Nanostructures"; Advanced Materials; vol. 25, No. 32, pp. 4386-4396 (Aug. 27, 2013).
Madhanagopal, et al.; "DNA Nanocarriers: Programmed to Deliver"; Trends in Biochemical Sciences; vol. 43, No. 12, pp. 997-1013 (Dec. 2018).
Wang, et al.; "A Tubular DNA Nanodevice as a siRNA/Chemo-Drug Co-delivery Vehicle for Combined Cancer Therapy"; Angewandte Chemie International Edition; vol. 60, No. 5, pp. 2594-2598 (Feb. 1, 2021).
Zhang, et al.; "DNA nanostructures coordinate gene silencing in mature plants"; PNAS; vol. 116, No. 15, pp. 7543-7548 (2019).
Zhao, et al.; "Efficient Intracellular Delivery of RNase A Using DNA Origami Carriers"; ACS Applied Materials & Interfaces; vol. 11, No. 12, pp. 11112-11118 (2019).

* cited by examiner

*Primary Examiner* — J. E. Angell
(74) *Attorney, Agent, or Firm* — Kyle A. Gurley; Bozicevic, Field & Francis LLP

(57) ABSTRACT

The present disclosure provides compositions comprising a gene-editing polypeptide, a single-stranded donor DNA, and one or more staple oligonucleotides. The present disclosure provides compositions comprising a DNA nanostructure and a gene-editing polypeptide. The present disclosure provides gene editing methods using the compositions. The present disclosure provides methods of using the compositions to produce a genetically modified cell. The present disclosure provides kits useful for carrying out gene editing.

19 Claims, 39 Drawing Sheets

Specification includes a Sequence Listing.

Figure 1: Comparison of DNA templates for homology-directed repair.

Figure 2: DNA origami creates highly compact repair templates.

FIG. 3A

*Streptococcus pyogenes* Cas9

MDKKYSIGLDIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDHIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD
(SEQ ID NO:4)

FIG. 3B

SpCas9 (SpCas9 D10A)
MDKKYSIGL<u>A</u>IGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPWNFEEVVDKGASAQSFIERMTNFD
KNLPNEKVLPKHSLLYEYFTVYNELTKVKYVTEGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQE
LDINRLSDYDVDHIVPQSFLKDDSIDNKVLTRSDKNRGKSDNVPSEEVVKKMKNYWRQLLNAKLITQRKFDNLTKAERGGL
SELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGD
(SEQ ID NO:5)

FIG. 3C

SpCas9 (H840A)
MDKKYSIGLDIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDAIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD
(SEQ ID NO:6)

FIG. 3D

SpCas9 (D10A; H840A)

MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDAIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD
(SEQ ID NO:7)

FIG. 3E enSpCas9 (nCas9 with K848A/K1003A/R1060A mutations

MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPWNFEEVVDKGASAQSFIERMTNFD
KNLPNEKVLPKHSLLYEYFTVYNELTKVKYVTEGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQE
LDINRLSDYDVDHIVPQSFLADDSIDNKVLTRSDKNRGKSDNVPSEEVVKKMKNYWRQLLNAKLITQRKFDNLTKAERGGL
SELDKAGFIKRQLVETRQITKHVAQILDSRMNTKYDENDKLIREVKVITLKSKLVSDFRKDFQFYKVREINNYHHAHDAYLN
AVVGTALIKKYPALESEFVYGDYKVYDVRKMIAKSEQEIGKATAKYFFYSNIMNFFKTEITLANGEIRKAPLIETNGETGEIV
WDKGRDFATVRKVLSMPQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGD
(SEQ ID NO:8)

FIG. 3F nSpCas9-HF1

DKKYSIGLAIGTNSVGWAVITDEYKVPSKKFKVLGNTDRHSIKKNLIGALLFDSGETAEATRLKRTARRRYTRRKNRICYLQE
IFSNEMAKVDDSFFHRLEESFLVEEDKKHERHPIFGNIVDEVAYHEKYPTIYHLRKKLVDSTDKADLRLIYLALAHMIKFRGH
FLIEGDLNPDNSDVDKLFIQLVQTYNQLFEENPINASGVDAKAILSARLSKSRRLENLIAQLPGEKKNGLFGNLIALSLGLTPNF
KSNFDLAEDAKLQLSKDTYDDDLDNLLAQIGDQYADLFLAAKNLSDAILLSDILRVNTEITKAPLSASMIKRYDEHHQDLTLL
KALVRQQLPEKYKEIFFDQSKNGYAGYIDGGASQEEFYKFIKPILEKMDGTEELLVKLNREDLLRKQRTFDNGSIPHQIHLGE
LHAILRRQEDFYPFLKDNREKIEKILTFRIPYYVGPLARGNSRFAWMTRKSEETITPWNFEEVVDKGASAQSFIERMTAFDKN
LPNEKVLPKHSLLYEYFTVYNELTKVKYVTEGMRKPAFLSGEQKKAIVDLLFKTNRKVTVKQLKEDYFKKIECFDSVEISGV
EDRFNASLGTYHDLLKIIKDKDFLDNEENEDILEDIVLTLTLFEDREMIEERLKTYAHLFDDKVMKQLKRRRYTGWGALSRK
LINGIRDKQSGKTILDFLKSDGFANRNFMALIHDDSLTFKEDIQKAQVSGQGDSLHEHIANLAGSPAIKKGILQTVKVVDELV
KVMGRHKPENIVIEMARENQTTQKGQKNSRERMKRIEEGIKELGSQILKEHPVENTQLQNEKLYLYYLQNGRDMYVDQELD
INRLSDYDVDHIVPQSFLKDDSIDNKVLTRSDKNRGKSDNVPSEEVVKKMKNYWRQLLNAKLITQRKFDNLTKAERGGLSE
LDKAGFIKRQLVETRAITKHVAQILDSRMNTKYDENDKLIREVKVITLKSKLVSDFRKDFQFYKVREINNYHHAHDAYLNAV
VGTALIKKYPKLESEFVYGDYKVYDVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKYGGFDSPTVAYSVLVVAKVEKGKSKK
LKSVKELLGITIMERSSFEKNPIDFLEAKGYKEVKKDLIIKLPKYSLFELENGRKRMLASAGELQKGNELALPSKYVNFLYLAS
HYEKLKGSPEDNEQKQLFVEQHKHYLDEIIEQISEFSKRVILADANLDKVLSAYNKHRDKPIREQAENIIHLFTLTNLGAPAAF
KYFDTTIDRKRYTSTKEVLDATLIHQSITGLYETRIDLSQLGGD (SEQ ID NO:9)

FIG. 3G

*Staphylococcus aureus* Cas9

MKRNYILGLDIGITSVGYGIIDYETRDVIDAGVRLFKEANVENNEGRRSKRGARRLKRRRRHRIQRVKKLLFDYNLLTDHSEL
SGINPYEARVKGLSQKLSEEEFSAALLHLAKRRGVHNVNEVEEDTGNELSTKEQISRNSKALEEKYVAELQLERLKKDGEV
RGSINRFKTSDYVKEAKQLLKVQKAYHQLDQSFIDTYIDLLETRRTYYEGPGEGSPFGWKDIKEWYEMLMGHCTYFPEELR
SVKYAYNADLYNALNDLNNLVITRDENEKLEYYEKFQIIENVFKQKKKPTLKQIAKEILVNEEDIKGYRVTSTGKPEFTNLKVY
HDIKDITARKEIIENAELLDQIAKILTIYQSSEDIQEELTNLNSELTQEEIEQISNLKGYTGTHNLSLKAINLILDELWHTNDNQIAI
FNRLKLVPKKVDLSQQKEIPTTLVDDFILSPVVKRSFIQSIKVINAIIKKYGLPNDIIIELAREKNSKDAQKMINEMQKRNRQTN
ERIEEIIRTTGKENAKYLIEKIKLHDMQEGKCLYSLEAIPLEDLLNNPFNYEVDHIIPRSVSFDNSFNNKVLVKQEENSKKGNR
TPFQYLSSSDSKISYETFKKHILNLAKGKGRISKTKKEYLLEERDINRFSVQKDFINRNLVDTRYATRGLMNLLRSYFRVNNL
DVKVKSINGGFTSFLRRKWKFKKERNKGYKHHAEDALIIANADFIFKEWKKLDKAKKVMENQMFEEKQAESMPEIETEQEY
KEIFITPHQIKHIKDFKDYKYSHRVDKKPNRELINDTLYSTRKDDKGNTLIVNNLNGLYDKDNDKLKKLINKSPEKLLMYHHDP
QTYQKLKLIMEQYGDEKNPLYKYYEETGNYLTKYSKKDNGPVIKKIKYYGNKLNAHLDITDDYPNSRNKVVKLSLKPYRFDV
YLDNGVYKFVTVKNLDVIKKENYYEVNSKCYEEAKKLKKISNQAEFIASFYNNDLIKINGELYRVIGVNNDLLNRIEVNMIDITY
REYLENMNDKRPPRIIKTIASKTQSIKKYSTDILGNLYEVKSKKHPQIIKKG
(SEQ ID NO:10)

FIG. 3H

*Francisella tularensis* Cpf1 (Cas12a)

```
   1 MSIYQEFVNK YSLSKTLRFE LIPQGKTLEN IKARGLILDD EKRAKDYKKA KQIIDKYHQF
  61 FIEEILSSVC ISEDLLQNYS DVYFKLKKSD DDNLQKDFKS AKDTIKKQIS EYIKDSEKFK
 121 NLFNQNLIDA KKGQESDLIL WLKQSKDNGI ELFKANSDIT DIDEALEIIK SFKGWTTYFK
 181 GFHENRKNVY SSNDIPTSII YRIVDDNLPK FLENKAKYES LKDKAPEAIN YEQIKKDLAE
 241 ELTFDIDYKT SEVNQRVFSL DEVFEIANFN NYLNQSGITK FNTIIGGKFV NGENTKRKGI
 301 NEYINLYSQQ INDKTLKKYK MSVLFKQILS DTESKSFVID KLEDDSDVVT TMQSFYEQIA
 361 AFKTVEEKSI KETLSLLFDD LKAQKLDLSK IYFKNDKSLT DLSQQVFDDY SVIGTAVLEY
 421 ITQQIAPKNL DNPSKKEQEL IAKKTEKAKY LSLETIKLAL EEFNKHRDID KQCRFEEILA
 481 NFAAIPMIFD EIAQNKDNLA QISIKYQNQG KKDLLQASAE DDVKAIKDLL DQTNNLLHKL
 541 KIFHISQSED KANILDKDEH FYLVFEECYF ELANIVPLYN KIRNYITQKP YSDEKFKLNF
 601 ENSTLANGWD KNKEPDNTAI LFIKDDKYYL GVMNKKNNKI FDDKAIKENK GEGYKKIVYK
 661 LLPGANKMLP KVFFSAKSIK FYNPSEDILR IRNHSTHTKN GSPQKGYEKF EFNIEDCRKF
 721 IDFYKQSISK HPEWKDFGFR FSDTQRYNSI DEFYREVENQ GYKLTFENIS ESYIDSVVNQ
 781 GKLYLFQIYN KDFSAYSKGR PNLHTLYWKA LFDERNLQDV VYKLNGEAEL FYRKQSIPKK
 841 ITHPAKEAIA NKNKDNPKKE SVFEYDLIKD KRFTEDKFFF HCPITINFKS SGANKFNDEI
 901 NLLLKEKAND VHILSIDRGE RHLAYYTLVD GKGNIIKQDT FNIIGNDRMK TNYHDKLAAI
 961 EKDRDSARKD WKKINNIKEM KEGYLSQVVH EIAKLVIEYN AIVVFEDLNF GFKRGRFKVE
1021 KQVYQKLEKM LIEKLNYLVF KDNEFDKTGG VLRAYQLTAP FETFKKMGKQ TGIIYYVPAG
1081 FTSKICPVTG FVNQLYPKYE SVSKSQEFFS KFDKICYNLD KGYFEFSFDY KNFGDKAAKG
1141 KWTIASFGSR LINFRNSDKN HNWDTREVYP TKELEKLLKD YSIEYGHGEC IKAAICGESD
1201 KKFFAKLTSV LNTILQMRNS KTGTELDYLI SPVADVNGNF FDSRQAPKNM PQDADANGAY
1261 HIGLKGLMLL GRIKNNQEGK KLNLVIKNEE YFEFVQNRNN
(SEQ ID NO:11)
```

FIG. 3I

*Acidaminococcus sp. BV3L6* type V CRISPR-associated protein Cpf1 (Cas12a)

TQFEGFTNLYQVSKTLRFELIPQGKTLKHIQEQGFIEEDKARNDHYKELKPIIDRIYKTYADQCLQLVQLDWENLSAAIDSYR
KEKTEETRNALIEEQATYRNAIHDYFIGRTDNLTDAINKRHAEIYKGLFKAELFNGKVLKQLGTVTTTEHENALLRSFDKFTT
YFSGFYENRKNVFSAEDISTAIPHRIVQDNFPKFKENCHIFTRLITAVPSLREHFENVKKAIGIFVSTSIEEVFSFPFYNQLLTQTQ
IDLYNQLLGGISREAGTEKIKGLNEVLNLAIQKNDETAHIIASLPHRFIPLFKQILSDRNTLSFILEEFKSDEEVIQSFCKYKTLLR
NENVLETAEALFNELNSIDLTHIFISHKKLETISSALCDHWDTLRNALYERRISELTGKITKSAKEKVQRSLKHEDINLQEIISAA
GKELSEAFKQKTSEILSHAHAALDQPLPTTLKKQEEKEILKSQLDSLLGLYHLLDWFAVDESNEVDPEFSARLTGIKLEMEPSL
SFYNKARNYATKKPYSVEKFKLNFQMPTLASGWDVNKEKNNGAILFVKNGLYYLGIMPKQKGRYKALSFEPTEKTSEGFD
KMYYDYFPDAAKMIPKCSTQLKAVTAHFQTHTTPILLSNNFIEPLEITKEIYDLNNPEKEPKKFQTAYAKKTGDQKGYREALC
KWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLS
DEARALLPNVITKEVSHEIIKDRRFTSDKFFFHVPITLNYQAANSPSKFNQRVNAYLKEHPETPIIGIDRGERNLIYITVIDSTGKI
LEQRSLNTIQQFDYQKKLDNREKERVAARQAWSVVGTIKDLKQGYLSQVIHEIVDLMIHYQAVVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIK
NHESRKHFLEGFDFLHYDVKTGDFILHFKMNRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMRNSNAATGEDYINSPVRDLNGVCFDSRFQN
PEWPMDADANGAYHIALKGQLLLNHLKESKDLKLQNGISNQDWLAYIQELRN
(SEQ ID NO:12)

FIG. 3J

Cpf1 (AsCpf1 R1225A)
TQFEGFTNLYQVSKTLRFELIPQGKTLKHIQEQGFIEEDKARNDHYKELKPIIDRIYKTYADQCLQLVQLDWENLSAAIDSYR
KEKTEETRNALIEEQATYRNAIHDYFIGRTDNLTDAINKRHAEIYKGLFKAELFNGKVLKQLGTVTTTEHENALLRSFDKFTT
YFSGFYENRKNVFSAEDISTAIPHRIVQDNFPKFKENCHIFTRLITAVPSLREHFENVKKAIGIFVSTSIEEVFSFPFYNQLLTQTQ
IDLYNQLLGGISREAGTEKIKGLNEVLNLAIQKNDETAHIIASLPHRFIPLFKQILSDRNTLSFILEEFKSDEEVIQSFCKYKTLLR
NENVLETAEALFNELNSIDLTHIFISHKKLETISSALCDHWDTLRNALYERRISELTGKITKSAKEKVQRSLKHEDINLQEIISAA
GKELSEAFKQKTSEILSHAHAALDQPLPTTLKKQEEKEILKSQLDSLLGLYHLLDWFAVDESNEVDPEFSARLTGIKLEMEPSL
SFYNKARNYATKKPYSVEKFKLNFQMPTLASGWDVNKEKNNGAILFVKNGLYYLGIMPKQKGRYKALSFEPTEKTSEGFD
KMYYDYFPDAAKMIPKCSTQLKAVTAHFQTHTTPILLSNNFIEPLEITKEIYDLNNPEKEPKKFQTAYAKKTGDQKGYREALC
KWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLS
DEARALLPNVITKEVSHEIIKDRRFTSDKFFFHVPITLNYQAANSPSKFNQRVNAYLKEHPETPIIGIDRGERNLIYITVIDSTGKI
LEQRSLNTIQQFDYQKKLDNREKERVAARQAWSVVGTIKDLKQGYLSQVIHEIVDLMIHYQAVVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIK
NHESRKHFLEGFDFLHYDVKTGDFILHFKMNRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMANSNAATGEDYINSPVRDLNGVCFDSRFQN
PEWPMDADANGAYHIALKGQLLLNHLKESKDLKLQNGISNQDWLAYIQELRN (SEQ ID NO:13)

FIG. 3K

> Listeria seeligeri (WP_012985477.1)
MWISIKTLIHHLGVLFFCDYMYNRREKKIIEVKTMRITKVEVDRKKVLISRDKNGGKLVY
ENEMQDNTEQIMHHKKSSFYKSVVNKTICRPEQKQMKKLVHGLLQENSQEKIKVSDVTKL
NISNFLNHRFKKSLYYFPENSPDKSEEYRIEINLSQLLEDSLKKQQGTFICWESFSKDME
LYINWAENYISSKTKLIKKSIRNNRIQSTESRSGQLMDRYMKDILNKNKPFDIQSVSEKY
QLEKLTSALKATFKEAKKNDKEINYKLKSTLQNHERQIIEELKENSELNQFNIEIRKHLE
TYFPIKKTNRKVGDIRNLEIGEIQKIVNHRLKNKIVQRILQEGKLASYEIESTVNSNSLQ
KIKIEEAFALKFINACLFASNNLRNMVYPVCKKDILMIGEFKNSFKEIKHKKFIRQWSQF
FSQEITVDDIELASWGLRGAIAPIRNEIIHLKKHSWKKFFNNPTFKVKKSKIINGKTKDV
TSEFLYKETLFKDYFYSELDSVPELIINKMESSKILDYYSSDQLNQVFTIPNFELSLLTS
AVPFAPSFKRVYLKGFDYQNQDEAQPDYNLKLNIYNEKAFNSEAFQAQYSLFKMVYYQVF
LPQFTTNNDLFKSSVDFILTLNKERKGYAKAFQDIRKMNKDEKPSEYMSYIQSQLMLYQK
KQEEKEKINHFEKFINQVFIKGFNSFIEKNRLTYICHPTKNTVPENDNIEIPFHTDMDDS
NIAFWLMCKLLDAKQLSELRNEMIKFSCSLQSTEEISTFTKAREVIGLALLNGEKGCNDW
KELFDDKEAWKKNMSLYVSEELLQSLPYTQEDGQTPVINRSIDLVKKYGTETILEKLFSS
SDDYKVSAKDIAKLHEYDVTEKIAQQESLHKQWIEKPGLARDSAWTKKYQNVINDISNYQ
WAKTKVELTQVRHLHQLTIDLLSRLAGYMSIADRDFQFSSNYILERENSEYRVTSWILLS
ENKNKNKYNDYELYNLKNASIKVSSKNDPQLKVDLKQLRLTLEYLELFDNRLKEKRNNIS
HFNYLNGQLGNSILELFDDARDVLSYDRKLKNAVSKSLKEILSSHGMEVTFKPLYQTNHH
LKIDKLQPKKIHHLGEKSTVSSNQVSNEYCQLVRTLLTMK (SEQ ID NO:14)

FIG. 3L

>Leptotrichia buccalis (WP_015770004.1)
MKVTKVGGISHKKYTSEGRLVKSESEENRTDERLSALLNMRLDMYIKNPSSTETKENQKR
IGKLKKFFSNKMVYLKDNTLSLKNGKKENIDREYSETDILESDVRDKKNFAVLKKIYLNE
NVNSEELEVFRNDIKKKLNKINSLKYSFEKNKANYQKINENNIEKVEGKSKRNIIYDYYR
ESAKRDAYVSNVKEAFDKLYKEEDIAKLVLEIENLTKLEKYKIREFYHEIIGRKNDKENF
AKIIYEEIQNVNNMKELIEKVPDMSELKKSQVFYKYYLDKEELNDKNIKYAFCHFVEIEM
SQLLKNYVYKRLSNISNDKIKRIFEYQNLKKLIENKLLNKLDTYVRNCGKYNYYLQDGEI
ATSDFIARNRQNEAFLRNIIGVSSVAYFSLRNILETENENDITGRMRGKTVKNNKGEEKY
VSGEVDKIYNENKKNEVKENLKMFYSYDFNMDNKNEIEDFFANIDEAISSIRHGIVHFNL
ELEGKDIFAFKNIAPSEISKKMFQNEINEKKLKLKIFRQLNSANVFRYLEKYKILNYLKR
TRFEFVNKNIPFVPSFTKLYSRIDDLKNSLGIYWKTPKTNDDNKTKEIIDAQIYLLKNIY
YGEFLNYFMSNNGNFFEISKEIIELNKNDKRNLKTGFYKLQKFEDIQEKIPKEYLANIQS
LYMINAGNQDEEEKDTYIDFIQKIFLKGFMTYLANNGRLSLIYIGSDEETNTSLAEKKQE
FDKFLKKYEQNNNIKIPYEINEFLREIKLGNILKYTERLNMFYLILKLLNHKELTNLKGS
LEKYQSANKEEAFSDQLELINLLNLDNNRVTEDFELEADEIGKFLDFNGNKVKDNKELKK
FDTNKIYFDGENIIKHRAFYNIKKYGMLNLLEKIADKAGYKISIEELKKYSNKKNEIEKN
HKMQENLHRKYARPRKDEKFTDEDYESYKQAIENIEEYTHLKNKVEFNELNLLQGLLLRI
LHRLVGYTSIWERDLRFRLKGEFPENQYIEEIFNFENKKNVKYKGGQIVEKYIKFYKELH
QNDEVKINKYSSANIKVLKQEKKDLYIRNYIAHFNYIPHAEISLLEVLENLRKLLSYDRK
LKNAVMKSVVDILKEYGFVATFKIGADKKIGIQTLESEKIVHLKNLKKKKLMTDRNSEEL
CKLVKIMFEYKMEEKKSEN (SEQ ID NO:15)

FIG. 3M

> Leptotrichia shahii (WP_018451595.1)
MGNLFGHKRWYEVRDKKDFKIKRKVKVKRNYDGNKYILNINENNNKEKIDNNKFIRKYIN
YKKNDNILKEFTRKFHAGNILFKLKGKEGIIRIENNDDFLETEEVVLYIEAYGKSEKLKA
LGITKKKIIDEAIRQGITKDDKKIEIKRQENEEEIEIDIRDEYTNKTLNDCSIILRIIEN
DELETKKSIYEIFKNINMSLYKIIEKIIENETEKVFENRYYEEHLREKLLKDDKIDVILT
NFMEIREKIKSNLEILGFVKFYLNVGGDKKKSKNKKMLVEKILNINVDLTVEDIADFVIK
ELEFWNITKRIEKVKKVNNEFLEKRRNRTYIKSYVLLDKHEKFKIERENKKDKIVKFFVE
NIKNNSIKEKIEKILAEFKIDELIKKLEKELKKGNCDTEIFGIFKKHYKVNFDSKKFSKK
SDEEKELYKIIYRYLKGRIEKILVNEQKVRLKKMEKIEIEKILNESILSEKILKRVKQYT
LEHIMYLGKLRHNDIDMTTVNTDDFSRLHAKEELDLELITFFASTNMELNKIFSRENINN
DENIDFFGGDREKNYVLDKKILNSKIKIIRDLDFIDNKNNITNNFIRKFTKIGTNERNRI
LHAISKERDLQGTQDDYNKVINIIQNLKISDEEVSKALNLDVVFKDKKNIITKINDIKIS
EENNNDIKYLPSFSKVLPEILNLYRNNPKNEPFDTIETEKIVLNALIYVNKELYKKLILE
DDLEENESKNIFLQELKKTLGNIDEIDENIIENYYKNAQISASKGNNKAIKKYQKKVIEC
YIGYLRKNYEELFDFSDFKMNIQEIKKQIKDINDNKTYERITVKTSDKTIVINDDFEYII
SIFALLNSNAVINKIRNRFFATSVWLNTSEYQNIIDILDEIMQLNTLRNECITENWNLNL
EEFIQKMKEIEKDFDDFKIQTKKEIFNNYYEDIKNNILTEFKDDINGCDVLEKKLEKIVI
FDDETKFEIDKKSNILQDEQRKLSNINKKDLKKKVDQYIKDKDQEIKSKILCRIIFNSDF
LKKYKKEIDNLIEDMESENENKFQEIYYPKERKNELYIYKKNLFLNIGNPNFDKIYGLIS
NDIKMADAKFLFNIDGKNIRKNKISEIDAILKNLNDKLNGYSKEYKEKYIKKLKENDDFF
AKNIQNKNYKSFEKDYNRVSEYKKIRDLVEFNYLNKIESYLIDINWKLAIQMARFERDMH
YIVNGLRELGIIKLSGYNTGISRAYPKRNGSDGFYTTTAYYKFFDEESYKKFEKICYGFG
IDLSENSEINKPENESIRNYISHFYIVRNPFADYSIAEQIDRVSNLLSYSTRYNNSTYAS
VFEVFKKDVNLDYDELKKKFKLIGNNDILERLMKPKKVSVLELESYNSDYIKNLIIELLT
KIENTNDTL (SEQ ID NO:16)

FIG. 3N

> Rhodobacter capsulatus (R121) (ETD76934.1) ( U717_11515)
MQIGKVQGRTISEFGDPAGGLKRKISTDGKNRKELPAHLSSDPKALIGQWISGIDKIYRK
PDSRKSDGKAIHSPTPSKMQFDARDDLGEAFWKLVSEAGLAQDSDYDQFKRRLHPYGDKF
QPADSGAKLKFEADPPEPQAFHGRWYGAMSKRGNDAKELAAALYEHLHVDEKRIDGQPKR
NPKTDKFAPGLVVARALGIESSVLPRGMARLARNWGEEEIQTYFVVDVAASVKEVAKAAV
SAAQAFDPPRQVSGRSLSPKVGFALAEHLERVTGSKRCSFDPAAGPSVLALHDEVKKTYK
RLCARGKNAARAFPADKTELLALMRHTHENRVRNQMVRMGRVSEYRGQQAGDLAQSHYWT
SAGQTEIKESEIFVRLWVGAFALAGRSMKAWIDPMGKIVNTEKNDRDLTAAVNIRQVISN
KEMVAEAMARRGIYFGETPELDRLGAEGNEGFVFALLRYLRGCRNQTFHLGARAGFLKEI
RKELEKTRWGKAKEAEHVVLTDKTVAAIRAIIDNDAKALGARLLADLSGAFVAHYASKEH
FSTLYSEIVKAVKDAPEVSSGLPRLKLLLKRADGVRGYVHGLRDTRKHAFATKLPPPPAP
RELDDPATKARYIALLRLYDGPFRAYASGITGTALAGPAARAKEAATALAQSVNVTKAYS
DVMEGRSSRLRPPNDGETLREYLSALTGETATEFRVQIGYESDSENARKQAEFIENYRRD
MLAFMFEDYIRAKGFDWILKIEPGATAMTRAPVLPEPIDTRGQYEHWQAALYLVMHFVPA
SDVSNLLHQLRKWEALQGKYELVQDGDATDQADARREALDLVKRFRDVLVLFLKTGEARF
EGRAAPFDLKPFRALFANPATFDRLFMATPTTARPAEDDPEGDGASEPELRVARTLRGLR
QIARYNHMAVLSDLFAKHKVRDEEVARLAEIEDETQEKSQIVAAQELRTDLHDKVMKCHP
KTISPEERQSYAAAIKTIEEHRFLVGRVYLGDHLRLHRLMMDVIGRLIDYAGAYERDTGT
FLINASKQLGAGADWAVTIAGAANTDARTQTRKDLAHFNVLDRADGTPDLTALVNRAREM
MAYDRKRKNAVPRSILDMLARLGLTLKWQMKDHLLQDATITQAAIKHLDKVRLTVGGPAA
VTEARFSQDYLQMVAAVFNGSVQNPKPRRRDDGDAWHKPPKPATAQSQPDQKPPNKAPSA
GSRLPPPQVGEVYEGVVVKVIDTGSLGFLAVEGVAGNIGLHISRLRRIREDAIIVGRRYR
FRVEIYVPPKSNTSKLNAADLVRID (SEQ ID NO:17)

FIG. 3O

```
>WP_034560163.1 WP_034560163.1 hypothetical protein [Carnobacterium gallinarum]
MRITKVKIKLDNKLYQVTMQKEEKYGTLKLNEESRKSTAEILRLKKASFNKSFHSKTINS
QKENKNATIKKNGDYISQIFEKLVGVDTNKNIRKPKMSLTDLKDLPKKDLALFIKRKFKN
DDIVEIKNLDLISLFYNALQKVPGEHFTDESWADFCQEMMPYREYKNKFIERKIILLANS
IEQNKGFSINPETFSKRKRVLHQWAIEVQERGDFSILDEKLSKLAEIYNFKKMCKRVQDE
LNDLEKSMKKGKNPEKEKEAYKKQKNFKIKTIWKDYPYKTHIGLIEKIKENEELNQFNIE
IGKYFEHYFPIKKERCTEDEPYYLNSETIATTVNYQLKNALISYLMQIGKYKQFGLENQV
LDSKKLQEIGIYEGFQTKFMDACVFATSSLKNIIEPMRSGDILGKREFKEAIATSSFVNY
HHFFPYFPFELKGMKDRESELIPFGEQTEAKQMQNIWALRGSVQQIRNEIFHSFDKNQKF
NLPQLDKSNFEFDASENSTGKSQSYIETDYKFLFEAEKNQLEQFFIERIKSSGALEYYPL
KSLEKLFAKKEMKFSLGSQVVAFAPSYKKLVKKGHSYQTATEGTANYLGLSYYNRYELKE
ESFQAQYYLLKLIYQYVFLPNFSQGNSPAFRETVKAILRINKDEARKKMKKNKKFLRKYA
FEQVREMEFKETPDQYMSYLQSEMREEKVRKAEKNDKGFEKNITMNFEKLLMQIFVKGFD
VFLTTFAGKELLLSSEEKVIKETEISLSKKINEREKTLKASIQVEHQLVATNSAISYWLF
CKLLDSRHLNELRNEMIKFKQSRIKFNHTQHAELIQNLLPIVELTILSNDYDEKNDSQNV
DVSAYFEDKSLYETAPYVQTDDRTRVSFRPILKLEKYHTKSLIEALLKDNPQFRVAATDI
QEWMHKREEIGELVEKRKNLHTEWAEGQQTLGAEKREEYRDYCKKIDRFNWKANKVTLTY
LSQLHYLITDLLGRMVGFSALFERDLVYFSRSFSELGGETYHISDYKNLSGVLRLNAEVK
PIKIKNIKVIDNEENPYKGNEPEVKPFLDRLHAYLENVIGIKAVHGKIRNQTAHLSVLQL
ELSMIESMNNLRDLMAYDRKLKNAVTKSMIKILDKHGMILKLKIDENHKNFEIESLIPKE
IIHLKDKAIKTNQVSEEYCQLVLALLTTNPGNQLN  (SEQ ID NO:18)
```

FIG. 3P

>CRZ35554.1 Herbinix hemicellulosilytica genome assembly TUM3/55, contig 02_T3/55T_contig26, whole genome shotgun sequence MKLTRRRISGNSVDQKITAAFYRDMSQGLLYYDSEDNDCTDKVIESMDFERSWRGRILKN
GEDDKNPFYMFVKGLVGSNDKIVCEPIDVDSDPDNLDILINKNLTGFGRNLKAPDSNDTL
ENLIRKIQAGIPEEEVLPELKKIKEMIQKDIVNRKEQLLKSIKNNRIPFSLEGSKLVPST
KKMKWLFKLIDVPNKTFNEKMLEKYWEIYDYDKLKANITNRLDKTDKKARSISRAVSEEL
REYHKNLRTNYNRFVSGDRPAAGLDNGGSAKYNPDKEEFLLFLKEVEQYFKKYFPVKSKH
SNKSKDKSLVDKYKNYCSYKVVKKEVNRSIINQLVAGLIQQGKLLYYFYYNDTWQEDFLN
SYGLSYIQVEEAFKKSVMTSLSWGINRLTSFFIDDSNTVKFDDITTKKAKEAIESNYFNK
LRTCSRMQDHFKEKLAFFYPVYVKDKKDRPDDDIENLIVLVKNAIESVSYLRNRTFHFKE
SSLLELLKELDDKNSGQNKIDYSVAAEFIKRDIENLYDVFREQIRSLGIAEYYKADMISD
CFKTCGLEFALYSPKNSLMPAFKNVYKRGANLNKAYIRDKGPKETGDQGQNSYKALEEYR
ELTWYIEVKNNDQSYNAYKNLLQLIYYHAFLPEVRENEALITDFINRTKEWNRKETEERL
NTKNNKKHKNFDENDDITVNTYRYESIPDYQGESLDDYLKVLQRKQMARAKEVNEKEEGN
NNYIQFIRDVVVWAFGAYLENKLKNYKNELQPPLSKENIGLNDTLKELFPEEKVKSPFNI
KCRFSISTFIDNKGKSTDNTSAEAVKTDGKEDEKDKKNIKRKDLLCFYLFLRLLDENEIC
KLQHQFIKYRCSLKERRFPGNRTKLEKETELLAELEELMELVRFTMPSIPEISAKAESGY
DTMIKKYFKDFIEKKVFKNPKTSNLYYHSDSKTPVTRKYMALLMRSAPLHLYKDIFKGYY
LITKKECLEYIKLSNIIKDYQNSLNELHEQLERIKLKSEKQNGKDSLYLDKKDFYKVKEY
VENLEQVARYKHLQHKINFESLYRIFRIHVDIAARMVGYTQDWERDMHFLFKALVYNGVL
EERRFEAIFNNNDDNNDGRIVKKIQNNLNNKNRELVSMLCWNKKLNKNEFGAIIWKRNPI
AHLNHFTQTEQNSKSSLESLINSLRILLAYDRKRQNAVTKTINDLLLNDYHIRIKWEGRV
DEGQIYFNIKEKEDIENEPIIHLKHLHKKDCYIYKNSYMFDKQKEWICNGIKEEVYDKSI
LKCIGNLFKFDYEDKNKSSANPKHT (SEQ ID NO:19)

FIG. 4

BFP-mEGFP construct

HOMOLOGYARMSNggctccggtgcccgtcagtgggcagagcgcacatcgcccacagtccccgagaagttggggggaggggtc
ggcaattgaaccggtgcctagagaaggtggcgcggggtaaactgggaaagtgatgtcgtgtactggctccgcctttttcccgagggtggg
ggagaaccgtatataagtgcagtagtcgccgtgaacgttctttttcgcaacgggtttgccgccagaacacaggtaagtgccgtgtgtggtt
cccgcgggcctggcctctttacgggttatggcccttgcgtgccttgaattacttccacctggctgcagtacgtgattcttgatcccgagcttc
gggttggaagtgggtgggagagttcgaggccttgcgcttaaggagccccttcgcctcgtgcttgagttgaggcctggcctgggcgctggg
gccgccgcgtgcgaatctggtggcaccttcgcgcctgtctcgctgctttcgataagtctctagccatttaaaatttttgatgacctgctgcga
cgctttttttctggcaagatagtcttgtaaatgcgggccaagatctgcacactggtatttcggtttttggggccgcgggcggcgacggggcc
cgtgcgtcccagcgcacatgttcggcgaggcggggcctgcgagcgcggccaccgagaatcggacgggggtagtctcaagctggccggc
ctgctctggtgcctggcctcgcgccgccgtgtatcgccccgccctgggcggcaaggctggcccggtcggcaccagttgcgtgagcggaaa
gatggccgcttcccggccctgctgcagggagctcaaaatggaggacgcggcgctcgggagagcgggcgggtgagtcacccacacaaag
gaaaagggcctttccgtcctcagccgtcgcttcatgtgactccacggagtaccgggcgccgtccaggcacctcgattagttctcgagctttt
ggagtacgtcgtctttaggttggggggaggggttttatgcgatggagtttccccacactgagtgggtggagactgaagttaggccagcttg
gcacttgatgtaattctccttggaatttgcccttttttgagtttggatcttggttcattctcaagcctcagacagtggttcaaagtttttttcttcc
atttcaggtgtcgtgaggaattagcttggtactaatacgactcactatagggagacccaagctggctaggtaagcttggtaccgagctcg
gatccggtaccgccacc*atggtgagcaagggcgaggagctgttcaccggggtggtgcccatcctggtcgagctggacggcgacgt*
*aaacggccacaagttcagcgtgtccggcgagggcgagggcgatgccacctacggcaagctgaccctgaagttcatctgcaccacc*
*ggcaagctgccggtgccctggcccaccctcgtgaccaccctgacccatggcgtgcagtgcttcagccgctaccccgaccacatgaag*
*cagcacgacttcttcaagtccgccatgcccgaaggctacgtccaggagcgcaccatcttcttcaaggacgacggcaactacaagac*
*ccgcgccgaggtgaagttcgagggcgacaccctggtgaaccgcatcgagctgaagggcatcgacttcaaggaggacggcaacat*
*cctggggcacaagctggagtacaactacaacagccacaacgtctatatcatggccgacaagcagaagaacggcatcaaggtga*
*acttcaagatccgccacaacatcgaggacggcagcgtgcagctcgccgaccactaccagcagaacacccccatcggcgacggccc*
*cgtgctgctgcccgacaaccactacctgagcacccagtccaagctgagcaaagaccccaacgagaagcgcgatcacatggtcctg*
*ctggagttcgtgaccgccgccgggatcactctcggcatggacgagctgtacaagtaa*ctcgagatatctagacccagctttcttgtac
aaagtggttgatatccagcacagtggcggccgctcgacaatcaacctctggattacaaaatttgtgaaagattgactggtattcttaac
tatgttgctccttttacgctatgtggatacgctgctttaatgcctttgtatcatgctattgcttcccgtatggctttcattttctcctccttgtat
aaatcctggttgctgtctctttatgaggagttgtggcccgttgtcaggcaacgtggcgtggtgtgcactgtgtttgctgacgcaacccccca
ctggttggggcattgccaccacctgtcagctcctttccgggactttcgctttccccctccctattgccacggcggaactcatcgccgcctgc
cttgcccgctgctggacaggggctcggctgttgggcactgacaattccgtggtgttgtcggggaagctgacgtcctttccatggctgctcg
cctgtgttgccacctggattctgcgcgggacgtccttctgctacgtcccttcggccctcaatccagcggaccttccttcccgcggcctgctg
ccggctctgcggcctcttccgcgtcttcgccttcgccctcagacgagtcggatctccctttgggccgcctccccgcctggacctgcaggatt
ctgcagatatccgHOMOLOGYARMSZ- (SEQ ID NO:20)

EF-1alpha promoter + T7 promoter -- underlined
BFP to mEGFP construct – italics
WPRE – bold

FIG. 5 dCas9-3xFlag-NLS

HOMOLOGYARMSNTTAATGACGGCTCGTTTCTTTTCTGTGGCTGCGTGAAAGCCTTAAAGGGCTCCGG
GAGGGCCCTTTGTGCGGGGGGGAGCGGCTCGGGGGGTGCGTGCGTGTGTGTGTGCGTGGGGAGCGCC
GCGTGCGGCCCGCGCTGCCCGGCGGCTGTGAGCGCTGCGGGCGCGGCGCGGGGCTTTGTGCGCTCCGC
GTGTGCGCGAGGGGAGCGCGGCCGGGGGCGGTGCCCCGCGGTGCGGGGGGGCTGCGAGGGGAACAA
AGGCTGCGTGCGGGGTGTGTGCGTGGGGGGGTGAGCAGGGGGTGTGGGCGCGGCGGTCGGGCTGTA
ACCCCCCCCTGCACCCCCCTCCCCGAGTTGCTGAGCACGGCCCGGCTTCGGGTGCGGGGCTCCGTGCGG
GGCGTGGCGCGGGGCTCGCCGTGCCGGGCGGGGGGTGGCGGCAGGTGGGGGTGCCGGGCGGGGCG
GGGCCGCCTCGGGCCGGGGAGGGCTCGGGGGAGGGGCGCGGCGGCCCCGGAGCGCCGGCGGCTGTC
GAGGCGCGGCGAGCCGCAGCCATTGCCTTTTATGGTAATCGTGCGAGAGGGCGCAGGGACTTCCTTTGT
CCCAAATCTGGCGGAGCCGAAATCTGGGAGGCGCCGCCGCACCCCCTCTAGCGGGCGCGGGCGAAGCG
GTGCGGCGCCGGCAGGAAGGAAATGGGCGGGGAGGGCCTTCGTGCGTCGCCGCGCCGCCGTCCCCTTC
TCCATCTCCAGCCTCGGGGCTGCCGCAGGGGGACGGCTGCCTTCGGGGGGGACGGGGCAGGGCGGGG
TTCGGCTTCTGGCGTGTGACCGGCGGCTCTAGAGCCTCTGCTAACCATGTTCATGCCTTCTTCTTTTTCCT
ACAGCTCCTGGGCAACGTGCTGGTTGTTGTGCTGTCTCATCATTTTGGCAAAGAATTCgccaccatggacaag
aagtacagcatcggcctggccatcggcaccaactctgtgggctgggccgtgatcaccgacgagtacaaggtgcccagcaagaaattcaa
ggtgctgggcaacaccgaccggcacagcatcaagaagaacctgatcggcgccctgctgttcgacagcggagaaacagccgaggccac
ccggctgaagagaaccgccagaagaagatacaccagacggaagaaccggatctgctatctgcaagagatcttcagcaacgagatggc
caaggtggacgacagcttcttccacagactggaagagtccttcctggtggaagaggataagaagcacgagcggcaccccatcttcggca
acatcgtggacgaggtggcctaccacgagaagtaccccaccatctaccacctgagaaagaaactggtggacagcaccgacaaggccg
acctgcggctgatctatctggccctggcccacatgatcaagttccggggccacttcctgatcgagggcgacctgaaccccgacaacagcg
acgtggacaagctgttcatccagctggtgcagacctacaaccagctgttcgaggaaaaccccatcaacgccagcggcgtggacgccaag
gccatcctgtctgccagactgagcaagagcagacggctggaaaatctgatcgcccagctgcccggcgagaagaagaatggcctgttcgg
caacctgattgccctgagcctgggcctgacccccaacttcaagagcaacttcgacctggccgaggatgccaaactgcagctgagcaagg
acacctacgacgacgacctggacaacctgctggcccagatcggcgaccagtacgccgacctgtttctggccgccaagaacctgtccgac
gccatcctgctgagcgacatcctgagagtgaacaccgagatcaccaaggcccccctgagcgcctctatgatcaagagatacgacgagca
ccaccaggacctgaccctgctgaaagctctcgtgcggcagcagctgcctgagaagtacaaagagattttcttcgaccagagcaagaacg
gctacgccggctacatcgatggcggagccagccaggaagagttctacaagttcatcaagcccatcctggaaaagatggacggcaccga
ggaactgctcgtgaagctgaacagagaggacctgctgcggaagcagcggaccttcgacaacggcagcatcccccaccagatccacctg
ggagagctgcacgccattctgcggcggcaggaagatttttacccattcctgaaggacaaccgggaaaagatcgagaagatcctgacctt
ccgcatcccctactacgtgggccctctggccaggggaaacagcagattcgcctggatgaccagaaagagcgaggaaaccatcacccct
ggaacttcgaggaagtggtggacaagggcgccagcgcccagagcttcatcgagcggatgaccaacttcgataagaacctgcccaacga
gaaggtgctgcccaagcacagcctgctgtacgagtacttcaccgtgtacaacgagctgaccaaagtgaaatacgtgaccgagggaatg
agaaagcccgccttcctgagcggcgagcagaaaaaagccatcgtggacctgctgttcaagaccaaccggaaagtgaccgtgaagcagc
tgaaagaggactacttcaagaaaatcgagtgcttcgactccgtggaaatctccggcgtggaagatcggttcaacgcctccctgggcacat
accacgatctgctgaaaattatcaaggacaaggacttcctggacaatgaggaaaacgaggacattctggaagatatcgtgctgaccctg
acactgtttgaggacagagagatgatcgaggaacggctgaaaacctatgcccacctgttcgacgacaaagtgatgaagcagctgaagc
ggcggagatacaccggctggggcaggctgagccggaagctgatcaacggcatccgggacaagcagtccggcaagacaatcctggattt
cctgaagtccgacggcttcgccaacagaaacttcatgcagctgatccacgacgacagcctgacctttaaagaggacatccagaaagccc
aggtgtccggccagggcgatagcctgcacgagcacattgccaatctggccggcagccccgccattaagaagggcatcctgcagacagtg
aaggtggtggacgagctcgtgaaagtgatgggccggcacaagcccgagaacatcgtgatcgaaatggccagagagaaccagaccacc

FIG. 5 (continued)

cagaagggacagaagaacagccgcgagagaatgaagcggatcgaagagggcatcaaagagctgggcagccagatcctgaaagaac
accccgtggaaaacacccagctgcagaacgagaagctgtacctgtactacctgcagaatgggcgggatatgtacgtggaccaggaact
ggacatcaaccggctgtccgactacgatgtggacgctatcgtgcctcagagctttctgaaggacgactccatcgataacaaagtgctgac
tcggagcgacaagaaccggggcaagagcgacaacgtgccctccgaagaggtcgtgaagaagatgaagaactactggcgccagctgct
gaatgccaagctgattacccagaggaagttcgacaatctgaccaaggccgagagaggcggcctgagcgaactggataaggccggcttc
atcaagagacagctggtggaaacccggcagatcacaaagcacgtggcacagatcctggactcccggatgaacactaagtacgacgag
aacgacaaactgatccgggaagtgaaagtgatcaccctgaagtccaagctggtgtccgatttccggaaggatttccagttttacaaagtg
cgcgagatcaacaactaccaccacgcccacgacgcctacctgaacgccgtcgtgggaaccgccctgatcaaaaagtaccctaagctgg
aaagcgagttcgtgtacggcgactacaaggtgtacgacgtgcggaagatgatcgccaagagcgagcaggaaatcggcaaggctaccg
ccaagtacttcttctacagcaacatcatgaactttttcaagaccgagattaccctggccaacggcgagatccggaagcggcctctgatcg
agacaaacggcgaaacaggcgagatcgtgtgggataagggccgggactttgccaccgtgcggaaagtgctgtctatgccccaagtgaa
tatcgtgaaaaagaccgaggtgcagacaggcggcttcagcaaagagtctatcctgcccaagaggaacagcgacaagctgatcgccaga
aagaaggactgggaccctaagaagtacggcggcttcgacagccccaccgtggcctattctgtgctggtggtggccaaagtggaaaagg
gcaagtccaagaaactgaagagtgtgaaagagctgctggggatcaccatcatggaaagaagcagcttcgagaagaatcccatcgactt
tctggaagccaagggctacaaagaagtgaaaaaggacctgatcatcaagctgcctaagtactccctgttcgagctggaaaacggccgg
aagagaatgctggcctctgccggcgaactgcagaagggaaacgaactggccctgccctccaaatatgtgaacttcctgtacctggccag
ccactatgagaagctgaagggctcccccgaggataatgagcagaaacagctgtttgtggaacagcacaaacactacctggacgagatc
atcgagcagatcagcgagttctccaagagagtgatcctggccgacgctaatctggacaaggtgctgagcgcctacaacaagcacagag
acaagcctatcagagagcaggccgagaatatcatccacctgtttaccctgaccaatctgggagcccctgccgccttcaagtactttgaca
ccaccatcgaccggaagaggtacaccagcaccaaagaggtgctggacgccaccctgatccaccagagcatcaccggcctgtacgagac
acggatcgacctgtctcagctgggaggcgacgccgactataaggaccacgacggagactacaaggatcatgatattgattacaaagac
gatgacgataagagcctgggcagcggctcccccaagaaaaaacgcaaggtggaagatcctaagaaaaagcggaaagtgtgataa**GC
TAGCAGATCTTTTTCCCTCTGCCAAAAATTATGGGGACATCATGAAGCCCCTTGAGCATCTGACTTCTG
GCTAATAAAGGAAATTTATTTTCATTGCAATAGTGTGTTGGAATTTTTTGTGTCTCTCACTCGGAAGGA
CATA(HOMOLOGYARMSC) (SEQ ID NO:21)**

β-actin promoter – underlined and upper case
dCas9-3xFlag-2xNLS – lower case
beta-globin poly (A) signal – bold and upper case

FIG. 6

Homology arms for insertion at position: chr9:107,422,356 / hg38

N terminus

Short arm: GCTTCTCCAGCCCTGGCCTGGGTCAATCCTTGGGGCCCAGACTGAGCACG (SEQ ID NO:22)
Long arm:
GTTTTATCAGTTTTGGAGGATGTACATAAATATATAGAATGAGAGTCTCAAAACTAATCTTGTAGCTACG
CCTGTGATGGGCTAATTGATGAATCAGTGCTGGAGAATGGGTCACAGTGGCAAATGAGGCTGGAGAGG
CCCGTGAGCTGCTGTCCCAGAGGGCCTGGGATGTCCTGCAGGGAGCTTGGCATGAGAAACCTTGGAGA
GTTTTAAGCAAGGGCTGATGTGGGCTGCCTAGAAAGGCATGGATGAGAGAAGCCTGGAGACAGGGAT
CCCAGGGAAACGCCCATGCAATTAGTCTATTTCTGCTGCAAGTAAGCATGCATTTGTAGGCTTGATGCTT
TTTTTCTGCTTCTCCAGCCCTGGCCTGGGTCAATCCTTGGGGCCCAGACTGAGCACG (SEQ ID NO:23)

C terminus

Short arm: TGATGGCAGAGGAAAGGAAGCCCTGCTTCCTCCAGAGGGCGTCGCAGGAC (SEQ ID NO:24)
Long arm:
TGATGGCAGAGGAAAGGAAGCCCTGCTTCCTCCAGAGGGCGTCGCAGGACAGCTTTTCCTAGACAGGG
GCTAGTATGTGCAGCTCCTGCACCGGGATACTGGTTGACAAGTTTGGCTGGGCTGGAAGCCAGCACCTA
GGGAGGTCCCTGGAAGGGGCCAGCCTCACCAGGAGAGGAGGGACCTGGCCCTTCAGGGTCGAGCTCA
ACAGAGGAAAAGATCTCAGGGCACCCAGAGCCCAGTGGCTTTCAGCACCTGCATGAAAATCAGAGATC
AACCAGATTACCCCATATTGCCCAAGAGAAAACTGAGGCCAGAAAGTGATGGAGCTTGCCCAGGACCCC
AGAGGGTGTTAGAGGCAGGCCAGAACCAGAGGACAGCTCTGTCCCAGCACTTGCCCTCC (SEQ ID NO:25)

FIG. 7

Homology arms for insertion at position: chr1:179,826,688/ hg38

N terminus

Short arm: CACCCTCCTCCACCCACCCAAATCCTACCTGTCCTTCAAACCTTGTCCAGG (SEQ ID NO:26)

Long arm:

TCACTGGGGTAGACCCCACAGCCTTCTCTCCAGGCCTTGCTGCACTGGGCCATCTCCTCGTGGTCCCAGG
ATGTCCCAGCAAGCGGAGCACTGACCACAGGAGTAGGGGTGAGGGAACAAACCAGGCATACACTCCTG
GCATCGCCAGACCTTGGCCCTGAACCCCACCCAAACGGATCCATTTAAATGATCCTGAGGTCTAGGAACC
CGCTGGGATTCGACAGAAATGTGAGCCCATCAGGTATTCAAAAAGGGTCTGTGCCAGTCCCCCAAATAG
TTTAAAAACAACAACACTAGAAATTTTCTCTATCCACCTGGAATGAGTTTTCGGTTACAATTCTGACCCCA
TGCACCCTCCTCCACCCACCCAAATCCTACCTGTCCTTCAAACCTTGTCCAGG (SEQ ID NO:27)

C terminus

Short arm: ATTCTATGATTTATTCCCCTGAGGCCCCTGGAAGCAATCACTCCCTTTTC (SEQ ID NO:28)

Long arm:

ATTCTATGATTTATTCCCCTGAGGCCCCTGGAAGCAATCACTCCCTTTTCTGGATAAGCAAAACATCCTCT
CTCCACCTCCCCGCGTGTTGCTGGATTGCTGGTATCTGGCATGCCCTATATTTTCCCTTGCGGACAGGTTG
TTCCTTGAGGCTGGATTCCCCACTGCACTGGCCCCAGCACCCAACACAGGCCTTGCACACGCTTTACAGC
CAGCCAAAGCCAGCTGAAGGAACCAGATGCACTCCTGTCTTTCATAGGCTGGAGGGTTTTTTTTTTTCTTT
TCAATGTCTTTCACTGTGGTAAAATACACATATAAAGCTTATCACCTTCACCATTAAGTGGGCAGCAGTTC
AGTGGTATCAAGCACATTCATAATGTGTGACCGTCACCACCATCCA (SEQ ID NO:29)

COMPOSITIONS AND METHODS FOR INCREASING HOMOLOGY-DIRECTED REPAIR

CROSS-REFERENCE

This application is a national stage entry of international PCT Patent Application No. PCT/US21/40652, filed Jul. 7, 2021, which application claims the benefit of U.S. Provisional Patent Application No. 63/049,316, filed Jul. 8, 2020, which applications are incorporated herein by reference in their entirety.

INTRODUCTION

Molecular self-assembly with scaffolded DNA origami offers a route for folding nucleic acid molecules in user-defined ways, to generate DNA nanostructures. DNA nanostructures comprises a single-stranded DNA that is folded into distinct shapes via oligonucleotides termed "staples."

Engineered nuclease systems can be used to cleave a target DNA at a specified location. Examples of engineered nuclease systems include TALENs, zinc finger nucleases, meganucleases, and CRISPR-Cas systems. CRISPR-Cas systems include Cas proteins, which are involved in acquisition, targeting and cleavage of foreign DNA or RNA, and a guide RNA(s), which includes a segment that binds Cas proteins and a segment that binds to a target nucleic acid. For example, Class 2 CRISPR-Cas systems comprise a single Cas protein bound to a guide RNA (gRNA), where the Cas protein binds to and cleaves a targeted nucleic acid. Introduction of a break in a nucleic acid (e.g. genome) can facilitate the introduction of a donor nucleic acid. The programmable nature of these nuclease systems has facilitated their use as a versatile technology for use in modification of target nucleic acid.

SUMMARY

The present disclosure provides compositions comprising a gene-editing polypeptide, a single-stranded donor DNA, and one or more staple oligonucleotides. The present disclosure provides compositions comprising a DNA nanostructure and a gene-editing polypeptide. The present disclosure provides gene editing methods using the compositions. The present disclosure provides methods of using the compositions to produce a genetically modified cell. The present disclosure provides kits useful for carrying out gene editing.

BRIEF DESCRIPTION OF THE DRAWINGS

FIG. 3A-3P provide amino acid sequences of various CRISPR/Cas effector polypeptides.

FIG. 4 provides an example of a nucleotide sequence of interest in a donor DNA.

FIG. 5 provides an example of a nucleotide sequence of interest in a donor DNA.

FIG. 6 provides examples of homology arms for insertion into chr9:107,422,356/hg38.

FIG. 7 provides nucleotide sequences of examples of homology arms for insertion into chr1:179,826,688/hg38.

DEFINITIONS

Figure 1A:
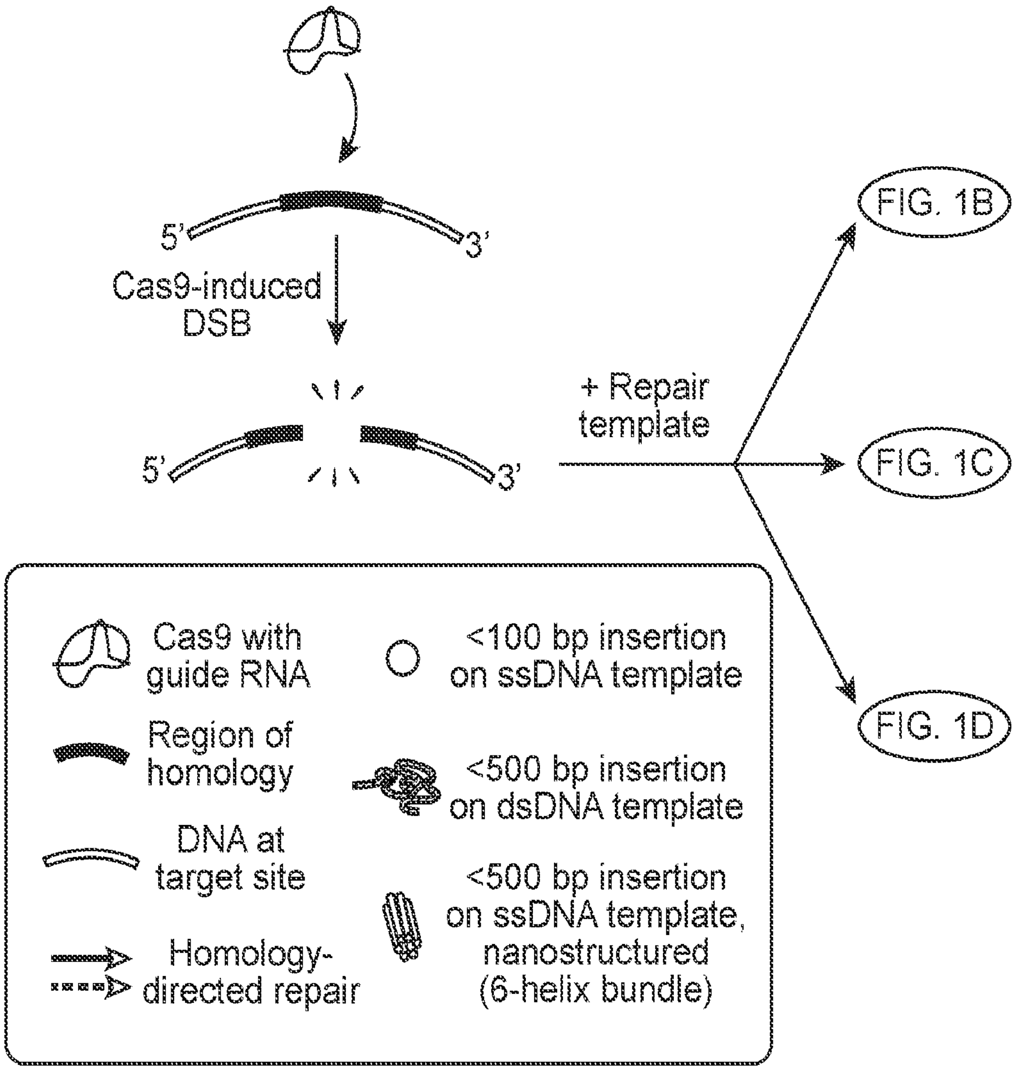
FIG. 1A-1D depict use of DNA nanostructures for integration of large DNA insertions via homology-directed repair (HDR).
Figure 1B:
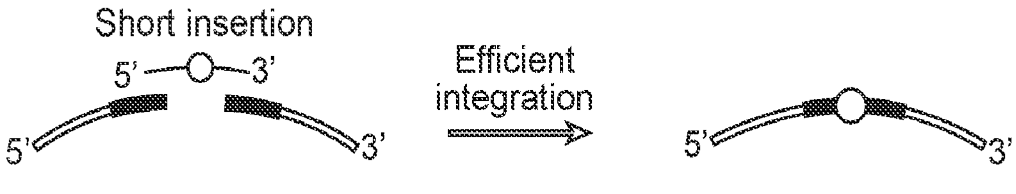
Figure 1C:
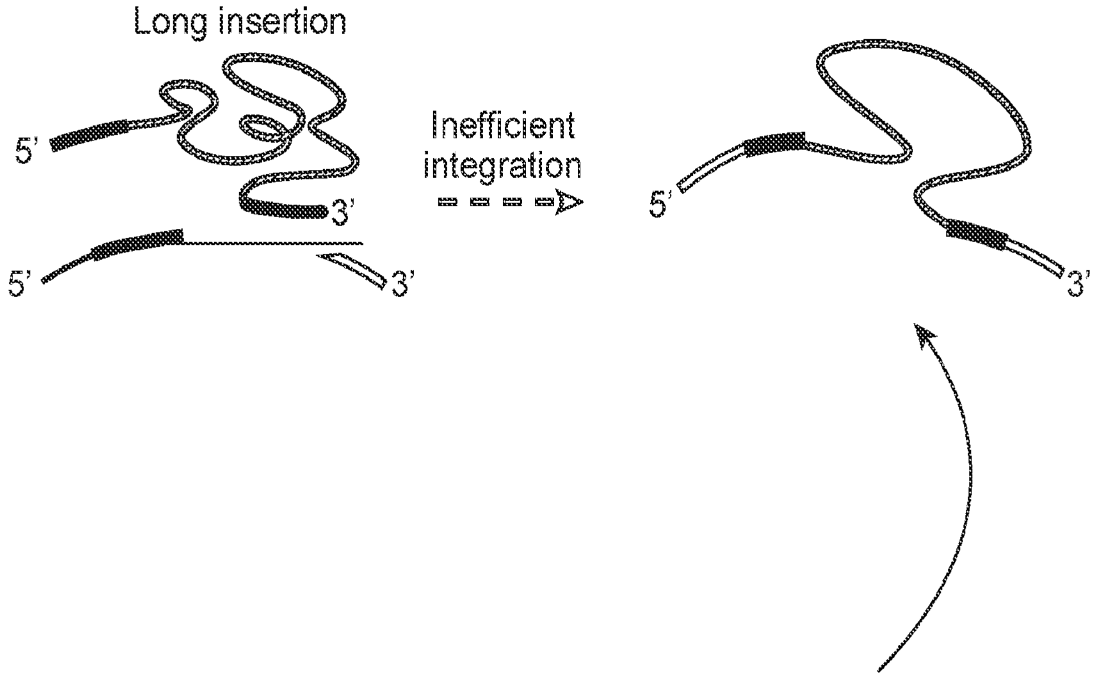
Figure 1D:
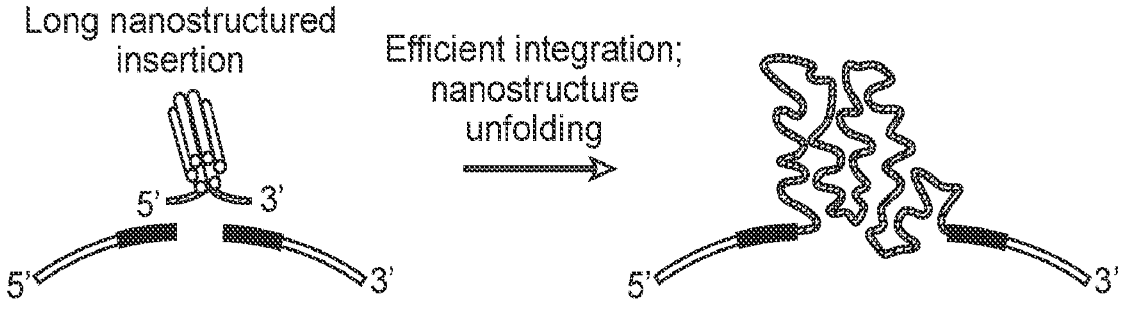

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a DNA target nucleic acid base pairs with a guide RNA, etc.): guanine (G) can also base pair with uracil (U). For example, G/U base-pairing is at least partially responsible for the degeneracy (i.e., redundancy) of the genetic code in the context of tRNA anti-codon base-pairing with codons in mRNA. Thus, in the context of this disclosure, a guanine (G) (e.g., of dsRNA duplex of a guide RNA molecule; of a guide RNA base pairing with a target nucleic acid, etc.) is considered complementary to both a uracil (U) and to an adenine (A). For example, when a G/U base-pair can be made at a given nucleotide position of a dsRNA duplex of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). Temperature, wash solution salt concentration, and other conditions may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a bulge, a loop structure or hairpin structure, etc.). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656), the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489), and the like.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleotide sequence that is transcribed into RNA. A DNA polynucleotide may encode an RNA (mRNA) that is translated into protein (and therefore the DNA and the mRNA both encode the protein), or a DNA polynucleotide may encode an RNA that is not translated into protein (e.g. tRNA, rRNA, microRNA (miRNA), a "non-coding" RNA (ncRNA), a guide RNA, etc.).

A "protein coding sequence" or a sequence that encodes a particular protein or polypeptide, is a nucleotide sequence that is transcribed into mRNA (in the case of DNA) and is translated (in the case of mRNA) into a polypeptide in vitro or in vivo when placed under the control of appropriate regulatory sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence and/or regulate translation of an encoded polypeptide.

As used herein, a "promoter" or a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive expression by the various vectors of the present disclosure.

A "target nucleic acid" as used herein is a polynucleotide (e.g., DNA such as genomic DNA) that includes a site ("target site" or "target sequence") targeted by a modified CRISPR/Cas effector polypeptide of the present disclosure. The target sequence is the sequence to which the guide sequence of a guide nucleic acid (e.g., guide RNA; e.g., a dual guide RNA or a single-molecule guide RNA) will hybridize. For example, the target site (or target sequence) 5'-GAGCAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide RNA is referred to as the "complementary strand" or "target strand"; while the strand of the target nucleic acid that is complementary to the "target strand" (and is therefore not complementary to the guide RNA) is referred to as the "non-target strand" or "non-complementary strand."

A "small interfering" or "short interfering RNA" or siRNA is an RNA duplex of nucleotides that is targeted to a gene interest (a "target gene"). An "RNA duplex" refers to the structure formed by the complementary pairing between two regions of an RNA molecule. siRNA is "targeted" to a gene in that the nucleotide sequence of the duplex portion of the siRNA is complementary to a nucleotide sequence of the targeted gene. In some cases, the length of the duplex of siRNAs is less than 30 nucleotides. In some cases, the duplex can be 29, 28, 27, 26, 25, 24, 23, 22, 21, 20, 19, 18, 17, 16, 15, 14, 13, 12, 11 or 10 nucleotides in length. In some cases, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some cases, the loop is 5, 6, 7, 8, 9, 10, 11, 12 or 13 nucleotides in length. The hairpin structure can also contain 3' or 5' overhang portions. In some cases, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA that is a fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, humans, non-human primates, ungulates, felines, canines, bovines, ovines, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a gene-editing polypeptide" includes a plurality of such polypeptide and reference to "the staple oligonucleotide" includes reference to one or more staple oligonucleotide and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions comprising a gene-editing polypeptide, a single-stranded donor DNA, and one or more staple oligonucleotides. The present disclosure provides compositions comprising a DNA nanostructure and a gene-editing polypeptide. The present disclosure provides gene editing methods using the compositions. The present disclosure provides methods of using the compositions to produce a genetically modified cell. The present disclosure provides kits useful for carrying out gene editing.

Figure 2A:
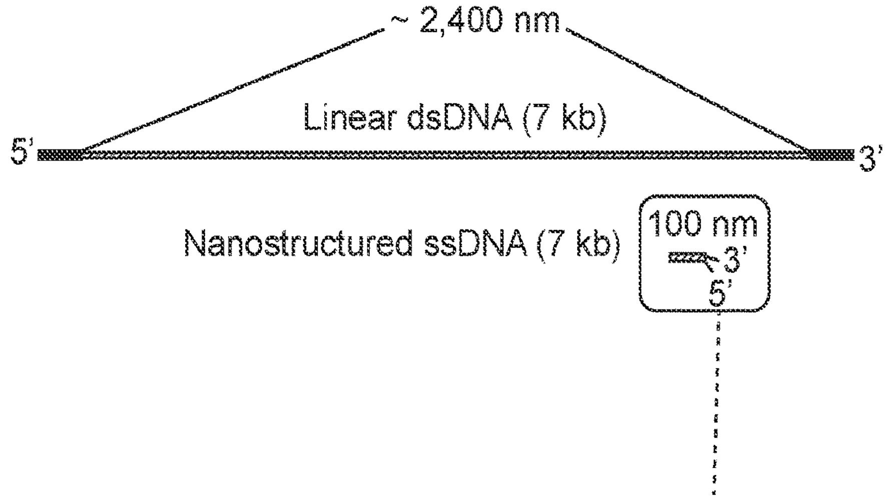
FIG. 2A-2C depict DNA origami to generate highly compact repair templates.
Figure 2B:
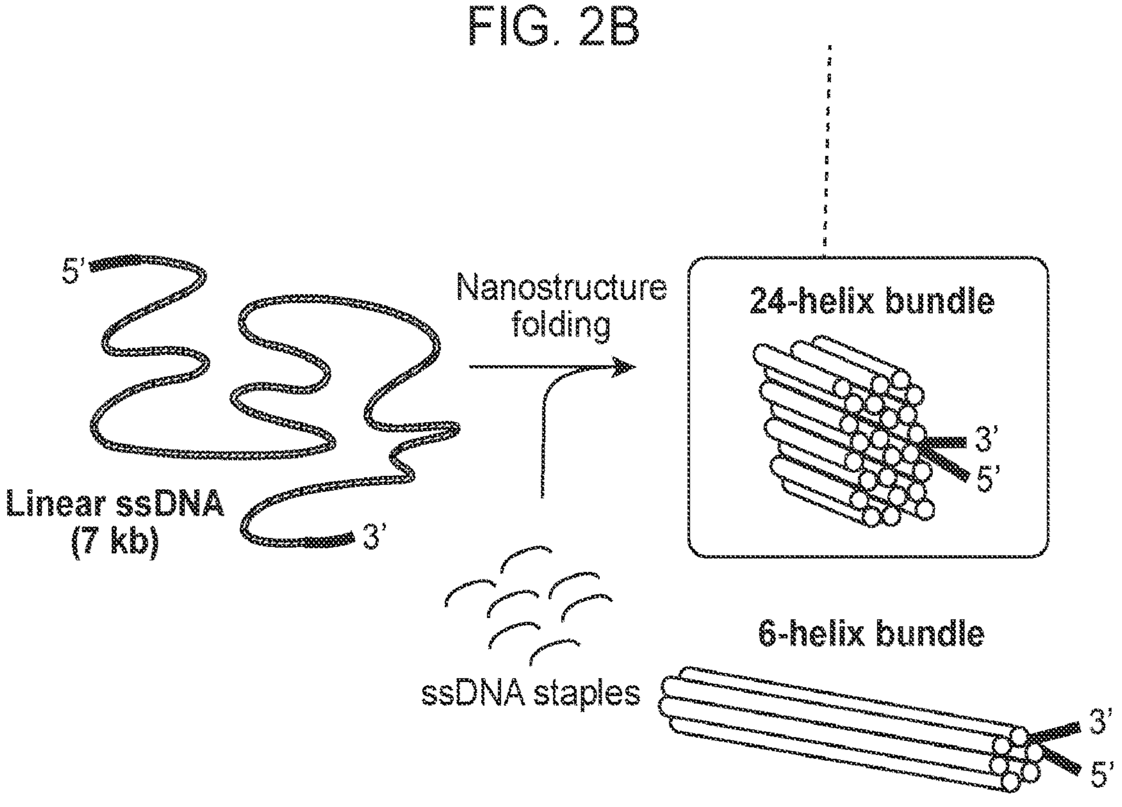
Figure 2C:
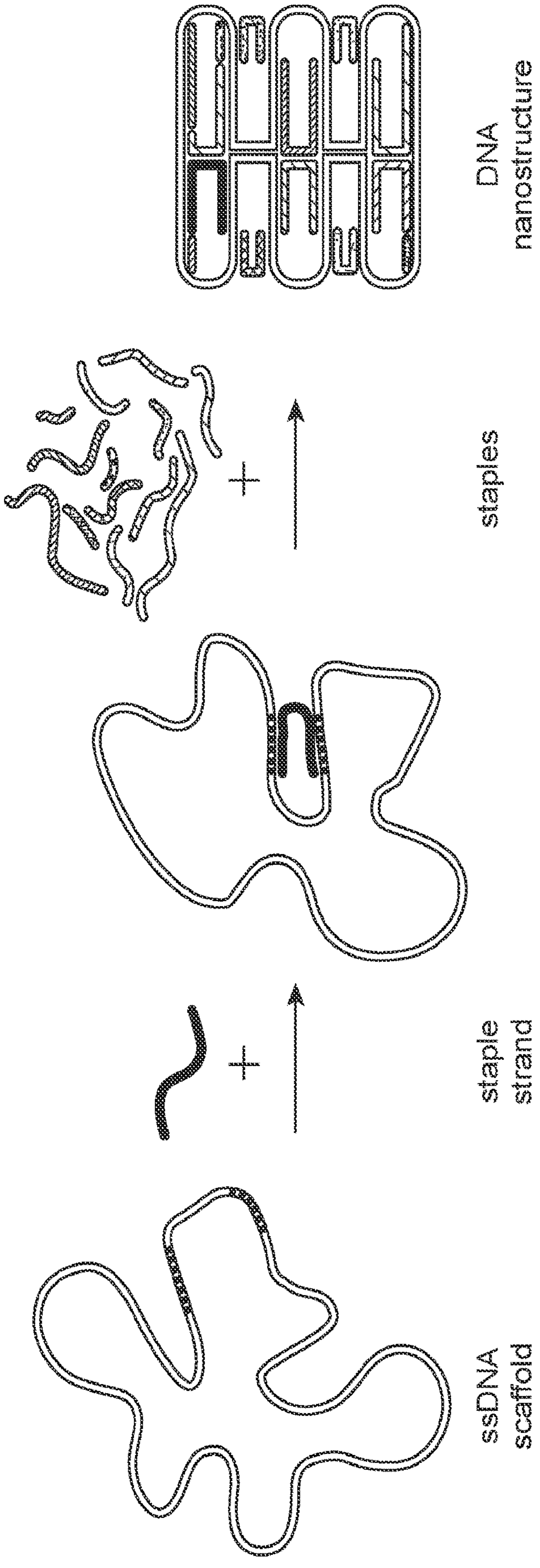

Features of the present disclosure are illustrated schematically in FIG. 1A-1D and in FIG. 2A-2C. As depicted schematically in FIG. 1A, in CRISPR-mediated homology-directed repair (HDR), a CRISPR/Cas effector polypeptide (e.g., a Cas9 polypeptide) and its guide RNA are introduced into a cell, along with a donor DNA encoding new genetic information (where such a donor DNA may also be a repair template). The CRISPR/Cas effector polypeptide is directed by its guide RNA to cleave at a genomic target site of interest, generating a blunt-ended double-strand break (DSB) in the DNA. Repair templates are then used by the cell to resolve the DSB through HDR, incorporating the desired changes. As depicted schematically in FIG. 1B, short donor DNA templates (<100 nucleotides in length) are efficiently integrated via HDR when introduced as single-stranded DNA (ssDNA) molecules with 30-90 nucleotide homology arms. As depicted schematically in FIG. 1C, longer donor DNA (e.g., >500 nucleotides in length) are introduced as double-stranded DNA (dsDNA) molecules to avoid nuclease-mediated template degradation in the cytosol, and are generally flanked by longer (300-500 bp) homology arms. Long repair templates are poorly integrated via HDR without a combination of changes to delivery method, template sequence, and/or cell physiology. As depicted schematically in FIG. 1D, longer donor DNA molecules can be folded into compact, nuclease-resistant nanostructures through scaffolded DNA origami methods, bringing the 5' and 3' homology arms of the donor DNA closer together.

FIG. 2A-2C depict use of DNA origami to generate highly compact repair templates (DNA nanostructures comprising a donor DNA folded using "staple" oligonucleotides). As depicted schematically in FIG. 2A, a 7-kbp linear double-stranded DNA (dsDNA) molecule would measure about 2,400 nm in length, not including its 400 bp homology arms. The same template as a nanostructured molecule would measure 100 nm in length, not including homology arms. As illustrated schematically in FIG. 2B, a 7-kb linear single-stranded DNA (ssDNA) molecule can be folded into structures such as a 24-helix bundle or 6-helix bundle, with the insertion region nanostructured into helices and the homology arms left as ssDNA. Folding of ssDNA into a nanostructure via DNA origami methods is accomplished by addition of strategically designed ssDNA "staple" oligonucleotides. Use of staple oligonucleotides to generate a DNA nanostructure is depicted schematically in FIG. 2C.

Compositions

The present disclosure provides compositions for gene editing (e.g., editing a target nucleic acid by homology-directed repair (HDR)), where the compositions comprise: a) a gene-editing polypeptide; b) a single-stranded donor DNA; and c) one or more "staple" nucleic acids. The single-stranded donor DNA comprises: i) a first homology arm at or near the 5' end of the donor DNA, wherein the first homology arm comprises a nucleotide sequence that is at least partially complementary to a first nucleotide sequence in the target nucleic acid; and ii) a second homology arm at or near the 3' end of the donor DNA, wherein the second homology arm comprises a nucleotide sequence that is at least partially complementary to a second nucleotide sequence in the target nucleic acid. The single-stranded donor DNA comprises a nucleotide sequence of interest (an "intervening nucleotide sequence" or a "nucleic acid of interest") between the first homology arm and the second homology arm. The one or more staple nucleic acids are least partially complementary to the donor DNA (i.e., at least partially complementary to the nucleotide sequence of interest) such that the one or more staple oligonucleotides hybridize to the donor DNA, such that the donor DNA folds into a nanostructure (a "donor DNA nanostructure") in which the first homology arm and the second homology arm are brought into proximity to one another. The donor DNA nanostructure is more compact than single-stranded donor DNA that is not contacted with the staple nucleic acids. The closer proximity of the first homology arm and the second homology arm to one another in the donor DNA nanostructure, compared to the single-stranded donor DNA that is not contacted with the staple nucleic acids, provides for increased efficiency of HDR, compared to HDR carried out with single-stranded donor DNA that is not contacted with the staple nucleic acids. Single-stranded donor DNA that is not contacted with the staple nucleic acids is also referred to herein as "unfolded single-stranded donor DNA" or "linear single-stranded donor DNA." The first and second homology arms remain single stranded; the staple oligonucleotides generally do not hybridize to the first homology arm or the second homology arm.

The one or more staple nucleic acids (also referred to herein as "staple oligonucleotides") comprise nucleotide sequences that are least partially complementary to the donor DNA such that the one or more staple oligonucleotides hybridize to the donor DNA. The staple oligonucleotides are designed to fold the single-stranded donor DNA into a nanostructure in such a way that the first homology arm and the second homology arm are brought into proximity to one another. The present disclosure provides a composition comprising: a) a gene editing polypeptide; and b) a DNA nanostructure comprising a donor DNA and at least one staple oligonucleotide, wherein the donor DNA comprises a first homology arm and a second homology arm that are in proximity to one another by virtue of the folding of the donor DNA induced by the staple oligonucleotide(s).

The first and the second homology arms are brought into proximity to one another in the nanostructure formed by hybridization of the single-stranded donor DNA with the one or more staple oligonucleotides, relative to their positions in the linear single-stranded donor DNA (donor DNA not hybridized with the one or more staple oligonucleotides).

For example, the distance between the first and the second homology arms can be from about 5 nm to about 150 nm from one another; e.g., from about 5 nm to about 10 nm, from about 10 nm to about 20 nm, from about 20 nm to about 25 nm, from about 25 nm to about 50 nm, from about 50 nm to about 75 nm, from about 75 nm to about 100 nm, from about 100 nm to about 110 nm, from about 110 nm to about 120 nm, from about 120 nm to about 130 nm, from about 130 nm to about 140 nm, or from about 140 nm to about 150 nm.

Staple Oligonucleotides

A composition of the present disclosure can comprise from 1 to 250 staple oligonucleotides; e.g., a composition of the present disclosure can comprise from 1 to 4, from 1 to 5, from 1 to 6, from 1 to 7, from 5 to 15, from 4 to 6, from 6 to 8, from 8 to 10, from 10 to 12, from 12 to 14, from 14 to 16, from 16 to 18, from 18 to 20, from 20 to 25, from 25 to 50, from 50 to 75, from 75 to 100, from 100 to 125, from 125 to 150, from 150 to 175, from 175 to 200, from 200 to 225, or from 225 to 250, staple oligonucleotides. In some cases, a composition of the present disclosure comprises 2 staple oligonucleotides. In some cases, a composition of the present disclosure comprises 3 staple oligonucleotides. In some cases, a composition of the present disclosure comprises 4 staple oligonucleotides. In some cases, a composition of the present disclosure comprises 5 staple oligonucleotides. In some cases, a composition of the present disclosure comprises 6 staple oligonucleotides. In some cases, a composition of the present disclosure comprises 7 staple oligonucleotides. In some cases, a composition of the present disclosure comprises 8 staple oligonucleotides. In some cases, a composition of the present disclosure comprises 9 staple oligonucleotides. In some cases, a composition of the present disclosure comprises 10 staple oligonucleotides. In some cases, a composition of the present disclosure comprises 11 staple oligonucleotides. In some cases, a composition of the present disclosure comprises 12 staple oligonucleotides. In some cases, a composition of the present disclosure comprises 13 staple oligonucleotides. In some cases, a composition of the present disclosure comprises 14 staple oligonucleotides. In some cases, a composition of the present disclosure comprises 15 staple oligonucleotides. In some cases, a composition of the present disclosure comprises 16 staple oligonucleotides. In some cases, a composition of the present disclosure comprises 17 staple oligonucleotides. In some cases, a composition of the present disclosure comprises 18 staple oligonucleotides. In some cases, a composition of the present disclosure comprises 19 staple oligonucleotides. In some cases, a composition of the present disclosure comprises 20 staple oligonucleotides. In some cases, a composition of the present disclosure comprises from 20 to 25 staple oligonucleotides. In some cases, a composition of the present disclosure comprises from 25 to 50 staple oligonucleotides. In some cases, a composition of the present disclosure comprises from 50 to 75 staple oligonucleotides. In some cases, a composition of the present disclosure comprises from 75 to 100 staple oligonucleotides. In some cases, a composition of the present disclosure comprises from 100 to 125 staple oligonucleotides. In some cases, a composition of the present disclosure comprises from 125 to 150 staple oligonucleotides. In some cases, a composition of the present disclosure comprises from 150 to 175 staple oligonucleotides. In some cases, a composition of the present disclosure comprises 175 to 200 staple oligonucleotides. In some cases, a composition of the present disclosure comprises from 200 to 225 staple oligonucleotides. In some cases, a composition of the present disclosure comprises from 225 to 250 staple oligonucleotides. In some cases, a composition of the present disclosure comprises from 5 to 15 staple oligonucleotides. In some cases, a composition of the present disclosure comprises from 5 to 10 staple oligonucleotides. In some cases, a composition of the present disclosure comprises from 3 to 15 staple oligonucleotides. In some cases, a composition of the present disclosure comprises from 3 to 10 staple oligonucleotides. In some cases, a composition of the present disclosure comprises from 5 to 20 staple oligonucleotides. In some cases, a composition of the present disclosure comprises from 5 to 25 staple oligonucleotides.

Each staple oligonucleotide can independently have a length of from about 6 nucleotides to about 60 nucleotides. For example, each staple oligonucleotide can independently have a length of from about 6 nucleotides (nt) to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 45 nt, from about 45 nt to about 50 nt, from about 50 nt to about 55 nt, or from about 55 nt to about 60 nt. In some cases, each staple oligonucleotide independently has a length of from about 20 nucleotides to about 50 nucleotides. In some cases, each staple oligonucleotide independently has a length of from about 15 nucleotides to about 30 nucleotides. In some cases, each staple oligonucleotide independently has a length of from about 20 nucleotides to about 40 nucleotides.

The staple oligonucleotides bind to the single-stranded donor DNA at sites internal to the first and second homology arms (i.e., the staple oligonucleotides bind to the nucleotide sequence that is between the first and second homology arms). In other words, the staple oligonucleotides do not bind to the first homology arm or to the second homology arm.

A staple oligonucleotide comprises: i) a first nucleotide sequence that hybridizes with a first nucleotide sequence ("first donor nucleotide sequence") in the donor DNA; and ii) a second nucleotide sequence that hybridizes with a second nucleotide sequence ("second donor nucleotide sequence") in the donor DNA. The first donor nucleotide sequence and the second donor nucleotide sequence can be separated from one another by from 5 nucleotides to 10,000 nucleotides; the nucleotide sequence between the first donor nucleotide sequence and the second donor nucleotide sequence is referred to as the "intervening donor nucleotide sequence" or "nucleotide sequence of interest." The intervening nucleotide sequence can be from 5 nucleotides (nt) to 10,000 nt in length; e.g., the intervening nucleotide sequence can be from 5 nt to about 10 nt, from about 10 nt to about 25 nt, from about 25 nt to about 50 nt, from about 50 nt to about 100 nt, from about 100 nt to about 250 nt, from about 250 nt to about 500 nt, from about 500 nt to about 1,000 nt, from about 1,000 nt to about 1500 nt, from about 1500 nt to about 2000 nt, from about 2000 nt to about 2500 nt, from about 2500 nt to about 5000 nt, from about 5000 nt to about 7500 nt, or from about 7500 to about 10,000 nt. Upon hybridization (binding) of the staple oligonucleotide to the donor DNA, the first donor nucleotide sequence and the second donor nucleotide sequence, which both bind to the same staple oligonucleotide, are brought into proximity to one another. The intervening donor nucleotide sequence can be in the form of a loop, a helix, etc.

In some cases, the staple oligonucleotides are designed to fold the linear single-stranded donor DNA into a two-dimensional or three-dimensional nanostructure. In some cases, the staple oligonucleotides are designed to fold the linear single-stranded donor DNA into a nanostructure comprising parallel helices. In some cases, the staple oligonucleotides are designed to fold the linear single-stranded donor DNA into a two-dimensional or 3-dimensional polygonal network wherein the edges of the network are comprised of blocks of at least two parallel helices. In some cases, the staple oligonucleotides are designed to fold the linear single-stranded donor DNA into a 6-helix nanostructure. In some cases, the staple oligonucleotides are designed to fold the linear single-stranded donor DNA into a 24-helix nanostructure. In some cases, the linear single-stranded donor DNA will be folded, using staple oligonucleotides, into a multilayer DNA nanostructure. In some cases, the multilayer DNA nanostructure will be folded into a honeycomb lattice (see, e.g., Ke et al. (2012) *J. Am. Chem. Soc.* 134:1770). In some cases, the multilayer DNA nanostructure will be folded in a square lattice (see, e.g., Ke et al. (2009) *J. Am. Chem. Soc.* 131:15903). In some cases, the multilayer DNA nanostructure will incorporate curvature (see, e.g., Han et al. (2011) *Science* 332:342). In some cases, some parts of the DNA nanostructure will remain single stranded and will not include staples (will not have staple oligonucleotides hybridized to the DNA), to allow for flexibility.

One or more of the staple oligonucleotides can include a detectable label. Suitable detectable labels include fluorophores. Examples of fluorophores include, but are not limited to: an Alexa Fluor® dye (e.g., Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like), an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine isothiocyanate (TRITC), tetramethylrhodamine (TMR), Silicon Rhodamine (SiR), Texas Red, Oregon Green, Pacific Blue, Pacific Green, and Pacific Orange.

In some cases, a staple oligonucleotide comprises a transcription factor binding site (e.g., to promote import into the nucleus) and/or a site for recruitment (binding) of DNA repair proteins. Transcription factor binding sites are known in the art. A non-limiting example of a transcription factor binding site is a nucleotide sequence comprising CCAAT. See e.g., Khamis et al. (2018) *Nucleic Acids Research* 46:e72; The ENCODE Project Consortium (2012) *Nature* 489:57.

Donor DNA

By a "donor nucleic acid" or "donor polynucleotide" or "donor DNA" it is meant a single-stranded DNA to be inserted at a site cleaved by a gene-editing polypeptide (e.g., a CRISPR/Cas effector protein; a TALEN; a ZFN; a meganuclease) (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology.

Approximately 25, 50, 100, or 200 nucleotides, or more than 200 nucleotides, of sequence homology between a donor DNA and a genomic sequence (or any integral value between 10 and 200 nucleotides, or more) can support homology-directed repair. Donor polynucleotides can be of any length, e.g., 50 nucleotides or more, 100 nucleotides or more, 250 nucleotides or more, 500 nucleotides or more, 1000 nucleotides or more, 5000 nucleotides or more, etc. A suitable donor DNA can be from 50 nucleotides to 100 nucleotides, from 100 nucleotides to 500 nucleotides, from 500 nucleotides to 1000 nucleotides, from 1000 nucleotides to 5000 nucleotides, or from 5000 nucleotides to 10,000 nucleotides, or more than 10,000 nucleotides, in length.

As noted above, the donor DNA comprises a first homology arm and a second homology arm. The first homology arm is at or near the 5' end of the donor DNA; and comprises a nucleotide sequence that is at least partially complementary to a first nucleotide sequence in a target nucleic acid. The second homology arm is at or near the 3' end of the donor DNA; and comprises a nucleotide sequence that is at least partially complementary to a second nucleotide sequence in the target nucleic acid. The first and second homology arms can each independently have a length of from about 10 nucleotides to 400 nucleotides; e.g., from 10 nucleotides (nt) to 15 nt, from 15 nt to 20 nt, from 20 nt to 25 nt, from 25 nt to 30 nt, from 30 nt to 35 nt, from 35 nt to 40 nt, from 40 nt to 45 nt, from 45 nt to 50 nt, from 50 nt to 75 nt, from 75 nt to 100 nt, from 100 nt to 125 nt, from 125 nt to 150 nt, from 150 nt to 175 nt, from 175 nt to 200 nt, from 200 nt to 225 nt, from 225 nt to 250 nt, from 250 nt to 275 nt, from 275 nt to 300 nt, from 325 nt to 350 nt, from 350 nt to 375 nt, or from 375 nt to 400 nt.

The first homology arm and the second homology arm of the donor DNA flank a nucleotide sequence ("a nucleotide sequence of interest" or "an intervening nucleotide sequence") that is to be introduced into a target nucleic acid. The nucleotide sequence of interest can comprise: i) a nucleotide sequence encoding a polypeptide of interest; ii) a nucleotide sequence encoding an exon of a gene; iii) a promoter sequence; iv) an enhancer sequence; v) a nucleotide sequence encoding a non-coding RNA; or vi) any combination of the foregoing.

The donor DNA can provide for gene correction, gene replacement, gene tagging, transgene insertion, nucleotide deletion, gene disruption, gene mutation, etc. For example, the donor DNA can be used to add, e.g., insert or replace, nucleic acid material to a target DNA (e.g. to "knock in" a nucleic acid that encodes a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, enhancer, etc.), to modify a nucleic acid sequence (e.g., introduce a mutation), and the like. For example, the donor DNA can be used to modify DNA in a site-specific, i.e.

"targeted", way; for example gene knock-out, gene knock-in, gene editing, gene tagging, etc., as used in, for example, gene therapy, e.g. to treat a disease; or as an antiviral, antipathogenic, or anticancer therapeutic, the production of genetically modified organisms in agriculture, the large scale production of proteins by cells for therapeutic, diagnostic, or research purposes, the induction of pluripotent stem cells, biological research, the targeting of genes of pathogens for deletion or replacement, etc.

In some cases, the donor DNA comprises a nucleotide sequence encoding a polypeptide of interest. Polypeptides of interest include, e.g., a) functional versions of a polypeptide that comprises one or more amino acid substitutions, insertions, and/or deletions and that exhibits reduced function, e.g., where the reduced function is associated with or causes a pathological condition; b) fluorescent polypeptides; c) hormones; d) receptors for ligands; e) ion channels; f) neurotransmitters; g) and the like.

In some cases, the donor DNA comprises a nucleotide sequence that encodes a wild-type protein that is lacking in the recipient cell. In some cases, the donor DNA encodes a wild type factor (e.g. Factor VII, Factor VIII, Factor IX and the like) involved in coagulation. In some cases, the donor DNA comprises a nucleotide sequence that encodes a therapeutic antibody. In some cases, the donor DNA comprises a nucleotide sequence that encodes an engineered protein or receptor. In some cases, the engineered receptor is a T cell receptor (TCR), a natural killer (NK) receptor (NKR), or a B cell receptor (BCR). In some cases, the engineered TCR or NKR targets a cancer marker (e.g., a polypeptide that is expressed (e.g., over-expressed) on the surface of a cancer cell). In some cases, the donor DNA comprises a nucleotide sequence that encodes a chimeric antigen receptor (CAR). In some cases, the CAR targets a cancer marker. Donor DNAs encoding CAR, TCR, and/or NCR proteins may be folded into DNA origami structures (DNA nanostructures) and delivered into T cells or NK cells in vitro or in vivo.

Non-limiting examples of polypeptides that can be encoded by a donor DNA include, e.g., IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), CTSK (cathepsin K), PTGIR (prostaglandin 12 (prostacyclin) receptor (IP)), KCNJ11 (potassium inwardly-rectifying channel, subfamily J, member 11), INS (insulin), CRP (C-reactive protein, pentraxin-related), PDGFRB (platelet-derived growth factor receptor, beta polypeptide), CCNA2 (cyclin A2), PDGFB (platelet-derived growth factor beta polypeptide (simian sarcoma viral (v-sis) oncogene homolog)), KCNJ5 (potassium inwardly-rectifying channel, subfamily J, member 5), KCNN3 (potassium intermediate/small conductance calcium-activated channel, subfamily N, member 3), CAPN10 (calpain 10), PTGES (prostaglandin E synthase), ADRA2B (adrenergic, alpha-2B-, receptor), ABCGS (ATP-binding cassette, sub-family G (WHITE), member 5), PRDX2 (peroxiredoxin 2), CAPNS (calpain 5), PARP14 (poly (ADP-ribose) polymerase family, member 14), MEX3C (mex-3 homolog C (*C. elegans*)), ACE angiotensin I converting enzyme (peptidyl-dipeptidase A) 1), TNF (tumor necrosis factor (TNF superfamily, member 2)), IL6 (interleukin 6 (interferon, beta 2)), STN (statin), SERPINE1 (serpin peptidase inhibitor, clade E (nexin, plasminogen activator inhibitor type 1), member 1), ALB (albumin), ADIPOQ (adiponectin, C1Q and collagen domain containing), APOB (apolipoprotein B (including Ag(x) antigen)), APOE (apolipoprotein E), LEP (leptin), MTHFR (5,10-methylenetetrahydrofolate reductase (NADPH)), APOA1 (apolipoprotein A-I), EDN1 (endothelin 1), NPPB (natriuretic peptide precursor B), NOS3 (nitric oxide synthase 3 (endothelial cell)), PPARG (peroxisome proliferator-activated receptor gamma), PLAT (plasminogen activator, tissue), PTGS2 (prostaglandin-endoperoxide synthase 2 (prostaglandin G/H synthase and cyclooxygenase)), CETP (cholesteryl ester transfer protein, plasma), AGTR1 (angiotensin II receptor, type 1), HMGCR (3-hydroxy-3-methylglutaryl-Coenzyme A reductase), IGF1 (insulin-like growth factor 1 (somatomedin C)), SELE (selectin E), REN (renin), PPARA (peroxisome proliferator-activated receptor alpha), PON1 (paraoxonase 1), KNG1 (kininogen 1), CCL2 (chemokine (C—C motif) ligand 2), LPL (lipoprotein lipase), vWF (von Willebrand factor), F2 (coagulation factor II (thrombin)), ICAM1 (intercellular adhesion molecule 1), TGFB1 (transforming growth factor, beta 1), NPPA (natriuretic peptide precursor A), IL10 (interleukin 10), EPO (erythropoietin), SOD1 (superoxide dismutase 1, soluble), VCAM1 (vascular cell adhesion molecule 1), IFNG (interferon, gamma), LPA (lipoprotein, Lp(a)), MPO (myeloperoxidase), ESR1 (estrogen receptor 1), MAPK1 (mitogen-activated protein kinase 1), HP (haptoglobin), F3 (coagulation factor III (thromboplastin, tissue factor)), CST3 (cystatin C), COG2 (component of oligomeric Golgi complex 2), MMP9 (matrix metallopeptidase 9 (gelatinase B, 92 kDa gelatinase, 92 kDa type IV collagenase)), SERPINC1 (serpin peptidase inhibitor, clade C (antithrombin), member 1), F8 (coagulation factor VIII, procoagulant component), HMOX1 (heme oxygenase (decycling) 1), APOC3 (apolipoprotein C-III), IL8 (interleukin 8), PROK1 (prokineticin 1), CBS (cystathionine-beta-synthase), NOS2 (nitric oxide synthase 2, inducible), TLR4 (toll-like receptor 4), SELP (selectin P (granule membrane protein 140 kDa, antigen CD62)), ABCA1 (ATP-binding cassette, sub-family A (ABC1), member 1), AGT (angiotensinogen (serpin peptidase inhibitor, clade A, member 8)), LDLR (low density lipoprotein receptor), GPT (glutamic-pyruvate transaminase (alanine aminotransferase)), VEGFA (vascular endothelial growth factor A), NR3C2 (nuclear receptor subfamily 3, group C, member 2), IL18 (interleukin 18 (interferon-gamma-inducing factor)), NOS1 (nitric oxide synthase 1 (neuronal)), NR3C1 (nuclear receptor subfamily 3, group C, member 1 (glucocorticoid receptor)), FGB (fibrinogen beta chain), HGF (hepatocyte growth factor (hepapoietin A; scatter factor)), ILIA (interleukin 1, alpha), RETN (resistin), AKT1 (v-akt murine thymoma viral oncogene homolog 1), LIPC (lipase, hepatic), HSPD1 (heat shock 60 kDa protein 1 (chaperonin)), MAPK14 (mitogen-activated protein kinase 14), SPP1 (secreted phosphoprotein 1), ITGB3 (integrin, beta 3 (platelet glycoprotein 111a, antigen CD61)), CAT (catalase), UTS2 (urotensin 2), THBD (thrombomodulin), F10 (coagulation factor X), CP (ceruloplasmin (ferroxidase)), TNFRSF11B (tumor necrosis factor receptor superfamily, member 11b), EDNRA (endothelin receptor type A), EGFR (epidermal growth factor receptor (erythroblastic leukemia viral (v-erb-b) oncogene homolog, avian)), MMP2 (matrix metallopeptidase 2 (gelatinase A, 72 kDa gelatinase, 72 kDa type IV collagenase)), PLG (plasminogen), NPY (neuropeptide Y), RHOD (ras homolog gene family, member D), MAPK8 (mitogen-activated protein kinase 8), MYC (v-myc myelocytomatosis viral oncogene homolog (avian)), FN1 (fibronectin 1), CMA1 (chymase 1, mast cell), PLAU (plasminogen activator, urokinase), GNB3 (guanine nucleotide binding protein (G protein), beta polypeptide 3), ADRB2 (adrenergic, beta-2-, receptor, surface), APOA5 (apolipoprotein A-V), SOD2 (superoxide dismutase 2, mitochondrial), F5 (coagulation factor V (proaccelerin, labile factor)), VDR (vitamin D (1,25-dihydroxyvitamin D3) receptor), ALOX5 (arachidonate 5-lipoxygenase), HLA-DRB1 (major histocompatibility complex, class II, DR beta 1), PARP1 (poly (ADP-ribose) polymerase 1), CD40LG (CD40 ligand), PON2 (paraoxonase 2), AGER (advanced glycosylation end product-specific receptor), IRS1 (insulin receptor substrate 1), PTGS1 (prostaglandin-endoperoxide synthase 1 (prostaglandin G/H synthase and cyclooxygenase)), ECE1 (endothelin converting enzyme 1), F7 (coagulation factor VII (serum prothrombin conversion accelerator)), URN (interleukin 1 receptor antagonist), EPHX2 (epoxide hydrolase 2, cytoplasmic), IGFBP1 (insulin-like growth factor binding protein 1), MAPK10 (mitogen-activated protein kinase 10), FAS (Fas (TNF receptor superfamily, member 6)), ABCB1 (ATP-binding cassette, subfamily B (MDR/TAP), member 1), JUN (jun oncogene), IGFBP3 (insulin-like growth factor binding protein 3), CD14 (CD14 molecule), PDE5A (phosphodiesterase 5A, cGMP-specific), AGTR2 (angiotensin II receptor, type 2), CD40 (CD40 molecule, TNF receptor superfamily member 5), LCAT (lecithin-cholesterol acyltransferase), CCR5 (chemokine (C—C motif) receptor 5), MMPI (matrix metallopeptidase 1 (interstitial collagenase)), TIMP1 (TIMP metallopeptidase inhibitor 1), ADM (adrenomedullin), DYT10 (dystonia 10), STAT3 (signal transducer and activator of transcription 3 (acute-phase response factor)), MMP3 (matrix metallopeptidase 3 (stromelysin 1, progelatinase)), ELN (elastin), USF1 (upstream transcription factor 1), CFH (complement factor H), HSPA4 (heat shock 70 kDa protein 4), MMP12 (matrix metallopeptidase 12 (macrophage elastase)), MME (membrane metallo-endopeptidase), F2R (coagulation factor II (thrombin) receptor), SELL (selectin L), CTSB (cathepsin B), ANXAS (annexin A5), ADRB1 (adrenergic, beta-1-, receptor), CYBA (cytochrome b-245, alpha polypeptide), FGA (fibrinogen alpha chain), GGT1 (gamma-glutamyltransferase 1), LIPG (lipase, endothelial), HIF1A (hypoxia inducible factor 1, alpha subunit (basic helix-loop-helix transcription factor)), CXCR4 (chemokine (C—X—C motif) receptor 4), PROC (protein C (inactivator of coagulation factors Va and VIIIa)), SCARB1 (scavenger receptor class B, member 1), CD79A (CD79a molecule, immunoglobulin-associated alpha), PLTP (phospholipid transfer protein), ADD1 (adducin 1 (alpha)), FGG (fibrinogen gamma chain), SAA1 (serum amyloid A1), KCNH2 (potassium voltage-gated channel, subfamily H (eag-related), member 2), DPP4 (dipeptidyl-peptidase 4), G6PD (glucose-6-phosphate dehydrogenase), NPR1 (natriuretic peptide receptor A/guanylate cyclase A (atrionatriuretic peptide receptor A)), VTN (vitronectin), KIAA0101 (KIAA0101), FOS (FBJ murine osteosarcoma viral oncogene homolog), TLR2 (toll-like receptor 2), PPIG (peptidylprolyl isomerase G (cyclophilin G)), IL1R1 (interleukin 1 receptor, type I), AR (androgen receptor), CYP1A1 (cytochrome P450, family 1, subfamily A, polypeptide 1), SERPINA1 (serpin peptidase inhibitor, clade A (alpha-1 antiproteinase, antitrypsin), member 1), MTR (5-methyltetrahydrofolate-homocysteine methyltransferase), RBP4 (retinol binding protein 4, plasma), APOA4 (apolipoprotein A-IV), CDKN2A (cyclin-dependent kinase inhibitor 2A (melanoma, p16, inhibits CDK4)), FGF2 (fibroblast growth factor 2 (basic)), EDNRB (endothelin receptor type B), ITGA2 (integrin, alpha 2 (CD49B, alpha 2 subunit of VLA-2 receptor)), CABIN1 (calcineurin binding protein 1), SHBG (sex hormone-binding globulin), HMGB1 (high-mobility group box 1), HSP90B2P (heat shock protein 90 kDa beta (Grp94), member 2 (pseudogene)), CYP3A4 (cytochrome P450, family 3, subfamily A, polypeptide 4), GJA1 (gap junction protein, alpha 1, 43 kDa), CAV1 (caveolin 1, caveolae protein, 22 kDa), ESR2 (estrogen receptor 2 (ER beta)), LTA (lymphotoxin alpha (TNF superfamily, member 1)), GDF15 (growth differentiation factor 15), BDNF (brain-derived neurotrophic factor), CYP2D6 (cytochrome P450, family 2, subfamily D, polypeptide 6), NGF (nerve growth factor (beta polypeptide)), SP1 (Sp 1 transcription factor), TGIF1 (TGFB-induced factor homeobox 1), SRC (v-src sarcoma (Schmidt-Ruppin A-2) viral oncogene homolog (avian)), EGF (epidermal growth factor (beta-urogastrone)), PIK3CG (phosphoinositide-3-kinase, catalytic, gamma polypeptide), HLA-A (major histocompatibility complex, class I, A), KCNQ1 (potassium voltage-gated channel, KQT-like subfamily, member 1), CNR1 (cannabinoid receptor 1 (brain)), FBN1 (fibrillin 1), CHKA (choline kinase alpha), BEST1 (bestrophin 1), APP (amyloid beta (A4) precursor protein), CTNNB1 (catenin (cadherin-associated protein), beta 1, 88 kDa), IL2 (interleukin 2), CD36 (CD36 molecule (thrombospondin receptor)), PRKAB1 (protein kinase, AMP-activated, beta 1 non-catalytic subunit), TPO (thyroid peroxidase), ALDH7A1 (aldehyde dehydrogenase 7 family, member A1), CX3CR1 (chemokine (C—X3-C motif) receptor 1), TH (tyrosine hydroxylase), F9 (coagulation factor IX), GH1 (growth hormone 1), TF (transferrin), HFE (hemochromatosis), IL17A (interleukin 17A), PTEN (phosphatase and tensin homolog), GSTM1 (glutathione S-transferase mu 1), DMD (dystrophin), GATA4 (GATA binding protein 4), F13A1 (coagulation factor XIII, A1 polypeptide), TTR (transthyretin), FABP4 (fatty acid binding protein 4, adipocyte), PON3 (paraoxonase 3), APOC1 (apolipoprotein C—I), INSR (insulin receptor), TNFRSF1B (tumor necrosis factor receptor superfamily, member 1B), HTR2A (5-hydroxytryptamine (serotonin) receptor 2A), CSF3 (colony stimulating factor 3 (granulocyte)), CYP2C9 (cytochrome P450, family 2, subfamily C, polypeptide 9), TXN (thioredoxin), CYP11B2 (cytochrome P450, family 11, subfamily B, polypeptide 2), PTH (parathyroid hormone), CSF2 (colony stimulating factor 2 (granulocyte-macrophage)), KDR (kinase insert domain receptor (a type III receptor tyrosine kinase)), PLA2G2A (phospholipase A2, group IIA (platelets, synovial fluid)), B2M (beta-2-microglobulin), THBS1 (thrombospondin 1), GCG (glucagon), RHOA (ras homolog gene family, member A), ALDH2 (aldehyde dehydrogenase 2 family (mitochondrial)), TCF7L2 (transcription factor 7-like 2 (T-cell specific, HMG-box)), BDKRB2 (bradykinin receptor B2), NFE2L2 (nuclear factor (erythroid-derived 2)-like 2), NOTCH1 (Notch homolog 1, translocation-associated (Drosophila)), UGT1A1 (UDP glucuronosyltransferase 1 family, polypeptide A1), IFNA1 (interferon, alpha 1), PPARD (peroxisome proliferator-activated receptor delta), SIRT1 (sirtuin (silent mating type information regulation 2 homolog) 1 (*S. cerevisiae*)), GNRH1 (gonadotropin-releasing hormone 1 (luteinizing-releasing hormone)), PAPPA (pregnancy-associated plasma protein A, pappalysin 1), ARR3 (arrestin 3, retinal (X-arrestin)), NPPC (natriuretic peptide precursor C), AHSP (alpha hemoglobin stabilizing protein), PTK2 (PTK2 protein tyrosine kinase 2), IL13 (interleukin 13), MTOR (mechanistic target of rapamycin (serine/threonine kinase)), ITGB2 (integrin, beta 2 (complement component 3 receptor 3 and 4 subunit)), GSTT1 (glutathione S-transferase theta 1), IL6ST (interleukin 6 signal transducer (gp130, oncostatin M receptor)), CPB2 (carboxypeptidase B2 (plasma)), CYP1A2 (cytochrome P450, family 1, subfamily A, polypeptide 2), HNF4A (hepatocyte nuclear factor 4, alpha), SLC6A4 (solute carrier family 6 (neurotransmitter transporter, serotonin), member 4), PLA2G6 (phospholipase A2, group VI (cytosolic, calcium-independent)), TNFSF11 (tumor necrosis factor (ligand) superfamily, member 11), SLC8A1 (solute carrier family 8 (sodium/calcium exchanger), member 1), F2RL1 (coagulation factor II (thrombin) receptor-like 1), AKR1A1 (aldo-keto reductase family 1, member A1 (aldehyde reductase)), ALDH9A1 (aldehyde dehydrogenase 9 family, member Al), BGLAP (bone gamma-carboxyglutamate (gla) protein), MTTP (microsomal triglyceride transfer protein), MTRR (5-methyltetrahydrofolate-homocysteine methyltransferase reductase), SULT1A3 (sulfotransferase family, cytosolic, 1A, phenol-preferring, member 3), RAGE (renal tumor antigen), C4B (complement component 4B (Chido blood group), P2RY12 (purinergic receptor P2Y, G-protein coupled, 12), RNLS (renalase, FAD-dependent amine oxidase), CREB1 (cAMP responsive element binding protein 1), POMC (proopiomelanocortin), RAC1 (ras-related C3 botulinum toxin substrate 1 (rho family, small GTP binding protein Rac1)), LMNA (lamin NC), CD59 (CD59 molecule, complement regulatory protein), SCNSA (sodium channel, voltage-gated, type V, alpha subunit), CYP1B1 (cytochrome P450, family 1, subfamily B, polypeptide 1), MIF (macrophage migration inhibitory factor (glycosylation-inhibiting factor)), MMP13 (matrix metallopeptidase 13 (collagenase 3)), TIMP2 (TIMP metallopeptidase inhibitor 2), CYP19A1 (cytochrome P450, family 19, subfamily A, polypeptide 1), CYP21A2 (cytochrome P450, family 21, subfamily A, polypeptide 2), PTPN22 (protein tyrosine phosphatase, non-receptor type 22 (lymphoid)), MYH14 (myosin, heavy chain 14, non-muscle), MBL2 (mannose-binding lectin (protein C) 2, soluble (opsonic defect)), SELPLG (selectin P ligand), AOC3 (amine oxidase, copper containing 3 (vascular adhesion protein 1)), CTSL1 (cathepsin L1), PCNA (proliferating cell nuclear antigen), IGF2 (insulin-like growth factor 2 (somatomedin A)), ITGB1 (integrin, beta 1 (fibronectin receptor, beta polypeptide, antigen CD29 includes MDF2, MSK12)), CAST (calpastatin), CXCL12 (chemokine (C—X—C motif) ligand 12 (stromal cell-derived factor 1)), IGHE (immunoglobulin heavy constant epsilon), KCNE1 (potassium voltage-gated channel, Isk-related family, member 1), TFRC (transferrin receptor (p90, CD71)), COL1A1 (collagen, type I, alpha 1), COL1A2 (collagen, type I, alpha 2), IL2RB (interleukin 2 receptor, beta), PLA2G10 (phospholipase A2, group X), ANGPT2 (angiopoietin 2), PROCR (protein C receptor, endothelial (EPCR)), NOX4 (NADPH oxidase 4), HAMP (hepcidin antimicrobial peptide), PTPN11 (protein tyrosine phosphatase, non-receptor type 11), SLC2A1 (solute carrier family 2 (facilitated glucose transporter), member 1), IL2RA (interleukin 2 receptor, alpha), CCL5 (chemokine (C—C motif) ligand 5), IRF1 (interferon regulatory factor 1), CFLAR (CASP8 and FADD-like apoptosis regulator), CALCA (calcitonin-related polypeptide alpha), EIF4E (eukaryotic translation initiation factor 4E), GSTP1 (glutathione S-transferase pi 1), JAK2 (Janus kinase 2), CYP3A5 (cytochrome P450, family 3, subfamily A, polypeptide 5), HSPG2 (heparan sulfate proteoglycan 2), CCL3 (chemokine (C—C motif) ligand 3), MYD88 (myeloid differentiation primary response gene (88)), VIP (vasoactive intestinal peptide), SOAT1 (sterol O-acyltransferase 1), ADRBK1 (adrenergic, beta, receptor kinase 1), NR4A2 (nuclear receptor subfamily 4, group A, member 2), MMP8 (matrix metallopeptidase 8 (neutrophil collagenase)), NPR2 (natriuretic peptide receptor B/guanylate cyclase B (atrionatriuretic peptide receptor B)), GCH1 (GTP cyclohydrolase 1), EPRS (glutamyl-prolyl-tRNA synthetase), PPARGC1A (peroxisome proliferator-activated receptor gamma, coactivator 1 alpha), F12 (coagulation factor XII (Hageman factor)), PECAM1 (platelet/endothelial cell adhesion molecule), CCL4 (chemokine (C—C motif) ligand 4), SERPINA3 (serpin peptidase inhibitor, clade A (alpha-1 antiproteinase, antitrypsin), member 3), CASR (calcium-sensing receptor), GJAS (gap junction protein, alpha 5, 40 kDa), FABP2 (fatty acid binding protein 2, intestinal), TTF2 (transcription termination factor, RNA polymerase II), PROS1 (protein S (alpha)), CTF1 (cardiotrophin 1), SGCB (sarcoglycan, beta (43 kDa dystrophin-associated glycoprotein)), YME1L1 (YME1-like 1 (*S. cerevisiae*)), CAMP (cathelicidin antimicrobial peptide), ZC3H12A (zinc finger CCCH-type containing 12A), AKR1B1 (aldo-keto reductase family 1, member B1 (aldose reductase)), DES (desmin), MMPI (matrix metallopeptidase 7 (matrilysin, uterine)), AHR (aryl hydrocarbon receptor), CSF1 (colony stimulating factor 1 (macrophage)), HDAC9 (histone deacetylase 9), CTGF (connective tissue growth factor), KCNMA1 (potassium large conductance calcium-activated channel, subfamily M, alpha member 1), UGT1A (UDP glucuronosyltransferase 1 family, polypeptide A complex locus), PRKCA (protein kinase C, alpha), COMT (catechol-β-methyltransferase), S100B (S100 calcium binding protein B), EGR1 (early growth response 1), PRL (prolactin), IL15 (interleukin 15), DRD4 (dopamine receptor D4), CAMK2G (calcium/calmodulin-dependent protein kinase II gamma), SLC22A2 (solute carrier family 22 (organic cation transporter), member 2), CCL11 (chemokine (C—C motif) ligand 11), PGF (placental growth factor), THPO (thrombopoietin), GP6 (glycoprotein VI (platelet)), TACR1 (tachykinin receptor 1), NTS (neurotensin), HNF1A (HNF1 homeobox A), SST (somatostatin), KCND1 (potassium voltage-gated channel, Shal-related subfamily, member 1), LOC646627 (phospholipase inhibitor), TBXAS1 (thromboxane A synthase 1 (platelet)), CYP2J2 (cytochrome P450, family 2, subfamily J, polypeptide 2), TBXA2R (thromboxane A2 receptor), ADH1C (alcohol dehydrogenase 1C (class I), gamma polypeptide), ALOX12 (arachidonate 12-lipoxygenase), AHSG (alpha-2-HS-glycoprotein), BHMT (betaine-homocysteine methyltransferase), GJA4 (gap junction protein, alpha 4, 37 kDa), SLC25A4 (solute carrier family 25 (mitochondrial carrier; adenine nucleotide translocator), member 4), ACLY (ATP citrate lyase), ALOX5AP (arachidonate 5-lipoxygenase-activating protein), NUMA1 (nuclear mitotic apparatus protein 1), CYP27B1 (cytochrome P450, family 27, subfamily B, polypeptide 1), CYSLTR2 (cysteinyl leukotriene receptor 2), SOD3 (superoxide dismutase 3, extracellular), LTC4S (leukotriene C4 synthase), UCN (urocortin), GHRL (ghrelin/obestatin prepropeptide), APOC2 (apolipoprotein C-II), CLEC4A (C-type lectin domain family 4, member A), KBTBD10 (kelch repeat and BTB (POZ) domain containing 10), TNC (tenascin C), TYMS (thymidylate synthetase), SHC1 (SHC (Src homology 2 domain containing) transforming protein 1), LRP1 (low density lipoprotein receptor-related protein 1), SOCS3 (suppressor of cytokine signaling 3), ADH1B (alcohol dehydrogenase 1B (class I), beta polypeptide), KLK3 (kallikrein-related peptidase 3), HSD11B1 (hydroxysteroid (11-beta) dehydrogenase 1), VKORC1 (vitamin K epoxide reductase complex, subunit 1), SERPINB2 (serpin peptidase inhibitor, clade B (ovalbumin), member 2), TNS1 (tensin 1), RNF19A (ring finger protein 19A), EPOR (erythropoietin receptor), ITGAM (integrin, alpha M (complement component 3 receptor 3 subunit)), PITX2 (paired-like homeodomain 2), MAPK7 (mitogen-activated protein kinase 7), FCGR3A (Fc fragment of IgG, low affinity 111a, receptor (CD16a)), LEPR (leptin receptor), ENG (endoglin), GPX1 (glutathione peroxidase 1), GOT2 (glutamic-oxaloacetic transaminase 2, mitochondrial (aspartate aminotransferase 2)), HRH1 (histamine receptor H1), NR1I2 (nuclear receptor subfamily 1, group I, member 2), CRH (corticotropin releasing hormone), HTR1A (5-hydroxytryptamine (serotonin) receptor 1A), VDAC1 (voltage-dependent anion channel 1), HPSE (heparanase), SFTPD (surfactant protein D), TAP2 (transporter 2, ATP-binding cassette, sub-family B (MDR/TAP)), RNF123 (ring finger protein 123), PTK2B (PTK2B protein tyrosine kinase 2 beta), NTRK2 (neurotrophic tyrosine kinase, receptor, type 2), IL6R (interleukin 6 receptor), ACHE (acetylcholinesterase (Yt blood group)), GLP1R (glucagon-like peptide 1 receptor), GHR (growth hormone receptor), GSR (glutathione reductase), NQO1 (NAD(P)H dehydrogenase, quinone 1), NR5A1 (nuclear receptor subfamily 5, group A, member 1), GJB2 (gap junction protein, beta 2, 26 kDa), SLC9A1 (solute carrier family 9 (sodium/hydrogen exchanger), member 1), MAOA (monoamine oxidase A), PCSK9 (proprotein convertase subtilisin/kexin type 9), FCGR2A (Fc fragment of IgG, low affinity IIa, receptor (CD32)), SERPINF1 (serpin peptidase inhibitor, clade F (alpha-2 antiplasmin, pigment epithelium derived factor), member 1), EDN3 (endothelin 3), DHFR (dihydrofolate reductase), GAS6 (growth arrest-specific 6), SMPD1 (sphingomyelin phosphodiesterase 1, acid lysosomal), UCP2 (uncoupling protein 2 (mitochondrial, proton carrier)), TFAP2A (transcription factor AP-2 alpha (activating enhancer binding protein 2 alpha)), C4BPA (complement component 4 binding protein, alpha), SERPINF2 (serpin peptidase inhibitor, clade F (alpha-2 antiplasmin, pigment epithelium derived factor), member 2), TYMP (thymidine phosphorylase), ALPP (alkaline phosphatase, placental (Regan isozyme)), CXCR2 (chemokine (C—X—C motif) receptor 2), SLC39A3 (solute carrier family 39 (zinc transporter), member 3), ABCG2 (ATP-binding cassette, sub-family G (WHITE), member 2), ADA (adenosine deaminase), JAK3 (Janus kinase 3), HSPA1A (heat shock 70 kDa protein 1A), FASN (fatty acid synthase), FGF1 (fibroblast growth factor 1 (acidic)), F11 (coagulation factor XI), ATP7A (ATPase, Cu++ transporting, alpha polypeptide), CR1 (complement component (3b/4b) receptor 1 (Knops blood group)), GFAP (glial fibrillary acidic protein), ROCK1 (Rho-associated, coiled-coil containing protein kinase 1), MECP2 (methyl CpG binding protein 2 (Rett syndrome)), MYLK (myosin light chain kinase), BCHE (butyrylcholinesterase), LIPE (lipase, hormone-sensitive), PRDX5 (peroxiredoxin 5), ADORA1 (adenosine A1 receptor), WRN (Werner syndrome, RecQ helicase-like), CXCR3 (chemokine (C—X—C motif) receptor 3), CD81 (CD81 molecule), SMAD7 (SMAD family member 7), LAMC2 (laminin, gamma 2), MAP3K5 (mitogen-activated protein kinase kinase kinase 5), CHGA (chromogranin A (parathyroid secretory protein 1)), IAPP (islet amyloid polypeptide), RHO (rhodopsin), ENPP1 (ectonucleotide pyrophosphatase/phosphodiesterase 1), PTHLH (parathyroid hormone-like hormone), NRG1 (neuregulin 1), VEGFC (vascular endothelial growth factor C), ENPEP (glutamyl aminopeptidase (aminopeptidase A)), CEBPB (CCAAT/enhancer binding protein (C/EBP), beta), NAGLU (N-acetylglucosaminidase, alpha), F2RL3 (coagulation factor II (thrombin) receptor-like 3), CX3CL1 (chemokine (C—X3-C motif) ligand 1), BDKRB1 (bradykinin receptor B1), ADAMTS13 (ADAM metallopeptidase with thrombospondin type 1 motif, 13), ELANE (elastase, neutrophil expressed), ENPP2 (ectonucleotide pyrophosphatase/phosphodiesterase 2), CISH (cytokine inducible SH2-containing protein), GAST (gastrin), MYOC (myocilin, trabecular meshwork inducible glucocorticoid response), ATP1A2 (ATPase, Na+/K+ transporting, alpha 2 polypeptide), NF1 (neurofibromin 1), GJB1 (gap junction protein, beta 1, 32 kDa), MEF2A (myocyte enhancer factor 2A), VCL (vinculin), BMPR2 (bone morphogenetic protein receptor, type II (serine/threonine kinase)), TUBB (tubulin, beta), CDC42 (cell division cycle 42 (GTP binding protein, 25 kDa)), KRT18 (keratin 18), HSF1 (heat shock transcription factor 1), MYB (v-myb myeloblastosis viral oncogene homolog (avian)), PRKAA2 (protein kinase, AMP-activated, alpha 2 catalytic subunit), ROCK2 (Rho-associated, coiled-coil containing protein kinase 2), TFPI (tissue factor pathway inhibitor (lipoprotein-associated coagulation inhibitor)), PRKG1 (protein kinase, cGMP-dependent, type I), BMP2 (bone morphogenetic protein 2), CTNND1 (catenin (cadherin-associated protein), delta 1), CTH (cystathionase (cystathionine gamma-lyase)), CTSS (cathepsin S), VAV2 (vav 2 guanine nucleotide exchange factor), NPY2R (neuropeptide Y receptor Y2), IGFBP2 (insulin-like growth factor binding protein 2, 36 kDa), CD28 (CD28 molecule), GSTA1 (glutathione S-transferase alpha 1), PPIA (peptidylprolyl isomerase A (cyclophilin A)), APOH (apolipoprotein H (beta-2-glycoprotein I)), S100A8 (S100 calcium binding protein A8), IL11 (interleukin 11), ALOX15 (arachidonate 15-lipoxygenase), FBLN1 (fibulin 1), NR1H3 (nuclear receptor subfamily 1, group H, member 3), SCD (stearoyl-CoA desaturase (delta-9-desaturase)), GIP (gastric inhibitory polypeptide), CHGB (chromogranin B (secretogranin 1)), PRKCB (protein kinase C, beta), SRD5A1 (steroid-5-alpha-reductase, alpha polypeptide 1 (3-oxo-5 alpha-steroid delta 4-dehydrogenase alpha 1)), HSD11B2 (hydroxysteroid (11-beta) dehydrogenase 2), CALCRL (calcitonin receptor-like), GALNT2 (UDP-N-acetyl-alpha-D-galactosamine-polypeptide N-acetylgalactosaminyltransferase 2 (GalNAc-T2)), ANGPTL4 (angiopoietin-like 4), KCNN4 (potassium intermediate/small conductance calcium-activated channel, subfamily N, member 4), PIK3C2A (phosphoinositide-3-kinase, class 2, alpha polypeptide), HBEGF (heparin-binding EGF-like growth factor), CYP7A1 (cytochrome P450, family 7, subfamily A, polypeptide 1), HLA-DRB5 (major histocompatibility complex, class II, DR beta 5), BNIP3 (BCL2/adenovirus E1B 19 kDa interacting protein 3), GCKR (glucokinase (hexokinase 4) regulator), S100A12 (S100 calcium binding protein A12), PADI4 (peptidyl arginine deaminase, type IV), HSPA14 (heat shock 70 kDa protein 14), CXCR1 (chemokine (C—X—C motif) receptor 1), H19 (H19, imprinted maternally expressed transcript (non-protein coding)), KRTAP19-3 (keratin associated protein 19-3), insulin, RAC2 (ras-related C3 botulinum toxin substrate 2 (rho family, small GTP binding protein Rac2)), RYR1 (ryanodine receptor 1 (skeletal)), CLOCK (clock homolog (mouse)), NGFR (nerve growth factor receptor (TNFR superfamily, member 16)), DBH (dopamine beta-hydroxylase (dopamine beta-monooxygenase)), CHRNA4 (cholinergic receptor, nicotinic, alpha 4), CACNA1C (calcium channel, voltage-dependent, L type, alpha 1C subunit), PRKAG2 (protein kinase, AMP-activated, gamma 2 non-catalytic subunit), CHAT (choline acetyltransferase), PTGDS (prostaglandin D2 synthase 21 kDa (brain)), NR1H2 (nuclear receptor subfamily 1, group H, member 2), TEK (TEK tyrosine kinase, endothelial), VEGFB (vascular endothelial growth factor B), MEF2C (myocyte enhancer factor 2C), MAPKAPK2 (mitogen-activated protein kinase-activated protein kinase 2), TNFRSF11A (tumor necrosis factor receptor superfamily, member 11a, NFKB activator), HSPA9 (heat shock 70 kDa protein 9 (mortalin)), CYSLTR1 (cysteinyl leukotriene receptor 1), MAT1A (methionine adenosyltransferase I, alpha), OPRL1 (opiate receptor-like 1), IMPA1 (inositol(myo)-1(or 4)-monophosphatase 1), CLCN2 (chloride channel 2), DLD (dihydrolipoamide dehydrogenase), PSMA6 (proteasome (prosome, macropain) subunit, alpha type, 6), PSMB8 (proteasome (prosome, macropain) subunit, beta type, 8 (large multifunctional peptidase 7)), CHI3L1 (chitinase 3-like 1 (cartilage glycoprotein-39)), ALDH1B1 (aldehyde dehydrogenase 1 family, member B1), PARP2 (poly (ADP-ribose) polymerase 2), STAR (steroidogenic acute regulatory protein), LBP (lipopolysaccharide binding protein), ABCC6 (ATP-binding cassette, sub-family C(CFTR/MRP), member 6), RGS2 (regulator of G-protein signaling 2, 24 kDa), EFNB2 (ephrin-B2), cystic fibrosis transmembrane conductance regulator (CFTR), GJB6 (gap junction protein, beta 6, 30 kDa), APOA2 (apolipoprotein A-II), AMPD1 (adenosine monophosphate deaminase 1), DYSF (dysferlin, limb girdle muscular dystrophy 2B (autosomal recessive)), FDFT1 (farnesyl-diphosphate farnesyltransferase 1), EDN2 (endothelin 2), CCR6 (chemokine (C—C motif) receptor 6), GJB3 (gap junction protein, beta 3, 31 kDa), IL1RL1 (interleukin 1 receptor-like 1), ENTPD1 (ectonucleoside triphosphate diphosphohydrolase 1), BBS4 (Bardet-Biedl syndrome 4), CELSR2 (cadherin, EGF LAG seven-pass G-type receptor 2 (flamingo homolog, Drosophila)), F11R (F11 receptor), RAPGEF3 (Rap guanine nucleotide exchange factor (GEF) 3), HYAL1 (hyaluronoglucosaminidase 1), ZNF259 (zinc finger protein 259), ATOX1 (ATX1 antioxidant protein 1 homolog (yeast)), ATF6 (activating transcription factor 6), KHK (ketohexokinase (fructokinase)), SAT1 (spermidine/spermine N1-acetyltransferase 1), GGH (gamma-glutamyl hydrolase (conjugase, folylpolygammaglutamyl hydrolase)), TIMP4 (TIMP metallopeptidase inhibitor 4), SLC4A4 (solute carrier family 4, sodium bicarbonate cotransporter, member 4), PDE2A (phosphodiesterase 2A, cGMP-stimulated), PDE3B (phosphodiesterase 3B, cGMP-inhibited), FADS1 (fatty acid desaturase 1), FADS2 (fatty acid desaturase 2), TMSB4X (thymosin beta 4, X-linked), TXNIP (thioredoxin interacting protein), LIMS1 (LIM and senescent cell antigen-like domains 1), RHOB (ras homolog gene family, member B), LY96 (lymphocyte antigen 96), FOXO1 (forkhead box O1), PNPLA2 (patatin-like phospholipase domain containing 2), TRH (thyrotropin-releasing hormone), GJC1 (gap junction protein, gamma 1, 45 kDa), SLC17A5 (solute carrier family 17 (anion/sugar transporter), member 5), FTO (fat mass and obesity associated), GJD2 (gap junction protein, delta 2, 36 kDa), PSRC1 (proline/serine-rich coiled-coil 1), CASP12 (caspase 12 (gene/pseudogene)), GPBAR1 (G protein-coupled bile acid receptor 1), PXK (PX domain containing serine/threonine kinase), IL33 (interleukin 33), TRIB1 (tribbles homolog 1 (Drosophila)), PBX4 (pre-B-cell leukemia homeobox 4), NUPR1 (nuclear protein, transcriptional regulator, 1), 15-Sep(15 kDa selenoprotein), CILP2 (cartilage intermediate layer protein 2), TERC (telomerase RNA component), GGT2 (gamma-glutamyltransferase 2), MT-CO1 (mitochondrially encoded cytochrome c oxidase I), UOX (urate oxidase, pseudogene), a CRISPR/Cas effector polypeptide, an enzymatically active CRISPR/Cas effector polypeptide (e.g., is capable of cleaving a target nucleic acid). and a CRISPR/Cas effector polypeptide that is not enzymatically active (e.g., does not cleave a target nucleic acid, but retains binding to the target nucleic acid). In some cases, the donor DNA encodes a wild-type version of any of the foregoing polypeptides; i.e., the donor DNA can encode a "normal" version that does not include a mutation(s) that results in reduced function, lack of function, or pathogenesis.

In some cases, the donor DNA comprises a nucleotide sequence encoding a fluorescent polypeptide. Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilized EGFP (dEGFP), destabilized ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2 (12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, can be encoded.

In some cases, the donor DNA encodes an RNA, e.g., an siRNA, a microRNA, a short hairpin RNA (shRNA), an anti-sense RNA, a riboswitch, a ribozyme, an aptamer, a ribosomal RNA, a transfer RNA, and the like.

A donor DNA can include, in addition to a nucleotide sequence encoding one or more gene products (e.g., an RNA and/or a polypeptide), one or more transcriptional control elements, e.g., a promoter, an enhancer, and the like. In some cases, the transcriptional control element is inducible. In some cases, the promoter is reversible. In some cases, the transcriptional control element is constitutive. In some cases, the promoter is functional in a eukaryotic cell. In some cases, the promoter is a cell type-specific promoter. In some cases, the promoter is a tissue-specific promoter.

The nucleotide sequence of the donor DNA is typically not identical to the target nucleic acid (e.g., genomic sequence) that it replaces. Rather, the donor DNA may contain at least one or more single base changes, insertions, deletions, inversions or rearrangements with respect to the target nucleic acid (e.g., genomic sequence), so long as sufficient homology is present to support homology-directed repair (e.g., for gene correction, e.g., to convert a disease-causing base pair or a non-disease-causing base pair). In some cases, the donor DNA comprises a non-homologous sequence flanked by two regions of homology, such that homology-directed repair between the target DNA region and the two flanking sequences results in insertion of the non-homologous sequence at the target region. Donor DNA may also comprise a vector backbone containing sequences that are not homologous to the DNA region of interest (the target nucleic acid) and that are not intended for insertion into the DNA region of interest (the target nucleic acid). Generally, the homologous region(s) of a donor sequence will have at least 50% sequence identity to a target nucleic acid (e.g., a genomic sequence) with which recombination is desired. In certain cases, 60%, 70%, 80%, 90%, 95%, 98%, 99%, or 99.9% sequence identity is present. Any value between 1% and 100% sequence identity can be present, depending upon the length of the donor polynucleotide.

The donor DNA may comprise certain nucleotide sequence differences as compared to the target nucleic acid (e.g., genomic sequence), where such difference include, e.g. restriction sites, nucleotide polymorphisms, selectable markers (e.g., drug resistance genes, fluorescent proteins, enzymes etc.), etc., which may be used to assess for successful insertion of the donor DNA at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence. In some cases, the donor DNA will include one or more nucleotide sequences to aid in localization of the donor to the nucleus of the recipient cell or to aid in the integration of the donor DNA into the target nucleic acid. For example, in some case, the donor DNA may comprise one or more nucleotide sequences encoding one or more nuclear localization signals (e.g. PKKKRKV (SEQ ID NO:1), VSRKRPRP (SEQ ID NO:2), QRKRKQ (SEQ ID NO:3), and the like (Frietas et al (2009) Curr Genomics 10:550-7). In some cases, the donor DNA will include nucleotide sequences to recruit DNA repair enzymes to increase insertion efficiency. Human enzymes involved in homology directed repair include MRN-Ct1P, BLM-DNA2, Exo1, ERCC1, Rad51, Rad52, Ligase 1, PolΘ, PARP1, Ligase 3, BRCA2, RecQ/BLM-TopoIIIα, RTEL, Polδ, and Polη (Verma and Greenburg (2016) *Genes Dev.* 30 (10): 1138-1154). In some cases, the donor DNA is delivered as reconstituted chromatin (Cruz-Becerra and Kadonaga (2020) eLife 2020;9:e55780 DOI: 10.7554/eLife.55780).

In some cases, the ends of the donor DNA are protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and 0-methyl ribose or deoxyribose residues. As an alternative to protecting the termini of a linear donor DNA, additional lengths of sequence may be included outside of the regions of homology that can be degraded without impacting recombination.

Generating Nanostructures

DNA origami structures incorporate DNA as a building material to make nanoscale shapes. The DNA origami process can involve the folding of one or more long, “scaffold” DNA strands (e.g., a single-stranded linear donor DNA) into a particular shape using a plurality of rationally designed “staple” DNA strands (“staple oligonucleotides” or “staple nucleic acids”). The sequences of the staple strands can be designed such that they hybridize to particular portions of the scaffold strands and, in doing so, force the scaffold strands into a particular shape. The DNA origami can include a scaffold strand and a plurality of rationally designed staple strands. The scaffold strand can have any sufficiently non-repetitive sequence.

As noted above, staple oligonucleotides are designed to fold the linear single-stranded donor DNA into a two-dimensional or three-dimensional nanostructure. In some cases, the staple oligonucleotides are selected such that the DNA nanostructure is planar. In some cases, the staple oligonucleotides are selected such that the DNA nanostructure is substantially barrel- or tube-shaped. The staples oligonucleotides are selected such that the barrel shape is closed at both ends or is open at one or both ends. In certain cases, the barrel shape of the DNA nanostructure can be a hexagonal tube. In some cases, the staple oligonucleotides are designed to fold the linear single-stranded donor DNA into a nanostructure comprising parallel helices. In some cases, the staple oligonucleotides are designed to fold the linear single-stranded donor DNA into a two-dimensional or 3-dimensional polygonal network wherein the edges of the network are comprised of blocks of at least two parallel helices. In some cases, the staple oligonucleotides are designed to fold the linear single-stranded donor DNA into a 6-helix nanostructure. In some cases, the staple oligonucleotides are designed to fold the linear single-stranded donor DNA into a 24-helix nanostructure.

Methods useful in making DNA nanostructures can be found, for example, in Rothemund (2006) *Nature* 440:297-302; Castro et al. (2011) *Nat. Methods* 8:221; Douglas et al. (2009) *Nature* 459:414-418; Dietz et al. (2009) *Science* 325:725-730; and U.S. Pat. App. Pub. Nos. 2007/0117109, 2008/0287668, 2010/0069621, 2015/0329584, and 2010/0216978, each of which is incorporated by reference in its entirety. Staple design can be facilitated using, for example, CADnano software, available on the internet at www(dot) cadnano(dot)org. Once the staple oligonucleotides are designed, they are synthesized, mixed with the linear single-stranded donor DNA in a buffer solution, heated (for example to about 90 degrees Celsius), then cooled to room temperature. The buffer solution is selected to allow for hybridization of the linear single-stranded donor DNA with the staple oligonucleotides. In some cases, the buffer comprises magnesium. Generally, a stoichiometric excess of the staple oligonucleotides is used. As one non-limiting example, 10-100 times as many staple oligonucleotide molecules are present as would be needed to fold all the linear single-stranded donor DNA molecules.

The DNA nanostructures can be purified to remove excess staple oligonucleotides and/or to remove unfolded DNA. Purification can be carried out using, e.g., gel electrophoresis. In some cases, a DNA nanostructure present in a composition of the present disclosure is at least 50% pure, at least 60% pure, at least 70% pure, at least 80% pure, at least 90% pure, at least 95% pure, at least 98% pure, or at least 99% pure.

DNA Nanostructures

The present disclosure provides a composition comprising: a) a gene editing polypeptide or a gene-editing system (e.g., a gene-editing system comprising a CRISPR/Cas effector polypeptide and a guide nucleic acid); and b) a DNA nanostructure formed by hybridizing a linear single-stranded donor DNA with one or more staple oligonucleotides, i.e., a DNA nanostructure comprising a donor DNA and at least one staple oligonucleotide, where the donor DNA comprises a first homology arm and a second homology arm that are in proximity to one another by virtue of the folding of the donor DNA induced by the staple oligonucleotide(s). The first and second homology arms are single-stranded and are located at or near the 5' and the 3' ends, respectively, of the DNA nanostructure. As described above, the donor DNA comprises a nucleotide sequence of interest between the first and second homology arms.

The first and the second homology arms are brought into proximity to one another in the nanostructure formed by hybridization of the single-stranded donor DNA with the one or more staple oligonucleotides, relative to their positions in the linear single-stranded donor DNA (donor DNA not hybridized with the one or more staple oligonucleotides). For example, the distance between the first and the second homology arms can be from about 5 nm to about 150 nm from one another; e.g., from about 5 nm to about 10 nm, from about 10 nm to about 20 nm, from about 20 nm to about 25 nm, from about 25 nm to about 50 nm, from about 50 nm to about 75 nm, from about 75 nm to about 100 nm, from about 100 nm to about 110 nm, from about 110 nm to about 120 nm, from about 120 nm to about 130 nm, from about 130 nm to about 140 nm, or from about 140 nm to about 150 nm.

Thus, the DNA nanostructure includes: a) a donor DNA comprising: i) a first homology arm having a length of from about 10 nucleotides to 400 nucleotides; ii) a nucleotide sequence of interest; and iii) a second homology arm having a length of from about 10 nucleotides to 400 nucleotides; and b) one or more staple oligonucleotides hybridized to the donor DNA at one or more sites between the first and the second homology arms; where donor DNA that is between the first and the second homology arms (the "nucleotide sequence of interest") is folded by virtue of hybridization of the one or more staple oligonucleotides such that the folded structure has a length of from about 5 nm to about 500 nm; e.g., from about 5 nm to about 10 nm, from about 10 nm to about 20 nm, from about 20 nm to about 25 nm, from about 25 nm to about 50 nm, from about 50 nm to about 75 nm, from about 75 nm to about 100 nm, from about 100 nm to about 110 nm, from about 110 nm to about 120 nm, from about 120 nm to about 130 nm, from about 130 nm to about 140 nm, from about 140 nm to about 150 nm, from about 150 nm to about 175 from about, from about 175 from about to about 200 nm, from about 200 nm to about 225 nm, from about 225 nm to about 250 nm, from about 250 nm to about 275 nm, from about 275 nm to about 300 nm, from about 300 nm to about 325 nm, from about 325 nm to about 350 nm, from about 350 nm to about 375 nm, from about 375 nm to about 400 nm, from about 400 nm to about 425 nm, from about 425 nm to about 450 nm, from about 450 nm to about 475 nm, or from about 475 nm to 500 nm. In some cases, the folded structure has a length of from about 5 nm to about 150 nm. In some cases, the folded structure has a length of from about 25 nm to about 150 nm. In some cases, the folded structure has a length of from about 50 nm to about 150 nm.

In some cases, the DNA nanostructure is a 6-helix bundle. In some cases, the DNA nanostructure is a 24-helix bundle. In some cases, the DNA nanostructure is cuboid. In some cases, the DNA nanostructure is a cylinder, i.e., is cylindrical in shape. In some cases, a DNA nanostructure is a multilayer DNA nanostructure. In some cases, the multilayer DNA nanostructure is a honeycomb lattice. In some cases, the multilayer DNA nanostructure is a square lattice. In some cases, the multilayer DNA nanostructure will incorporate curvature. In some cases, some parts of the DNA nanostructure will remain single stranded and will not include staples (will not have staple oligonucleotides hybridized to the DNA), to allow for flexibility.

In some cases, the DNA nanostructure is described based on the number of helices formed in an X direction, the number of helices formed in a Y direction, and a depth of such helices (indicated by the length in bases of such helices). For example, a cuboid shape comprising 3 helices in the X direction and 3 helices in the Y direction, where each helix has a length of 32 bases, would be described as "3H×3H (×32b). Helices so formed may be discontinuous. The DNA nanostructure can be any of a variety of sizes and shapes, including cuboids such as 3H×3H (×32b, ×64b, ×128b, ×256b, ×512b, or ×1024b); 4H×4H (×32b, ×64b, ×128b, ×256b, or ×512b), 12H×12H (×48b). The DNA nanostructure can be a cylinder such as 6H×10H (×32b, ×64b, or ×128b). The DNA nanostructure can be a honeycomb lattice such as 6H×6H (×84b). See, e.g., US 2015/0218204.

In some cases, the DNA nanostructure serves as a carrier for an agent (also referred to as a "payload") such as a small molecule, an RNA, a polypeptide, or a ligand for a receptor. The agent can be a therapeutic agent. The agent can be a labeling agent (e.g., an imaging agent). In some cases, the payload is a small molecule, e.g., a cytotoxic anti-cancer agent, an anti-angiogenic agent, and the like. The payload can be a polypeptide, e.g., an anti-angiogenic polypeptide, an immunotherapeutic agent (e.g., a chimeric antigen receptor; a therapeutic antibody), an antibody (e.g., a single-chain Fv, a nanobody, etc.), and the like. The payload can be a peptide hormone, a growth factor, and the like. The payload can be non-covalently associated with the DNA nanostructure. The payload can be covalently linked to the DNA nanostructure. In some cases, a targeting moiety (e.g., an antibody) is covalently linked to the DNA nanostructure.

In some cases, the payload is a DNA-dependent protein kinase (DNA-PK) inhibitor. In some cases, the DNA-PK inhibitor is selected from NU7441 (8-(4-Dibenzothienyl)-2-(4-morpholinyl)-4H-1-benzopyran-4-one), M3814 (S)-(2-chloro-4-fluoro-5-(7-morpholinoquinazolin-4-yl)phenyl)(6-met-hoxypyridazin-3-yl)methanol, NU 7026 (2-(4-morpholinyl)-4H-naphthol[1,2-b]pyran-4-one), compound 401 (2-(4-morpholinyl)-4H-pyrimido[2,1-a]isoquinolin-4-one), PI 103 hydrochloride (3-[4-(4-morpholinylpyrido[3',2':4,5]furo[3,2-d]pyrimidin-2-yl]phenol hydrochloride); DMNB (4,5-dimethoxy-2-nitrobenzaldehyde); ETP 45658 (3-[1-methyl-4-(4-morpholinyl)-1H-pyrazolo[3,4-d]pyrimidin-6-ylphenol), KU 0060648 (4-ethyl-N-[4-[2-(4-morpholinyl)-4-oxo-4H-1-benzopyran-8-yl]-1-dibenzothienyl]-1-piperazineacetamide), LTURM 34 (8-(4-dibenzothienyl1)-2-(4-morpholinyl)-4H-1,3-benzoxazin-4-one), 1-(2-hydroxy-4-morpholin-4-yl-phenyl)-ethanone; PIK-75 HCl (2-methyl-5-nitro-2-R6-bromoimidazo[1,2-a]pyridin-3-yl)methylene]-1-meth-ylhydrazide-benzenesulfonic acid, monohydrochloride); and CC-115 (1-ethyl-7-(2-methyl-6-(1h-1,2,4-triazol-3-yl)pyridin-3-yl)-3,4-dihydropy-razino(2,3-b)pyrazin-2(1h)-one).

In some cases, the payload is a small molecule inhibitor that modulates DNA repair pathways (e.g. NU7441 (KU-57788) and KU-0060648 that pharmacologically inhibit non homologous end joining pathways). NU7441 has the following structure:

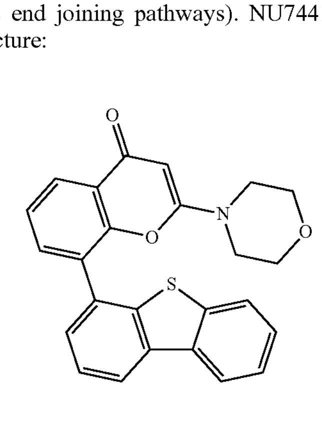

KU-0060648 has the following structure:

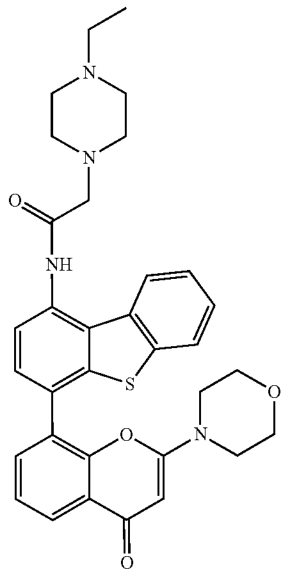 [SMILES: CCN1CCN(CC(=O)Nc2ccc(-c3cccc4c(=O)cc(N5CCOCC5)oc34)c3sc4ccccc4c23)CC1]

The payload can be an effector polypeptide. Non-limiting examples of suitable effector polypeptides include adrenocorticotropic hormone (ACTH), amylin, angiopoietin-1, angiopoietin-2, angiotensin, atrial natriuretic peptide (ANP), bone-derived growth factor (BDGF), bone morphogenic protein (BMP) (e.g., BMP-2, BMP-4, BMP-7), brain-derived neurotrophic factor (BDNF), calcitonin, cartilage-derived growth factor (CDGF), cholecystokinin, ephrin B2 (EphB2), epidermal growth factor (EGF), erythropoietin, fibroblast growth factor (FGF), FGF-2, FGF-19, FGF-3, FGF-8, follicle stimulating hormone (FSH), gastrin, glial fibrillary acidic protein (GFAP), glucagon, granulocyte colony stimulating factor (G-CSF), granulocyte-macrophage colony stimulating factor (GM-CSF), ghrelin, hematopoietic growth factor, hepatocyte growth factor (HGF), insulin, insulin-like growth factor (IGF1), an interleukin (IL) (e.g., IL-1, IL-1, IL-4, IL-5, IL-6, IL-8, IL-9, IL-10, IL-12, IL-13, IL-15, IL-18, IL-23), an interferon (IFN) (e.g., IFN-α, IFN-β, IFN-γ), keratinocyte growth factor, leptin, leuteinizing hormone, macrophage inflammatory peptide MIP-1a, macrophage inflammatory peptide MIP-1b, macrophage colony stimulating factor (M-CSF), macrophage chemoattractant and activating factor (MCAF), melanocyte-stimulating hormone (MSH), nerve growth factor (NGF), neural epidermal growth factor-like-1 (NELL1), neurotrophin-3 (NT-3), neurotrophin-4 (NT-4), neuronal growth factor, neutrophil activating protein (NAP), a Notch polypeptide (e.g., Notch-1, Notch-2, Notch-3, Notch-4), oxytocin, parathyroid hormone, parathyroid hormone-related peptide (PTHrP), placental growth factor, platelet derived growth factor (PDGF), prolactin, RANTES, relaxin, renin, resistin, skeletal growth factor (SGF), somatostatin, stromal derived growth factor 1 (SDF-1), thyroid stimulating hormone (TSH), thyrotropin-releasing hormone, transforming growth factor (TGF)-β1, TGF-β2, TGF-β3, TGF-β4, TGF-β5, tumor necrosis factor (TNF), thrombopoietin, vascular endothelial growth factor (VEGF), vasopressin, vasoactive intestinal peptide, a Wnt polypeptide (e.g., Wnt1, Wnt2, Wnt2b (also called Wnt13), Wnt3, Wnt3a, Wnt4, Wnt5a, Wnt5b, Wnt6, Wnt7a, Wnt7b, Wnt7c, Wnt8, Wnt8a, Wnt8b, Wnt5c, Wnt10a, Wnt10b, Wnt11, Wnt14, Wnt15, or Wnt16), and the like.

In some cases, the payload is a nucleic acid payload (e.g., a DNA and/or RNA). The nucleic acid payload can be any nucleic acid of interest, e.g., the nucleic acid payload can be linear or circular, and can be a plasmid, a viral genome, an RNA (e.g., a coding RNA such as an mRNA or a non-coding RNA such as a guide RNA, a short interfering RNA (siRNA), a short hairpin RNA (shRNA), a microRNA (miRNA), and the like), a DNA, etc. In some cases, the payload is an mRNA encoding an antigen that is used to elicit an immune response (e.g., a vaccine). In some cases, the nucleic payload is an RNAi agent (e.g., an shRNA, an siRNA, a miRNA, etc.) or a DNA template encoding an RNAi agent. In some cases, the nucleic acid payload is an siRNA molecule (e.g., one that targets an mRNA, one that targets a miRNA). In some cases, the nucleic acid payload is an LNA molecule (e.g., one that targets a miRNA). In some cases, the nucleic acid payload is a miRNA. In some cases, the nucleic acid payload includes an mRNA that encodes a protein of interest. A nucleic acid payload can include one or more of: a modified backbone, a modified sugar, and a modified base.

Compositions

The present disclosure provides a composition comprising: a) a gene-editing polypeptide; b) a single-stranded donor DNA comprising: i) a first homology arm at or near the 5' end of the donor DNA, wherein the first homology arm comprises a nucleotide sequence that is at least partially complementary to a first nucleotide sequence in a target nucleic acid; and ii) a second homology arm at or near the 3' end of the donor DNA, wherein the second homology arm comprises a nucleotide sequence that is at least partially complementary to a second nucleotide sequence in the target nucleic acid; c) one or more staple oligonucleotides, wherein the one or more staple oligonucleotides are least partially complementary to the donor DNA such that the one or more staple oligonucleotides hybridize to donor DNA, such that the donor DNA template folds into a nanostructure in which the first homology arm and the second homology arm are brought into proximity to one another. In some cases, where the gene-editing polypeptide is a CRISPR/Cas effector polypeptide, the composition further comprises a guide RNA. The present disclosure provides a composition comprising: a) a gene-editing polypeptide; and b) a DNA nanostructure formed by hybridizing a linear single-stranded donor DNA with the one or more staple oligonucleotides, i.e., a DNA nanostructure comprising a donor DNA and at least one staple oligonucleotide, where the donor DNA comprises a first homology arm and a second homology arm that are in proximity to one another by virtue of the folding of the donor DNA induced by the staple oligonucleotide(s). In some cases, where the gene-editing polypeptide is a CRISPR/Cas effector polypeptide, the composition further comprises a guide RNA.

A composition of the present disclosure may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A composition of the present disclosure can include: a) components as described above (e.g.: i) a single-stranded donor DNA comprising homology arms; a gene-editing polypeptide; and one or more staple oligonucleotides; or ii) a DNA nanostructure, as described above; and a gene-editing polypeptide); and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris (hydroxymethyl)methane (BIS-Tris), N-(2-hydroxyethyl) piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris (hydroxymethyl)-aminomethane (Tris), etc.). Suitable salts include, e.g., NaCl, $MgCl_2$, KCl, $MgSO_4$, etc.

In some cases, the composition is sterile. In some cases, the composition is suitable for administration to a human subject, e.g., where the composition is sterile and is free of detectable pyrogens and/or other toxins.

A composition of the present disclosure may include other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like. In some cases, a composition of the present disclosure comprises saline.

In some cases, the components of a composition of the present disclosure are present in a particle, or associated with a particle. The terms "particle" and "nanoparticle" can be used interchangeably, as appropriate. For example, in some cases, a composition of the present disclosure comprises a lipid and/or a hydrophilic polymer. For example, in some cases, a composition of the present disclosure comprises a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the composition further comprises cholesterol.

The components of a composition of the present disclosure can be present in a biodegradable core-shell structured nanoparticle with a poly (β-amino ester) (PBAE) core enveloped by a phospholipid bilayer shell. In some cases, particles/nanoparticles based on self-assembling bioadhesive polymers are used; such particles/nanoparticles may be applied to oral delivery. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also suitable for inclusion in a composition of the present disclosure. In one aspect, aminoalcohol lipidoid compounds are combined with components of a composition of the present disclosure to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A composition of the present disclosure can include poly(beta-amino alcohol) (PBAA). US Patent Publication No. 20130302401 relates to a class of poly(beta-amino alcohols) (PBAAs) that has been prepared using combinatorial polymerization. Sugar-based particles may be used, for example GalNAc, as described with reference to WO2014118272 (incorporated herein by reference) and Nair, J K et al., 2014, Journal of the American Chemical Society 136 (49), 16958-16961) can be included in a composition of the present disclosure.

In some cases, components of a composition of the present disclosure are included in lipid nanoparticles (LNPs). Examples of suitable cationic lipids that can be included in a composition of the present disclosure include, e.g.: 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)[1,3]-dioxolane (DLinKC2-DMA). Preparation of LNPs is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) can be used. Components of a composition of the present disclosure can be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used. See, e.g., Cutler et al., J. Am. Chem. Soc. 2011 133:9254-9257, Hao et al., Small 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in encapsulating the components of a composition of the present disclosure have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, suitable nanoparticles have a diameter of from 25 nm to 200 nm. In some cases, suitable nanoparticles have a diameter of 100 nm or less. In some cases, suitable nanoparticles have a diameter of from 35 nm to 60 nm.

Nanoparticles may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure. Semi-solid and soft nanoparticles are also suitable for use. A prototype nanoparticle of semi-solid nature is the liposome.

In some cases, components of a composition of the present disclosure are encapsulated in a liposome. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), and cholesterol. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA).

Other cationic lipids, such as amino lipid 2,2-dilinoleyl-4-dimethylaminoethyl[1,3]-dioxolane (DLin-KC2-DMA) can be included in a composition of the present disclosure. A preformed vesicle with the following lipid composition may be contemplated amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+-.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with components of a composition of the present disclosure to form lipid nanoparticles (LNPs). Suitable lipids include, but are not limited to, DLin-KC2-DMA4, C12-200 and colipids disteroylphosphatidyl choline, cholesterol, and PEG-DMG. The component molar ratio may be about 50/10/38.5/1.5 (DLin-KC2-DMA or C12-200/disteroylphosphatidyl choline/cholesterol/PEG-DMG).

Components of a composition of the present disclosure can be encapsulated in PLGA microspheres such as that further described in US published applications 20130252281 and 20130245107 and 20130244279.

Supercharged proteins can be included in a composition of the present disclosure. Supercharged proteins are a class of engineered or naturally occurring proteins with unusually high positive or negative net theoretical charge. Both supernegatively and superpositively charged proteins exhibit the ability to withstand thermally- or chemically-induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo.

Cell Penetrating Peptides (CPPs) can be included in a composition of the present disclosure. CPPs typically have an amino acid composition that either contains a high relative abundance of positively charged amino acids such as lysine or arginine or has sequences that contain an alternating pattern of polar/charged amino acids and non-polar, hydrophobic amino acids.

A composition of the present disclosure can be present in a virus-like particle (VLP), e.g., as described in WO 2020/102709. For example, a composition of the present disclosure can include a lentiviral matrix (MA) polypeptide, a lentiviral capsid (CA) polypeptide, and a lentiviral nucleocapsid (NC) polypeptide.

Gene-Editing Systems

Suitable gene-editing systems include: i) a clustered regularly interspaced short palindromic repeats (CRISPR) associated (Cas) effector polypeptide and a guide nucleic acid; ii) a zinc finger nuclease (ZFN); iii) a transcription activator-like effector nuclease (TALEN); and iv) a meganuclease (e.g., an engineered meganuclease).

Zinc Finger Nucleases (ZFNs)

In some cases, the gene-editing system comprises a zinc-finger nuclease (ZFN). ZFNs are engineered double-strand break inducing proteins comprised of a zinc finger DNA binding domain and a double strand break inducing agent domain Engineered ZFNs consist of two zinc finger arrays (ZFAs), each of which is fused to a single subunit of a non-specific endonuclease, such as the nuclease domain from the FokI enzyme, which becomes active upon dimerization. Typically, a single ZFA consists of 3 to 5 zinc finger domains, each of which is designed to recognize a specific nucleotide triplet (GGC, GAT, etc.). Thus, ZFNs composed of two "3-finger" ZFAs are capable of recognizing 18 base pairs of target sequence; 18 base pairs of recognition sequence is generally unique, even within large genomes such as those of humans and plants. By directing the co-localization and dimerization of two FokI nuclease monomers, ZFNs generate a functional site-specific endonuclease that creates a double-stranded break (DSB) in DNA at the targeted locus.

Useful zinc-finger nucleases include those that are known and those that are engineered to have specificity for one or more desired target sites (TS). Zinc finger domains are amenable for designing polypeptides which specifically bind a selected polynucleotide recognition sequence, for example, within the target site of the host cell genome. ZFNs consist of an engineered DNA-binding zinc finger domain linked to a non-specific endonuclease domain, for example nuclease domain from a Type IIs endonuclease such as HO or FokI. Alternatively, engineered zinc finger DNA binding domains can be fused to other double-strand break inducing agents or derivatives thereof that retain DNA nicking/cleaving activity. For example, this type of fusion can be used to direct the double-strand break inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, or a derivative thereof that retains DNA nicking and/or cleaving activity. Additional functionalities can be fused to the zinc-finger binding domain, including transcriptional activator domains, transcription repressor domains, and methylases. In some embodiments, dimerization of nuclease domain is required for cleavage activity.

Each zinc finger recognizes three consecutive base pairs in the target DNA. For example, a 3 finger domain recognizes a sequence of 9 contiguous nucleotides, with a dimerization requirement of the nuclease, two sets of zinc finger triplets are used to bind 18 nucleotides of recognition sequence. In some cases, engineered linker sequences are used between the zinc fingers allowing the fingers to 'skip' 1, 2 or more nucleotides between each three consecutive nucleotide unit. Useful designer zinc finger modules include those that recognize various GNN and ANN triplets (Dreier, et al., (2001) J Biol Chem 276:29466-78; Dreier, et al., (2000) J Mol Biol 303:489-502; Liu, et al., (2002) J Biol Chem 277:3850-6), as well as those that recognize various CNN or TNN triplets (Dreier, et al., (2005) J Biol Chem 280:35588-97; Jamieson, et al., (2003) Nature Rev Drug Discov 2:361-8). See also, Durai, et al., (2005) Nucleic Acids Res 33:5978-90; Segal, (2002) Methods 26:76-83; Porteus and Carroll, (2005) Nat Biotechnol 23:967-73; Pabo, et al., (2001) Ann Rev Biochem 70:313-40; Wolfe, et al., (2000) Ann Rev Biophys Biomol Struct 29:183-212; Segal and Barbas, (2001) Curr Opin Biotechnol 12:632-7; Segal, et al., (2003) Biochemistry 42:2137-48; Beerli and Barbas, (2002) Nat Biotechnol 20:135-41; Carroll, et al., (2006) Nature Protocols 1:1329; Ordiz, et al., (2002) Proc Natl Acad Sci USA 99:13290-5; Guan, et al., (2002) Proc Natl Acad Sci USA 99:13296-301; WO2002099084; WO00/42219; WO02/42459; WO2003062455; US20030059767; US Patent Application Publication Number 2003/0108880; U.S. Pat. Nos. 6,140,466, 6,511,808 and 6,453,242. Useful zinc-finger nucleases also include those described in WO03/080809; WO05/014791; WO05/084190; WO08/021207; WO09/042186; WO09/054985; and WO10/065123.

Where the gene-editing system comprises a zinc finger nuclease, optimal target sites may be selected using a number of publicly available online resources. See, e.g., Reyon et al., BMC Genomics 12:83 (2011), which is hereby incorporated by reference in its entirety. For example, Oligomerized Pool Engineering (OPEN) is a highly robust and publicly available protocol for engineering zinc finger arrays with high specificity and in vivo functionality, and has been successfully used to generate ZFNs that function efficiently in plants, zebrafish, and human somatic and pluripotent stem cells. OPEN is a selection-based method in which a pre-constructed randomized pool of candidate ZFAs is screened to identify those with high affinity and specificity for a desired target sequence. ZFNGenome is a GBrowse-based tool for identifying and visualizing potential target sites for OPEN-generated ZFNs. ZFNGenome provides a compendium of potential ZFN target sites in sequenced and annotated genomes of model organisms. ZFNGenome currently includes a total of more than 11.6 million potential ZFN target sites, mapped within the fully sequenced genomes of seven model organisms; *Saccharomyces cerevisiae, Chlamydomonas reinhardtii, Arabidopsis thaliana, Drosophila melanogaster, Danio rerio, Caenorhabditis elegans*, and *Homo sapiens*. Additional model organisms, including three plant species; *Glycine max* (soybean), *Oryza sativa* (rice), *Zea mays* (maize), and three animal species *Tribolium castaneum* (red flour beetle), *Mus musculus* (mouse), *Rattus norvegicus* (brown rat) can also be used. ZFNGenome provides information about each potential ZFN target site, including its chromosomal location and position relative to transcription initiation site(s). Users can query ZFNGenome using several different criteria (e.g., gene ID, transcript ID, target site sequence).

For more information on ZFNs, refer to U.S. Pat. No. 8,685,737, which is hereby incorporated by reference in its entirety.

TALENs

In some cases, the gene-editing system comprises a TAL-effector DNA binding domain-nuclease fusion protein (TALEN). A TAL effector comprises a DNA binding domain that interacts with DNA in a sequence-specific manner through one or more tandem repeat domains. The repeated sequence typically comprises 34 amino acids, and the repeats are typically 91-100% homologous with each other. Polymorphism of the repeats is usually located at positions 12 and 13, and there appears to be a one-to-one correspondence between the identity of repeat variable-diresidues at positions 12 and 13 with the identity of the contiguous nucleotides in the TAL-effector's target sequence.

The TAL-effector DNA binding domain can be engineered to bind to a desired target sequence, and fused to a nuclease domain, e.g., from a type II restriction endonuclease, e.g., a nonspecific cleavage domain from a type II restriction endonuclease such as FokI (see e.g., Kim et al. (1996) Proc. Natl. Acad. Sci. USA 93:1156-1160). Other useful endonucleases may include, for example, HhaI, HindIII, Nod, BbvCI, EcoRI, BglI, and AlwI. Thus, in some embodiments, a TALEN® includes a TAL effector domain containing a plurality of TAL effector repeat sequences that, in combination, bind to a specific nucleotide sequence in the target DNA sequence, such that the TALEN® cleaves the target DNA within or adjacent to the specific nucleotide sequence. Suitable TALEN® includes those described in WO10/079430 and U.S. Patent Application Publication No. 2011/0145940. See also, Ma et al. (2016) *Methods Mol. Biol.* 1451:17.

In some cases, the TAL effector domain that binds to a specific nucleotide sequence within a target DNA that includes 10 or more DNA binding repeats, and in some cases 15 or more DNA binding repeats. In some cases, each DNA binding repeat includes a repeat variable-diresidue (RVD) that determines recognition of a base pair in the target DNA sequence, wherein each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

If the sequence-specific, e.g., genome editing, endonuclease to be utilized is a TALEN®, in some cases, optimal target sites may be selected in accordance with the methods described by Sanjana et al., Nature Protocols, 7:171-192 (2012), which is hereby incorporated by reference in its entirety. In brief, TALENs function as dimers, and a pair of TALEN®, referred to as the left and right TALEN®, target sequences on opposite strands of DNA. TALEN® can be engineered as a fusion of the TALE DNA-binding domain and a monomeric FokI catalytic domain To facilitate FokI dimerization, the left and right TALEN® target sites can be chosen with a spacing of approximately 14-20 bases. Therefore, for a pair of TALEN®, each targeting 20-bp sequences, an optimal target site can have the form 5'-$TN^{19}N^{14-20}N^{19}A$-3', where the left TALEN targets 5'-$TN^{19}$-3' and the right TALEN targets the antisense strand of 5'-$N^{19}A$-3' (N=A, G, T or C).

For more information on TALENs, refer to U.S. Pat. No. 8,685,737, which is hereby incorporated by reference in its entirety.

CRISPR/Cas Effector Polypeptides

In some cases, the gene-editing polypeptide is a CRISPR/Cas effector polypeptide. In some cases, a suitable CRISPR-Cas effector polypeptide is a class 2 CRISPR/Cas effector polypeptide such as a type II, type V, or type VI CRISPR/Cas effector polypeptide. In some cases, a suitable CRISPR/Cas effector polypeptide is a class 2 CRISPR/Cas effector polypeptide. In some cases, a suitable CRISPR/Cas effector polypeptide is a type II CRISPR/Cas effector polypeptide (e.g., a Cas9 protein). In some cases, a suitable CRISPR/Cas effector polypeptide is a type V CRISPR/Cas effector polypeptide (e.g., a Cpf1 protein, a C2c1 protein, or a C2c3 protein), e.g., a Cas12a, a Cas12b, a Cas12c, a Cas12d, or a Cas12e polypeptide. In some cases, a suitable CRISPR/Cas effector polypeptide is a type VI CRISPR/Cas effector polypeptide (e.g., a C2c2 protein; also referred to as a "Cas13a" protein), e.g., a Cas13a, a Cas13b, a Cas13c, or a Cas13d polypeptide. In some cases, a suitable CRISPR/Cas effector polypeptide is a CasX protein. In some cases, a suitable CRISPR/Cas effector polypeptide is a CasY protein. In some cases, a suitable CRISPR/Cas effector polypeptide is a CasZ protein. In some cases, a suitable CRISPR/Cas effector polypeptide is a Cas14a, a Cas14b, or a Cas14c polypeptide.

In class 2 CRISPR systems, the functions of the effector complex (e.g., the cleavage of target DNA) are carried out by a single endonuclease (e.g., see Zetsche et al., Cell. 2015 Oct. 22; 163(3):759-71; Makarova et al., Nat Rev Microbiol. 2015 November; 13(11):722-36; Shmakov et al., Mol Cell. 2015 Nov. 5; 60(3):385-97); and Shmakov et al. (2017) *Nature Reviews Microbiology* 15:169. As such, the term "class 2 CRISPR/Cas protein" is used herein to encompass the CRISPR/Cas effector polypeptide (e.g., the target nucleic acid cleaving protein) from class 2 CRISPR systems. Thus, the term "class 2 CRISPR/Cas effector polypeptide" as used herein encompasses type II CRISPR/Cas effector polypeptides (e.g., Cas9); type V-A CRISPR/Cas effector polypeptides (e.g., Cpf1 (also referred to a "Cas12a")); type V-B CRISPR/Cas effector polypeptides (e.g., C2c1 (also referred to as "Cas12b")); type V-C CRISPR/Cas effector polypeptides (e.g., C2c3 (also referred to as "Cas12c")); type V-U1 CRISPR/Cas effector polypeptides (e.g., C2c4); type V-U2 CRISPR/Cas effector polypeptides (e.g., C2c8); type V-U5 CRISPR/Cas effector polypeptides (e.g., C2c5); type V-U4 CRISPR/Cas proteins (e.g., C2c9); type V-U3 CRISPR/Cas effector polypeptides (e.g., C2c10); type VI-A CRISPR/Cas effector polypeptides (e.g., C2c2 (also known as "Cas13a")); type VI-B CRISPR/Cas effector polypeptides (e.g., Cas13b (also known as C2c4)); and type VI-C CRISPR/Cas effector polypeptides (e.g., Cas13c (also known as C2c7)). To date, class 2 CRISPR/Cas effector polypeptides encompass type II, type V, and type VI CRISPR/Cas effector polypeptides, but the term is also meant to encompass any class 2 CRISPR/Cas effector polypeptide suitable for binding to a corresponding guide RNA and forming an RNP complex.

In some cases, the CRISPR/Cas effector polypeptide comprises an amino acid sequence having at least 50%, at least 60%, at least 70%, at least 80%, at least 90%, at least 95%, at least 98%, at least 99%, or 100%, amino acid sequence identity to the amino acid sequence depicted in any one of FIG. 3A-3P.

In some cases, the CRISPR/Cas effector polypeptide is a type II CRISPR/Cas effector polypeptide. In some cases, the CRISPR/Cas effector polypeptide is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA. In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcus pyogenes* Cas9 depicted in FIG. 3A. In some cases, the Cas9 polypeptide used in a composition or method of the present disclosure is a *Staphylococcus aureus* Cas9 (saCas9) polypeptide. In some cases, the saCas9 polypeptide comprises an amino acid sequence having at least 85%, at least 90%, at least 95%, at least 98%, at least 99%, or 100%, amino acid sequence identity to the saCas9 amino acid sequence depicted in FIG. 3G.

In some cases, a suitable Cas9 polypeptide is a high-fidelity (HF) Cas9 polypeptide. Kleinstiver et al. (2016) *Nature* 529:490. For example, amino acids N497, R661, Q695, and Q926 of the amino acid sequence depicted in FIG. 3A are substituted, e.g., with alanine. For example, an HF Cas9 polypeptide can comprise an amino acid sequence having at least 90%, at least 95%, at least 98%, at least 99%, or 100%, amino acid sequence identity to the amino acid sequence depicted in FIG. 3A, where amino acids N497, R661, Q695, and Q926 are substituted, e.g., with alanine. In some cases, a suitable Cas9 polypeptide exhibits altered PAM specificity. See, e.g., Kleinstiver et al. (2015) *Nature* 523:481.

In some cases, the genome-editing endonuclease is a type V CRISPR/Cas endonuclease. In some cases, a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in any one of FIG. 3H-3J.

Guide Nucleic Acids

A nucleic acid that binds to a class 2 CRISPR/Cas effector polypeptide (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA." A guide RNA provides target specificity to the complex (the RNP complex) by including a targeting segment, which includes a guide sequence (also referred to herein as a targeting sequence), which is a nucleotide sequence that is complementary to a sequence of a target nucleic acid. The term "guide RNA", as used herein, refers to an RNA that comprises: i) an "activator" nucleotide sequence that binds to a CRISPR/Cas effector polypeptide (e.g., a class 2 CRISPR/Cas effector polypeptide such as a type II, type V, or type VI CRISPR/Cas endonuclease) and activates the CRISPR/Cas effector polypeptide; and ii) a "targeter" nucleotide sequence that comprises a nucleotide sequence that hybridizes with a target nucleic acid. The "activator" nucleotide sequence and the "targeter" nucleotide sequence can be on separate RNA molecules (e.g., a "dual-guide RNA"); or can be on the same RNA molecule (a "single-guide RNA"). A guide nucleic acid in some cases includes only ribonucleotides. In some cases, a guide nucleic acid includes both ribonucleotides and deoxyribonucleotides.

In some cases, a CRISPR/Cas guide RNA comprises one or more modifications, e.g., a base modification, a backbone modification, a sugar modification, etc., to provide the nucleic acid with a new or enhanced feature (e.g., improved stability, such as improved in vivo stability). Suitable nucleic acid modifications include, but are not limited to: 2'0-methyl modified nucleotides, 2' fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Suitable modified nucleic acid backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included. A CRISPR-Cas guide RNA can also include one or more substituted sugar moieties. Suitable polynucleotides comprise a sugar substituent group selected from: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Examples of various CRISPR/Cas effector proteins and CRISPR/Cas guide RNAs (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013: 270805; Hou et al., Proc Natl Acad Sci U S A. 2013 Sep. 24; 110(39):15644-9; Jinek et al., Elife. 2013; 2:e00471; Pattanayak et al., Nat Biotechnol. 2013 September; 31(9):839-43; Qi et al., Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195 (3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 Dec; 51(12):835-43; Ran et al., Nat Protoc. 2013 November; 8(11):2281-308; Ran et al., Cell. 2013 Sep. 12; 154(6):1380-9; Upadhyay et al., G3

(Bethesda). 2013 Dec. 9; 3(12):2233-8; Walsh et al., Proc Natl Acad Sci U S A. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Examples and guidance related to type V or type VI CRISPR/Cas endonucleases and guide RNAs (as well as information regarding requirements related to protospacer adjacent motif (PAM) sequences present in targeted nucleic acids) can be found in the art, for example, see Zetsche et al., Cell. 2015 Oct. 22; 163(3):759-71; Makarova et al., Nat Rev Microbiol. 2015 November; 13(11):722-36; and Shmakov et al., Mol Cell. 2015 Nov. 5; 60(3):385-97.

Methods

The present disclosure provides methods of modifying a target nucleic acid in a cell (e.g., a target cell) by HDR. The methods generally involve introducing into the cell a composition of the present disclosure. The present disclosure provides methods of making a genetically modified cell. The methods comprise introducing into a target cell (where the target cell comprises a target DNA) a composition of the present disclosure, wherein the introducing step results in modification of the target DNA by HDR, thereby producing a genetically modified cell. Target nucleic acids include genomic DNA, mitochondrial DNA, and the like. In some cases, a target nucleic acid comprises a nucleotide sequence encoding a mutated polypeptide, e.g., a polypeptide that has reduced function as a result of a mutation (insertion and/or deletion and/or substitution of one or more nucleotides), where the polypeptide with reduced function causes a pathological condition.

In some cases, the target cell is in vitro. In some cases, the target cell is in vivo. In some cases, the target cell is a prokaryotic cell. In some cases, the target cell is a eukaryotic cell.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be an in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogeneic cells, allogeneic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some cases, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other cases, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other cases, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

In some cases, the plant cell is a cell of a plant component such as a leaf, a stem, a root, a seed, a flower, pollen, an anther, an ovule, a pedicel, a fruit, a meristem, a cotyledon, a hypocotyl, a pod, an embryo, endosperm, an explant, a callus, or a shoot.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera*, or *Lepidoptera*.

A cell is in some cases an insect cell. For example, in some cases, the cell is a cell of a mosquito, a grasshopper, a true bug, a fly, a flea, a bee, a wasp, an ant, a louse, a moth, or a beetle.

Methods of introducing a nucleic acids and polypeptides into a cell are known in the art, and any convenient method can be used to introduce a composition of the present into a target cell. Suitable methods are known in the art and include e.g., lipofection, electroporation, calcium phosphate precipitation, polyethyleneimine (PEI)-mediated transfection, DEAE-dextran mediated transfection, liposome-mediated transfection, virus-like particle-based delivery, particle gun technology, calcium phosphate precipitation, direct micro injection, nanoparticle-mediated delivery, and the like. Any or all of the components of a composition of the present disclosure can be introduced into a target cell using known methods.

Kits

The present disclosure provides a kit comprising components of a composition of the present disclosure. A kit of the present disclosure can include: a) a gene-editing polypeptide; b) a single-stranded donor DNA comprising: i) a first homology arm at or near the 5' end of the donor DNA, wherein the first homology arm comprises a nucleotide sequence that is at least partially complementary to a first nucleotide sequence in the target nucleic acid; ii) a second homology arm at or near the 3' end of the donor DNA, wherein the second homology arm comprises a nucleotide sequence that is at least partially complementary to a second nucleotide sequence in the target nucleic acid; and iii) a nucleotide sequence of interest, where the nucleotide sequence of interest is between the first homology arm and the second homology arm; and c) one or more staple oligonucleotides, wherein the one or more staple oligonucleotides are least partially complementary to the donor DNA such that the one or more staple oligonucleotides hybridize to donor DNA, such that the donor DNA template folds into a nanostructure in which the first homology arm and the second homology arm are brought into proximity to one another.

A kit of the present disclosure can further comprise a gene-editing polypeptide. For example, a kit of the present disclosure can further comprise a CRISPR/Cas effector polypeptide.

The components of the kit can be in separate containers. The components can be provided in a liquid solution, e.g., together with a buffer.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A composition comprising: a) a gene-editing polypeptide; b) a single-stranded donor DNA comprising: i) a first homology arm at or near the 5' end of the donor DNA, wherein the first homology arm comprises a nucleotide sequence that is at least partially complementary to a first nucleotide sequence in the target nucleic acid; ii) a second homology arm at or near the 3' end of the donor DNA, wherein the second homology arm comprises a nucleotide sequence that is at least partially complementary to a second nucleotide sequence in the target nucleic acid; and iii) a nucleotide sequence of interest between the first homology arm and the second homology arm; and c) one or more staple oligonucleotides, wherein the one or more staple oligonucleotides are least partially complementary to the nucleotide sequence of interest, such that the one or more staple oligonucleotides hybridize to the nucleotide sequence of interest, such that the single-stranded donor DNA folds into a DNA nanostructure in which the first homology arm and the second homology arm are brought into proximity to one another.

Aspect 2. The composition of aspect 1, comprising from 2 to 250 staple oligonucleotides.

Aspect 3. The composition of aspect 1, wherein the single-stranded donor DNA has a length of from about 50 nucleotides to about 10,000 nucleotides.

Aspect 4. The composition of aspect 1, wherein the single-stranded donor DNA has a length of from about 100 nucleotides to about 7,500 nucleotides, or from about 100 nucleotides to about 10,000 nucleotides.

Aspect 5. The composition of aspect 1, wherein the single-stranded donor DNA has a length of from about 1,000 nucleotides to about 7,500 nucleotides, or from about 1,000 nucleotides o about 10,000 nucleotides.

Aspect 6. The composition of any one of aspects 1-5, wherein at least one of the one or more staple oligonucleotides comprises a detectable label.

Aspect 7. The composition of aspect 6, wherein the detectable label comprises a fluorophore.

Aspect 8. The composition of any one of aspects 1-7, wherein each of the one or more staple oligonucleotides independently has a length of from about 10 nucleotides to about 60 nucleotides.

Aspect 9. The composition of any one of aspects 1-8, wherein each of the one or more staple oligonucleotides independently has a length of from about 20 nucleotides to about 50 nucleotides.

Aspect 10. The composition of any one of aspects 1-9, wherein the nanostructure comprises a 6-helix bundle.

Aspect 11. The composition of any one of aspects 1-9, wherein the nanostructure comprises a 24-helix bundle.

Aspect 12. The composition of any one of aspects 1-11, wherein the gene-editing polypeptide is a transcription activator-like effector nuclease.

Aspect 13. The composition of any one of aspects 1-11, wherein the gene-editing polypeptide is a zinc finger nuclease.

Aspect 14. The composition of any one of aspects 1-11, wherein the gene-editing polypeptide is a CRISPR/Cas effector polypeptide.

Aspect 15. The composition of aspect 14, wherein the CRISPR/Cas effector polypeptide is a type II CRISPR/Cas effector polypeptide.

Aspect 16. The composition of aspect 14, wherein the CRISPR/Cas effector polypeptide is a type V CRISPR/Cas effector polypeptide.

Aspect 17. The composition of aspect 14, wherein the CRISPR/Cas effector polypeptide is a type VI CRISPR/Cas effector polypeptide.

Aspect 18. The composition of any one of aspects 14-17, comprising one or more guide nucleic acids, wherein each of the one or more guide nucleic acids comprises a targeter nucleotide sequence that hybridizes to a target nucleic acid.

Aspect 19. The composition of aspect 18, wherein the guide nucleic acid is a guide RNA.

Aspect 20. The composition of aspect 19, wherein the guide RNA comprises one or more of: i) a modified sugar; ii) a modified base; and iii) a modified internucleoside linkage.

Aspect 21. The composition of any one of aspects 1-20, wherein the nucleotide sequence of interest comprises one or more of: i) a nucleotide sequence encoding a protein of interest; ii) a nucleotide sequence encoding an exon of a gene; iii) a promoter sequence; iv) an enhancer sequence; and v) a sequence encoding a non-coding RNA.

Aspect 22. A composition comprising: a) a gene-editing polypeptide; and b) a DNA nanostructure, wherein the DNA nanostructure comprises, in order from 5' to 3': i) a first homology arm; ii) a nucleotide sequence of interest that is hybridized to one or more staple oligonucleotides, wherein the nucleotide sequence of interest is folded via the staple oligonucleotides such that the nucleotide sequence of interest has a length of from about 5 nm to about 500 nm; and iii) a second homology arm.

Aspect 23. The composition of aspect 22, wherein the DNA nanostructure comprises a 6-helix bundle, a 24-helix bundle, a tube, a cube, a square lattice, or a honeycomb lattice.

Aspect 24. The composition of aspect 22, wherein the DNA nanostructure incorporates curvature.

Aspect 25. The composition of aspect 22, wherein the DNA nanostructure comprises one or more single-stranded regions that do not comprise a hybridized staple oligonucleotide.

Aspect 26. The composition of any one of aspects 22-25, wherein the gene-editing polypeptide is a CRISPR/Cas effector polypeptide and wherein the composition further comprises a guide nucleic acid.

Aspect 27. The composition of any one of aspects 22-26, wherein the composition is packaged in a virus-like particle.

Aspect 28. The composition of any one of aspects 22-27, wherein the DNA nanostructure comprises a small molecule, a nucleic acid, or a polypeptide encapsulated within the DNA nanostructure.

Aspect 29. A method of modifying a target nucleic acid in a cell by homology-directed repair, the method comprising introducing into the cell a composition according to any one of aspects 1-28.

Aspect 30. The method of aspect 29, wherein the cell is a prokaryotic cell.

Aspect 31. The method of aspect 29, wherein the cell is a eukaryotic cell.

Aspect 32. The method of aspect 31, wherein the cell is in vitro.

Aspect 33. The method of aspect 31, wherein the cell is in vivo.

Aspect 34. The method of any one of aspects 29-33, wherein the eukaryotic cell is a human cell, a non-human mammalian cell, a reptile cell, an amphibian cell, a cell of an invertebrate, a plant cell, an insect cell, an avian cell, a fungal cell, a fish cell, an algal cell, or an arachnid cell.

Aspect 35. The method of aspect 34, wherein the mammalian cell is a T cell or an NK cell.

Aspect 36. The method of aspect 35, wherein the nucleotide sequence of interest comprises a nucleotide sequence encoding a receptor.

Aspect 37. The method of aspect 36, wherein the receptor is a T cell receptor, an NK cell receptor, or a chimeric antigen receptor (CAR).

Aspect 38. A method of making a genetically modified cell, the method comprising the method comprising introducing into a target cell comprising a target DNA, a composition according to any one of aspects 1-28, wherein said introducing results in modification of the target DNA by homology directed repair, thereby producing a genetically modified cell.

Aspect 39. The method of aspect 38, wherein the cell is a prokaryotic cell.

Aspect 40. The method of aspect 38, wherein the cell is a eukaryotic cell.

Aspect 41. The method of aspect 40, wherein the cell is in vitro.

Aspect 42. The method of aspect 40, wherein the cell is in vivo.

Aspect 43. The method of any one of aspects 38-42, wherein the eukaryotic cell is a mammalian cell, a human cell, a non-human mammalian cell, a reptile cell, an amphibian cell, a cell of an invertebrate, a plant cell, an insect cell, an avian cell, a fish cell, a fungal cell, an algal cell, or an arachnid cell.

Aspect 44. The method of aspect 43, wherein the mammalian cell is a T cell or an NK cell.

Aspect 45. The method of aspect 44, wherein the nucleotide sequence of interest comprises a nucleotide sequence encoding a receptor.

Aspect 46. The method of aspect 45, wherein the receptor is a T cell receptor, an NK cell receptor, or a chimeric antigen receptor (CAR).

Aspect 47. A kit comprising: a) a gene-editing polypeptide; b) a single-stranded donor DNA comprising: i) a first homology arm at or near the 5' end of the donor DNA, wherein the first homology arm comprises a nucleotide sequence that is at least partially complementary to a first nucleotide sequence in the target nucleic acid; ii) a second homology arm at or near the 3' end of the donor DNA, wherein the second homology arm comprises a nucleotide sequence that is at least partially complementary to a second nucleotide sequence in the target nucleic acid; and iii) a nucleotide sequence of interest between the first homology arm and the second homology arm; and c) one or more staple oligonucleotides, wherein the one or more staple oligonucleotides are least partially complementary to the nucleotide sequence of interest, such that the one or more staple oligonucleotides hybridize to the nucleotide sequence of interest, such that the donor DNA template folds into a nanostructure in which the first homology arm and the second homology arm are brought into proximity to one another.

Aspect 48. The kit of aspect 47, wherein (a), (b), and (c) are in separate containers.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

To identify the three-dimensional structures ("nanostructures") that display the greatest efficiency for HDR, a library comprising six three-dimensional structures is generated with an EGFP expression plasmid, using six sets of stable oligonucleotides. Staple oligonucleotides are designed to cause different folding patterns and structures based on DNA base pairing (Rothemund (2006) *Nature* 440:297-302; Castro et al. (2011) *Nat. Methods* 8:221), including a 6-helix bundle and a 24-helix bundle. Each structure also comprises ssDNA homology arms to promote HDR into the genome.

The homology arms are not incorporated into the three-dimensional structure. Staple oligonucleotides can include chemical modifications such as fluorophores, or transcription factor binding motifs (to promote import into the nucleus or to promote recruitment of DNA repair proteins).

Two genomic sites are chosen for analysis: chr9:107,422,356/hg38 and chr1:179,826,688/hg38. Nanostructures are generated using staple oligonucleotides. The nanostructures are transfected, along with Cas9 and a guide RNA, into HEK293 cells and analyzed for HDR using polymerase chain reaction (PCR), Sanger sequencing, and next-generation sequencing (NGS). The experiment is repeated using larger payloads (the portion of the donor DNA between the homology arms) encoding a dead Cas9 (dCas9) polypeptide. Results of the two experiments are compared. Nanostructures promote HDR with large DNA insertions.

Examples of donor DNA and homology arms are shown in FIG. 4-FIG. 7. One donor DNA ("BFP-mEGFP construct"; FIG. 4) comprises a nucleotide sequence encoding blue fluorescent protein (BFP) under transcriptional control of an EF-1 alpha promoter+T7 promoter, and also includes a woodchuck hepatitis virus post-transcriptional regulatory element (WPRE), which increases transgene expression. It also has a 5' homology arm and a 3' homology arm. This donor DNA is folded into a nanostructure and is introduced, along with a Cas9 protein and a guide RNA, into HEK293 cells. This genetically modified cell line can be used to study HDR, which is detected by replacing a codon in BFP that produces green fluorescence protein instead of blue fluorescent protein. Introduction of this construct into specific loci in the genome allowed one to study locus- and chromatin-specific effects in HDR.

One donor DNA (dCas9-3×Flag-2×NLS; FIG. 5) comprises a nucleotide sequence encoding an inactive Cas9 (dCas9) polypeptide tagged with 3×Flag and 2×NLS (nuclear localization signal) under transcriptional control of a β-actin promoter, and also includes a beta-globin poly (A) signal. It also has a 5' homology arm and a 3' homology arm. This donor DNA is folded into a nanostructure and is introduced, along with a Cas9 protein and a guide RNA, into HEK293 cells. By changing the homology arms, this construct can allow endogenous fusion of proteins with dCas9 and can also allow integration of dCas9 or an active Cas9 into specific loci in the genome. Examples of homology arms are provided in FIG. 6 and FIG. 7.

Example 2: Generation and Characterization of DNA Nanostructures

Figure 8A:
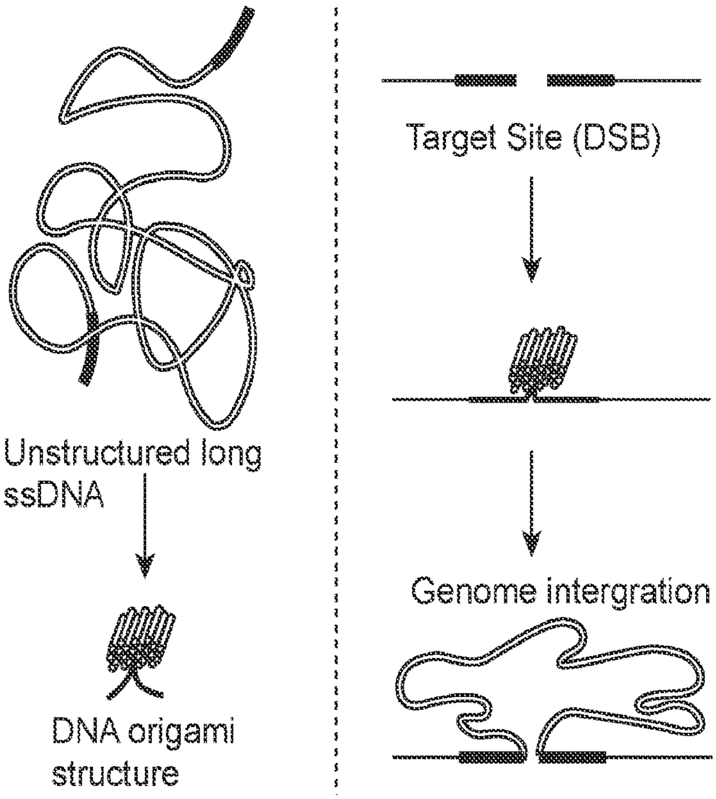
FIG. 8A-8D depict design, purification and characterization of a DNA nanostructure encoding mNeon for integration into the human genome.
Figure 8B:
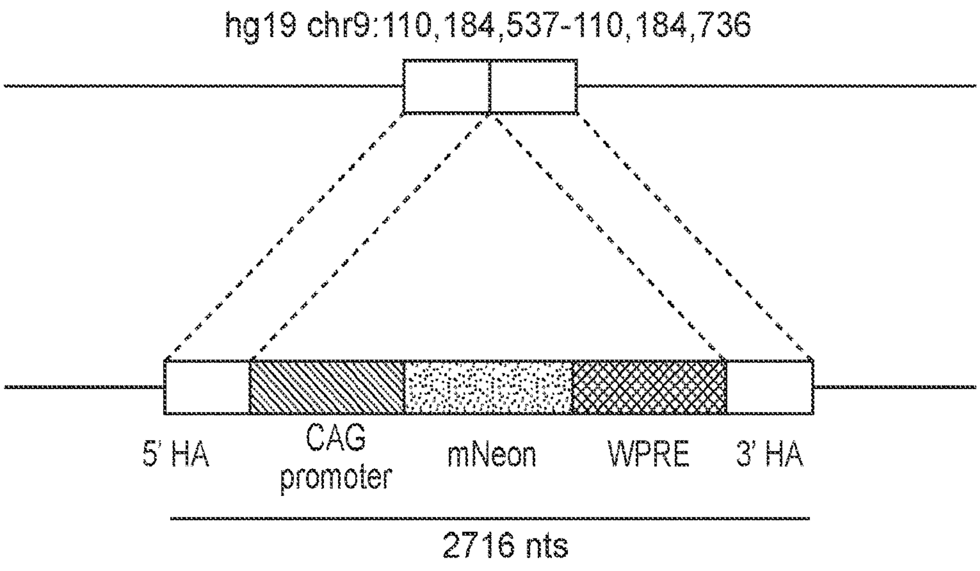
Figure 8C:
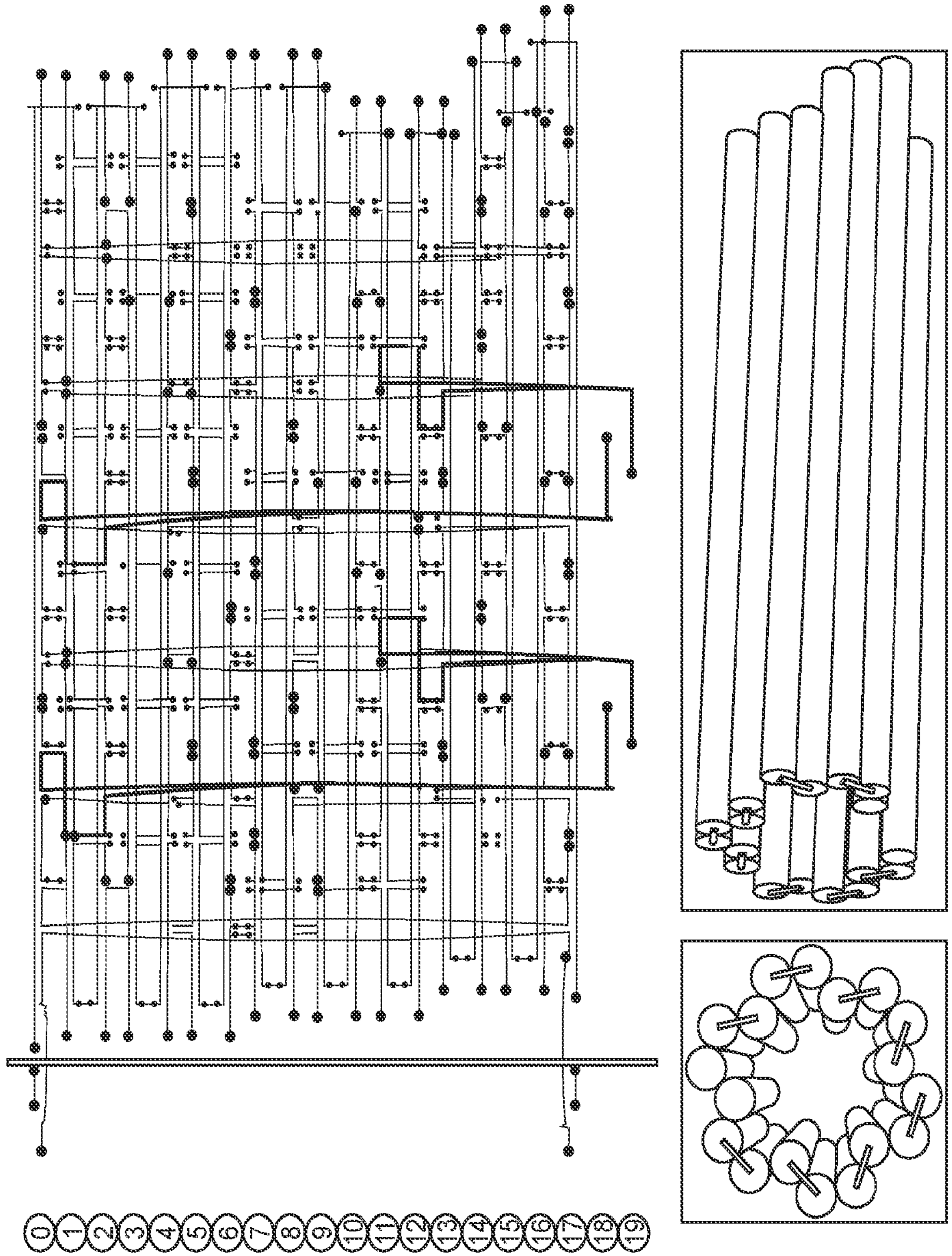
Figure 8D:
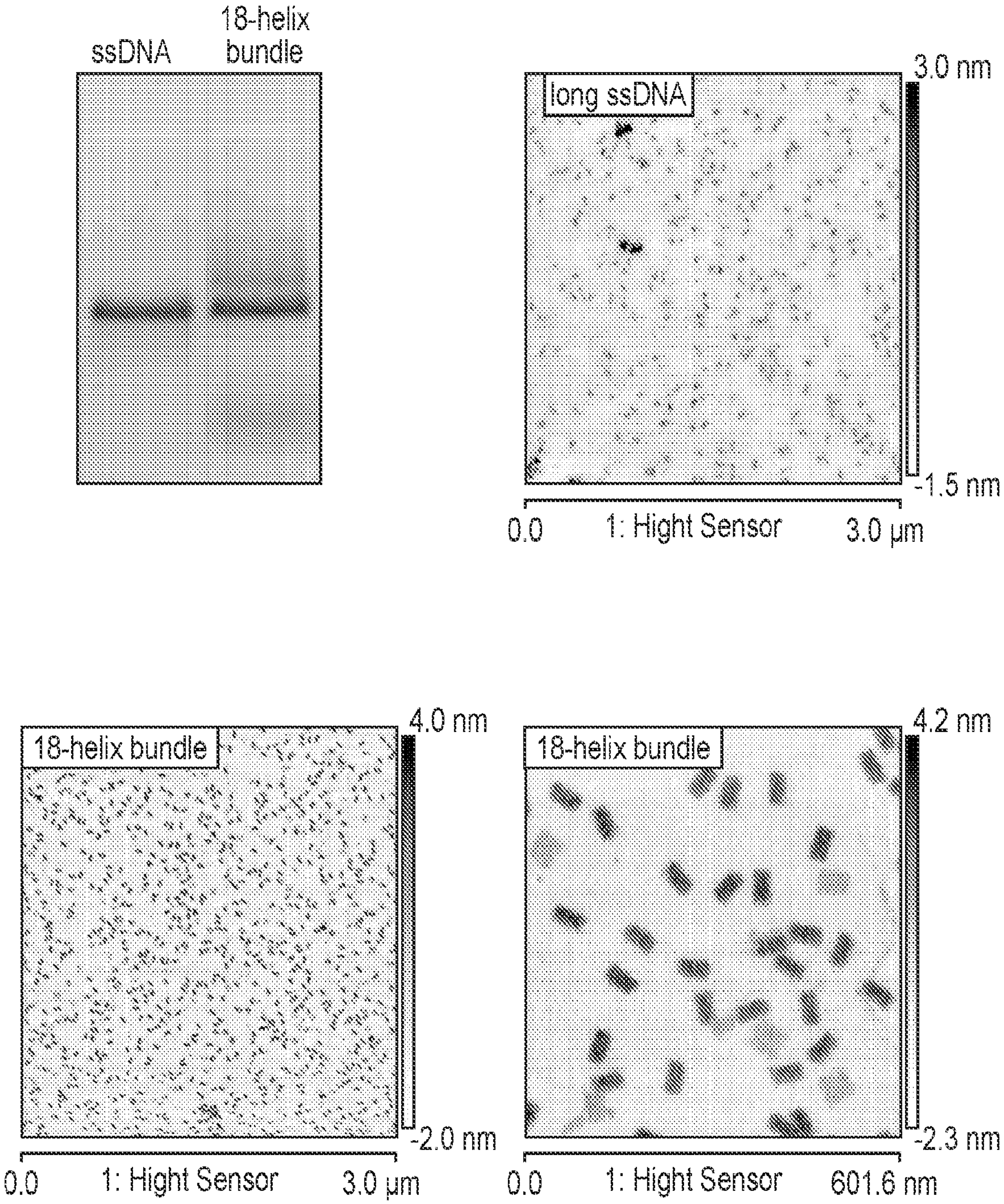

FIG. 8A-8D depict design, purification and characterization of a DNA nanostructure encoding mNeon for integration into the human genome. FIG. 8A. Schematic of a long unstructured ssDNA HDR template folded into a DNA nanostructure and integrated into the genome via CRISPR/Cas9-mediated HDR. FIG. 8B. Schematic of a 2716 bases long template to insert mNeon into an intergenic site in the human genome. FIG. 8C. Cadnano design of an 18-helix bundle DNA nanostructure and structure prediction. FIG. 8D. Gel and atomic force microscopy (AFM) characterization of the 18-helix bundle DNA nanostructure.

Figure 9A:
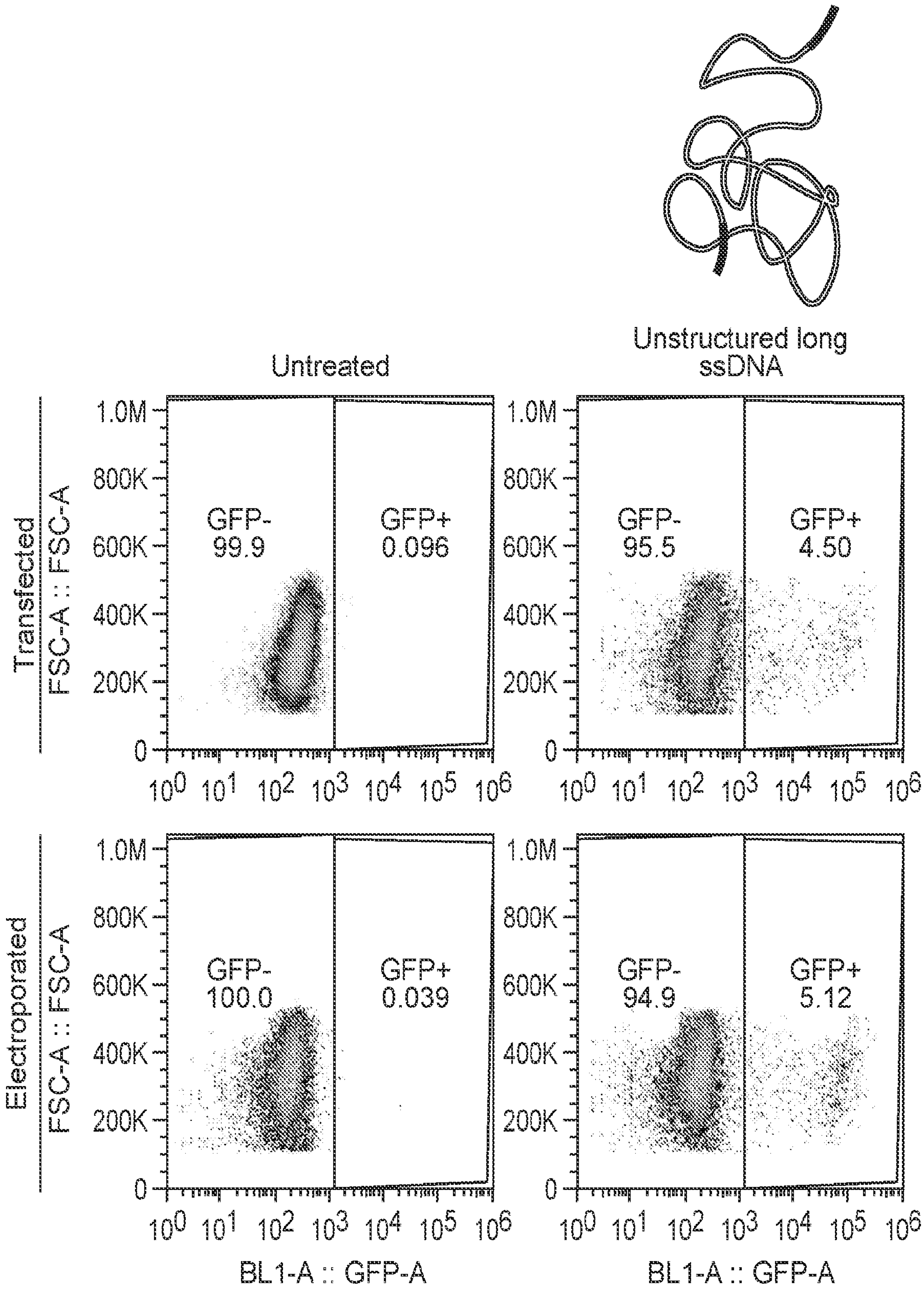
FIG. 9A-9D depict entry into the nucleus and integration into the genome via HDR of DNA nanostructures compared to unstructured ssDNA.
Figure 9A:
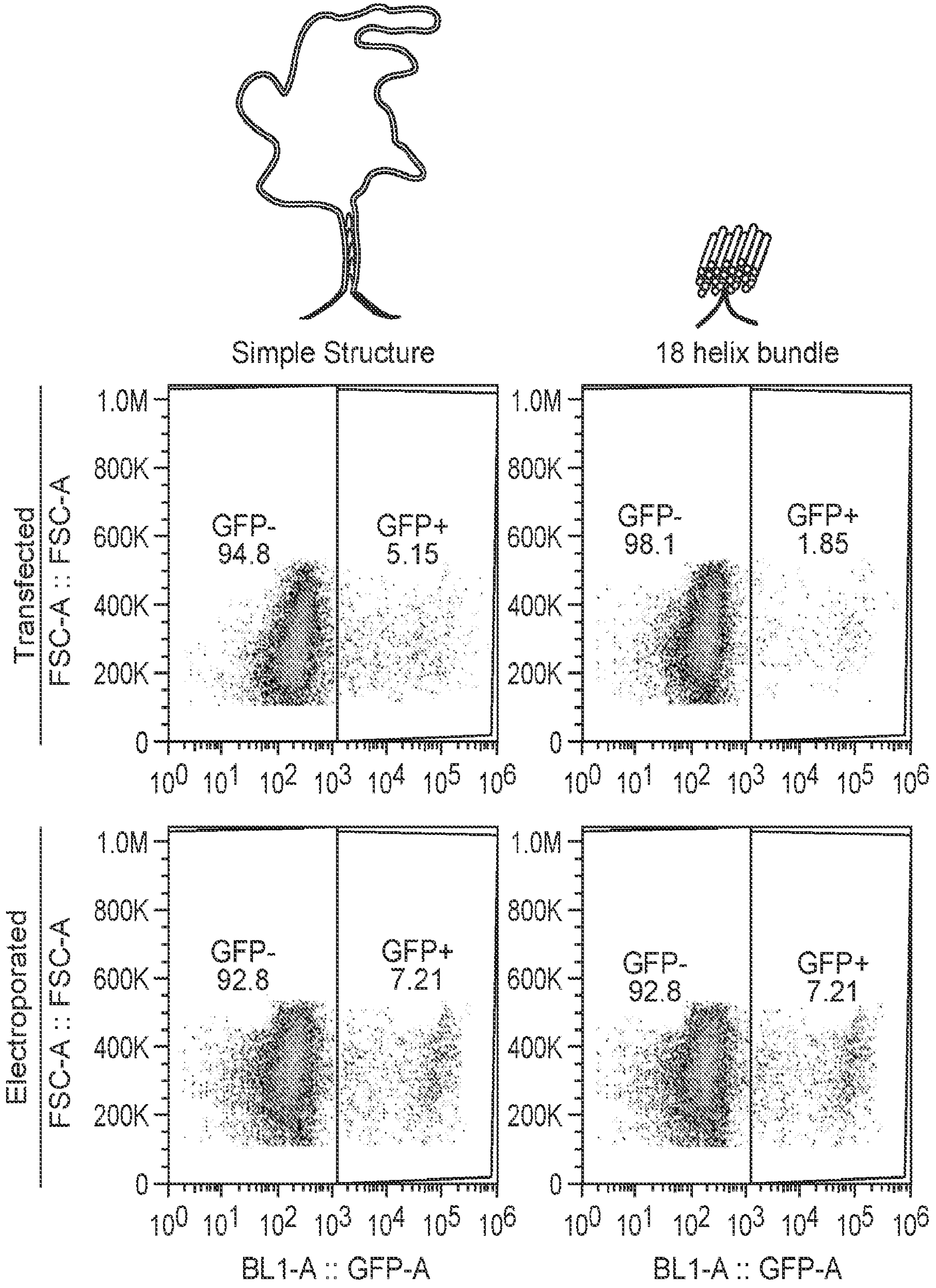
Figure 9B:
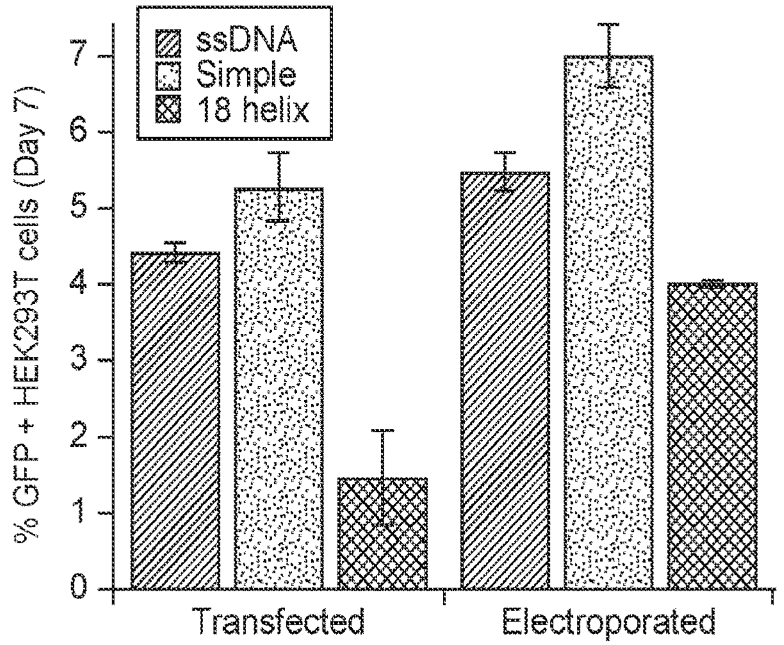
Figure 9C:
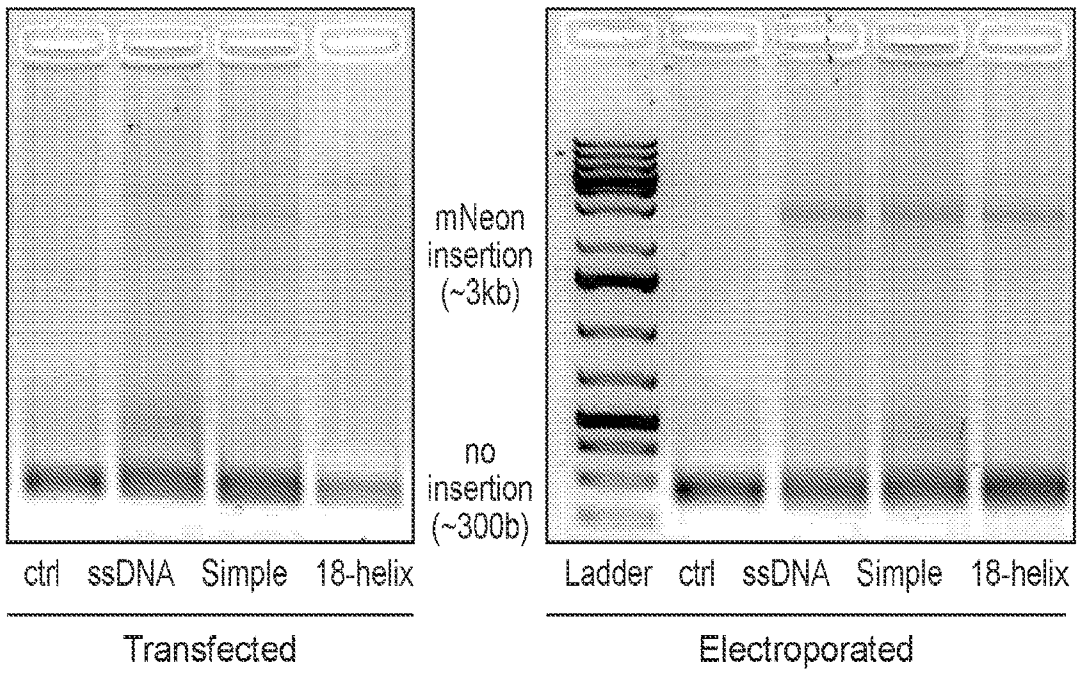
Figure 9D:
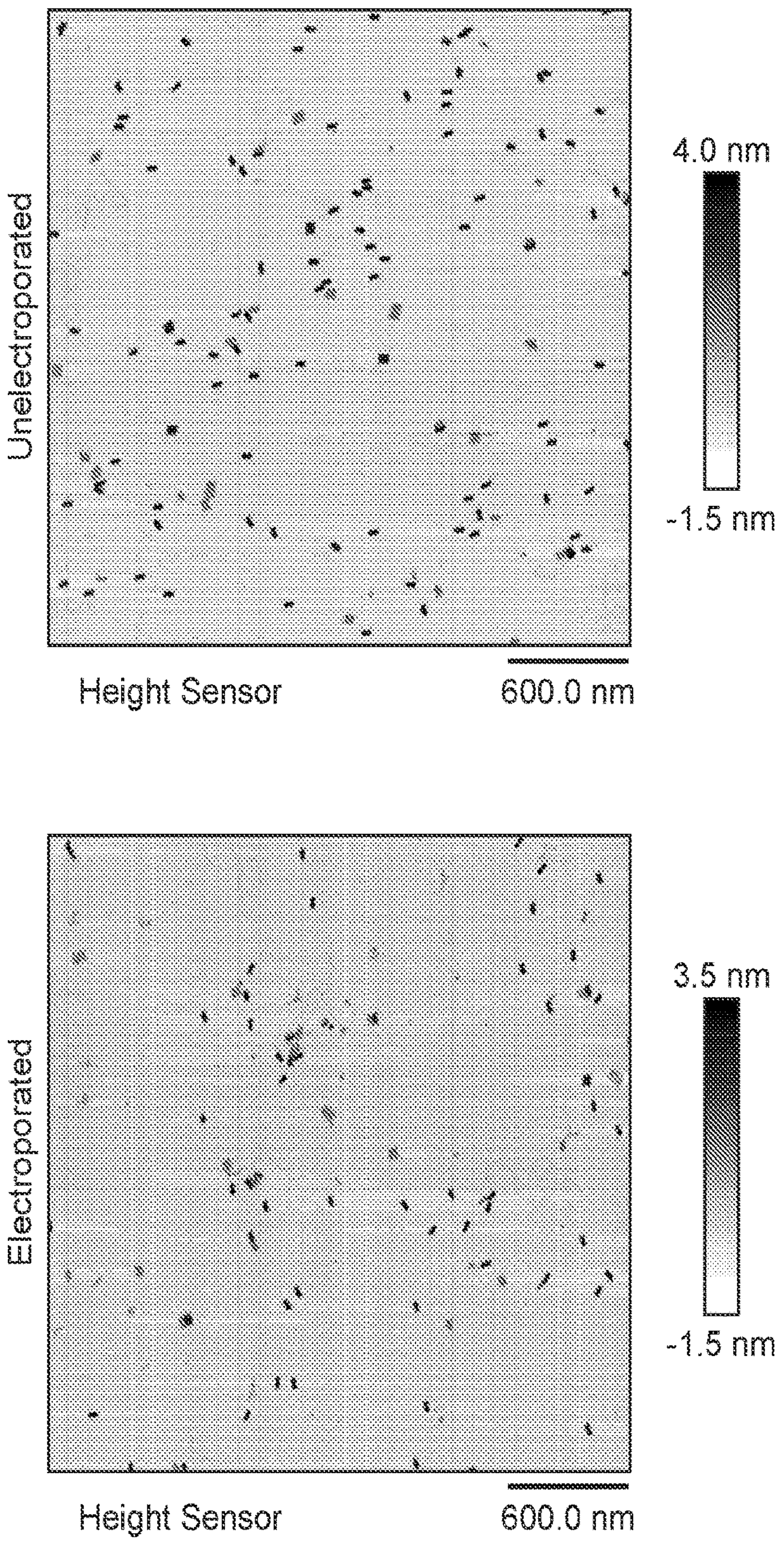

FIG. 9A-9D depict entry into the nucleus and integration into the genome via HDR of DNA nanostructures compared to unstructured ssDNA. The data show that electroporation allows DNA nanostructures to enter the nucleus and integrate into the genome at similar rates as unstructured ssDNA through homology directed editing. FIG. 9A. Flow Cytometry data shows simple structures (ssDNA+5 staples) are more efficiently incorporated into the genome compared to unstructured ssDNA and the 18-helix bundle. Electroporation shows similar values across unstructured, simple and the 18-helix bundle. FIG. 9B. Graphed flow cytometry data shows simple structures perform best for both transfection and electroporation. FIG. 9C. PCR using primers flanking the insertion site show electroporation leads to similar insertion efficiencies for ssDNA, simple and the 18-helix bundle. A larger insertion was observed for ssDNA and the 18-helix bundle which could be a concatemer, simple structure shows a single band at the right size. FIG. 9D. AFM images show that the 18-helix bundle retained its shape after electroporation.

Figure 10A:
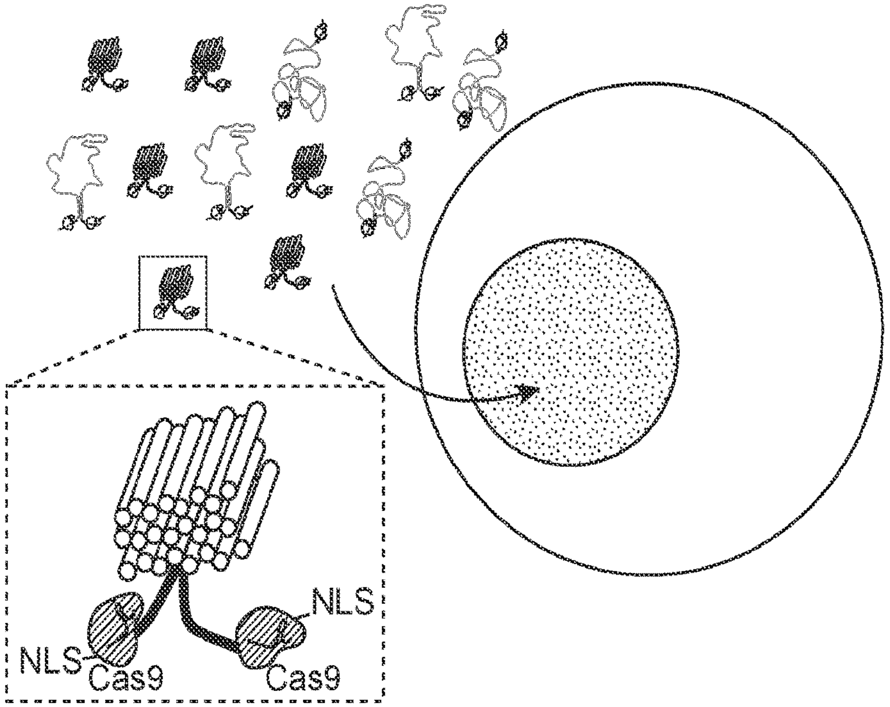
FIG. 10A-10D depict recruitment of CRISPR Cas9 to the ends of templates using shuttles.
Figure 10B:
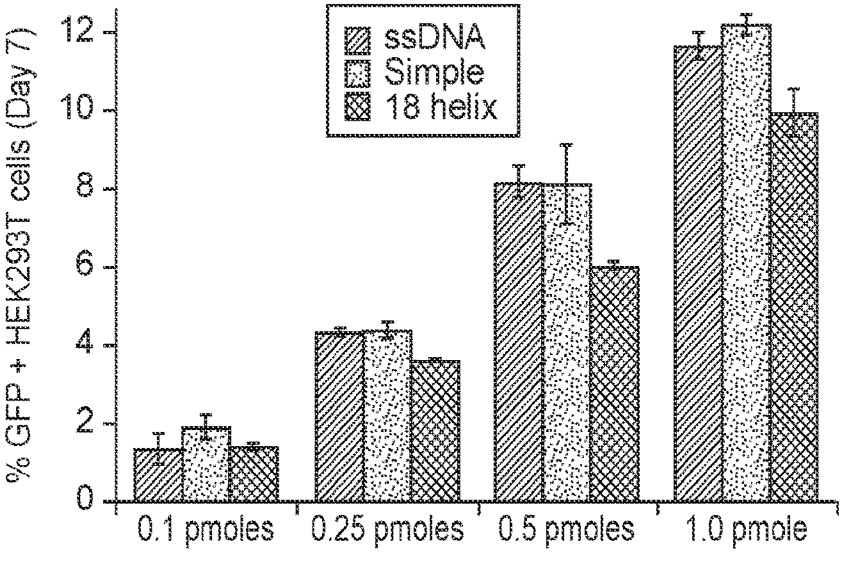
Figure 10C:
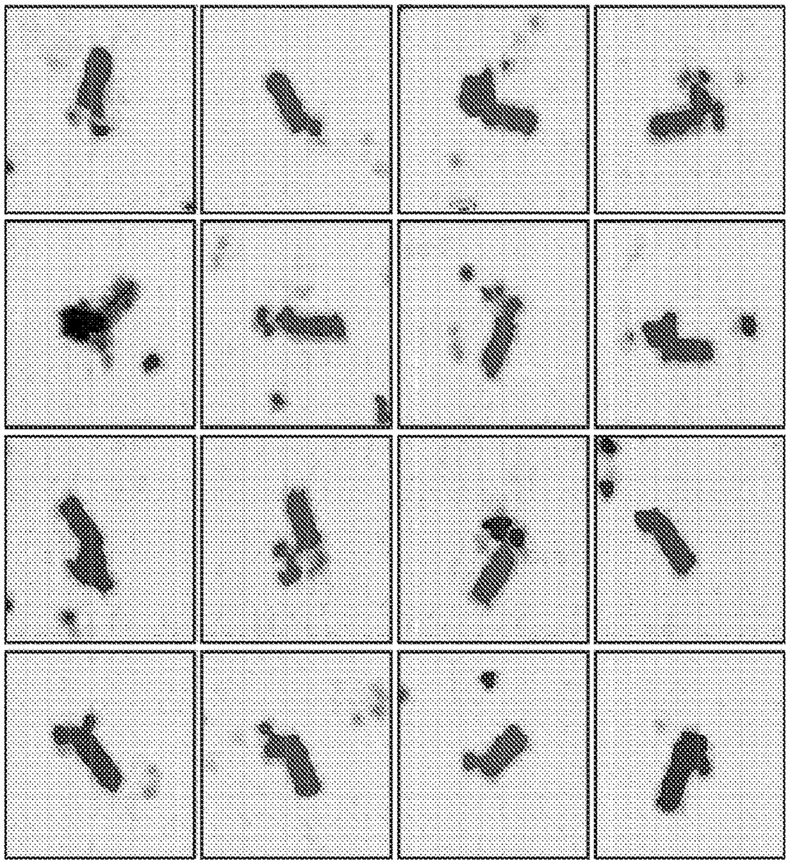
Figure 10D:
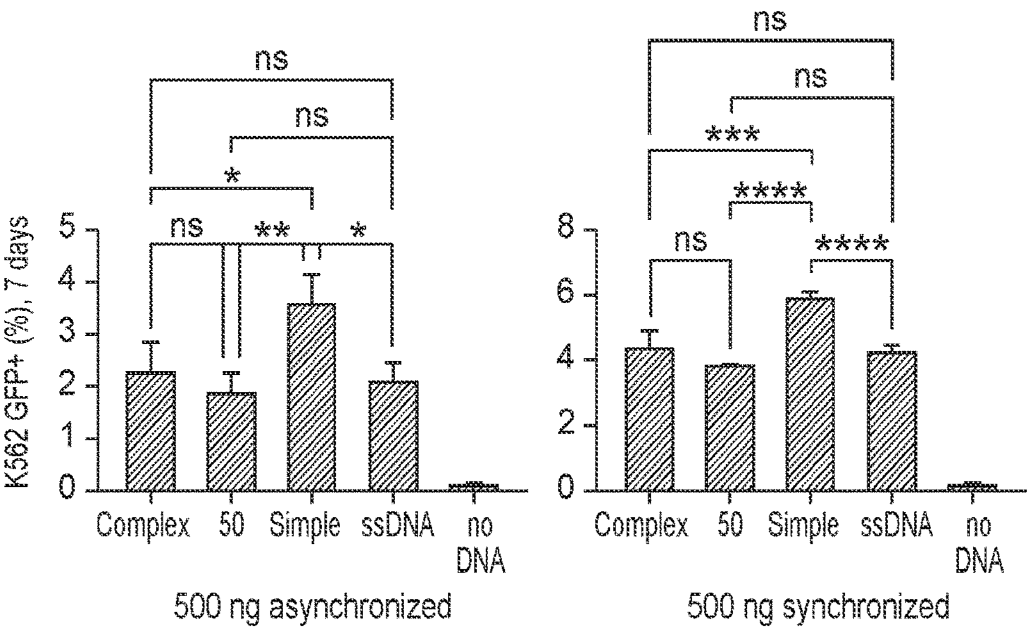

FIG. 10A-10D depict recruitment of CRISPR Cas9 to the ends of templates using shuttles. The data show recruiting CRISPR Cas9 to the ends of the templates using shuttles, leading to higher knockin efficiencies of large templates, including DNA nanostructures, in both HEK293T cells and K562 cells. FIG. 10A. Schematic of Cas9 binding to the ends of the templates for shuttling them into the nucleus. FIG. 10B. Flow cytometry data shows electroporated, shuttled ssDNA, simple and the 18-helix bundle have similar knockin efficiencies. FIG. 10C. AFM image of CRISPR Cas9 RNP bound to the 18-helix bundle. FIG. 10D. Simple structure shows significantly higher knockin into K562 cells, compared to unstructured ssDNA.

Figure 11A:
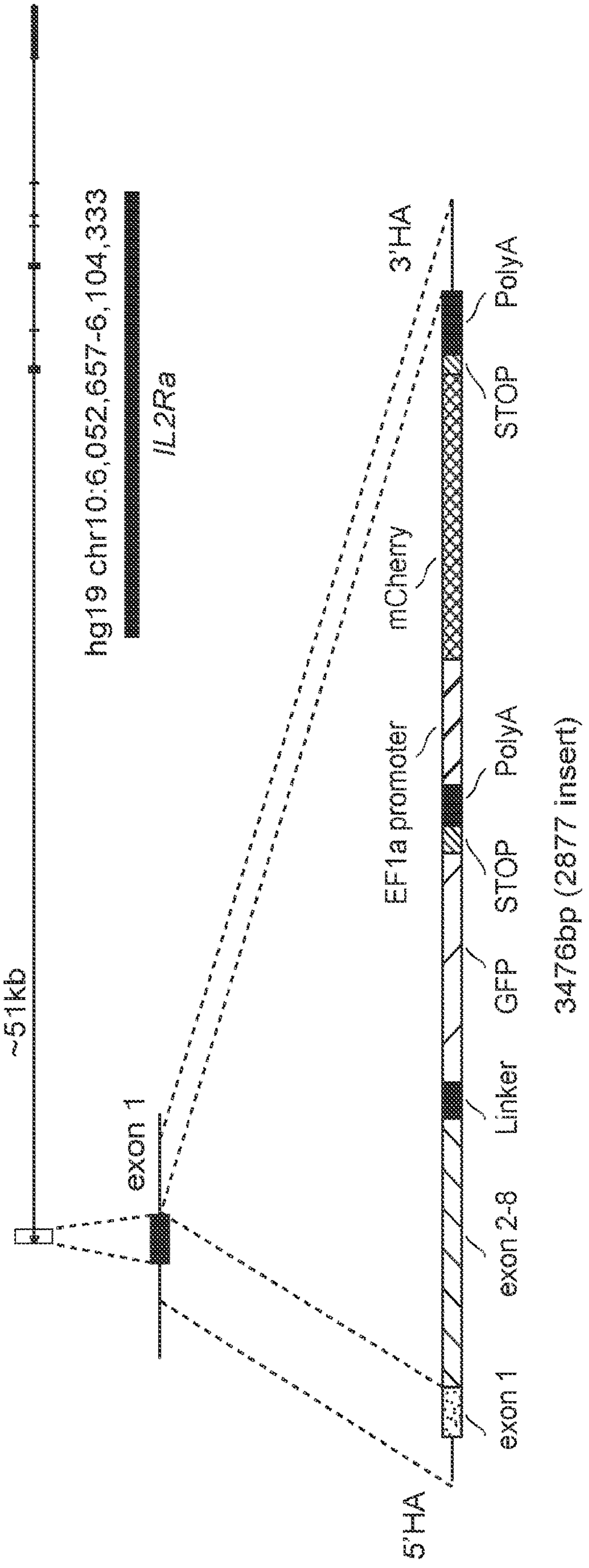
FIG. 11A-11E depict incorporation of DNA nanostructures encoding a human genome into human primary cells.
Figure 11B:
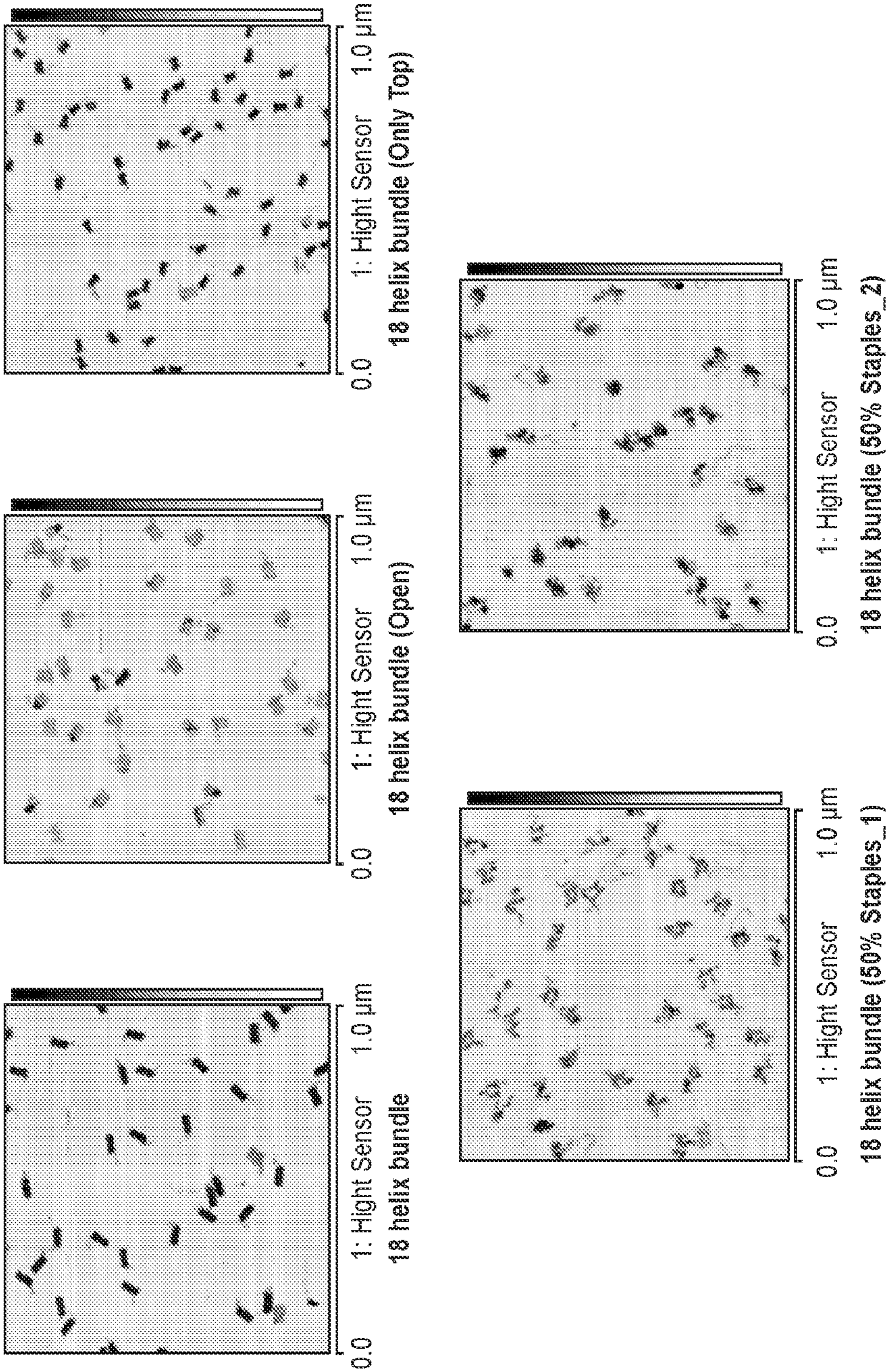
Figure 11C:
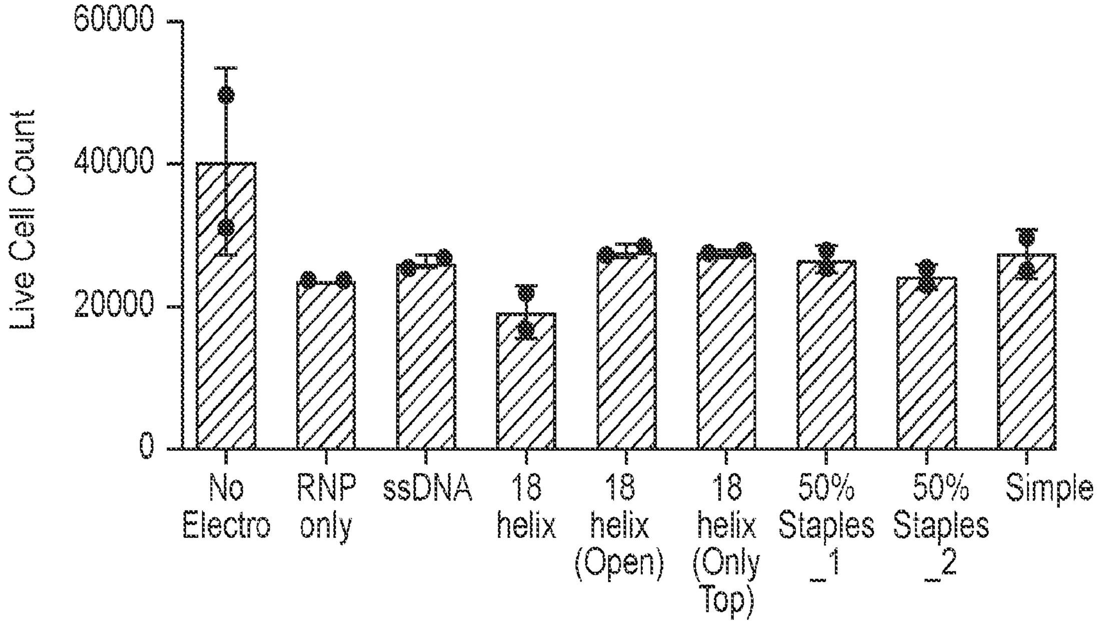
Figure 11D:
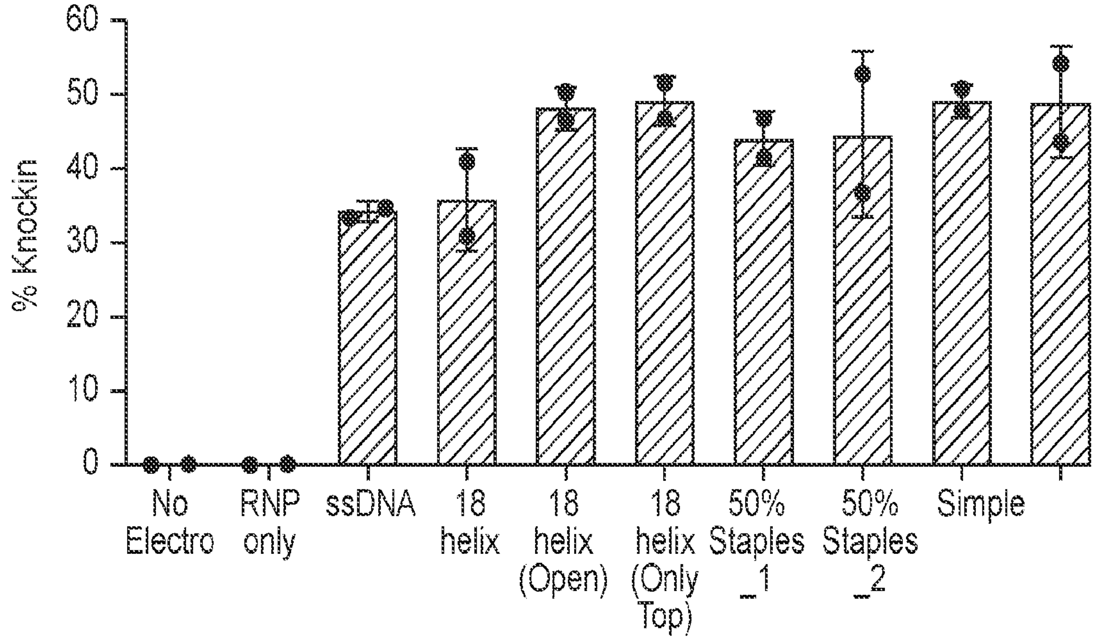
Figure 11E:
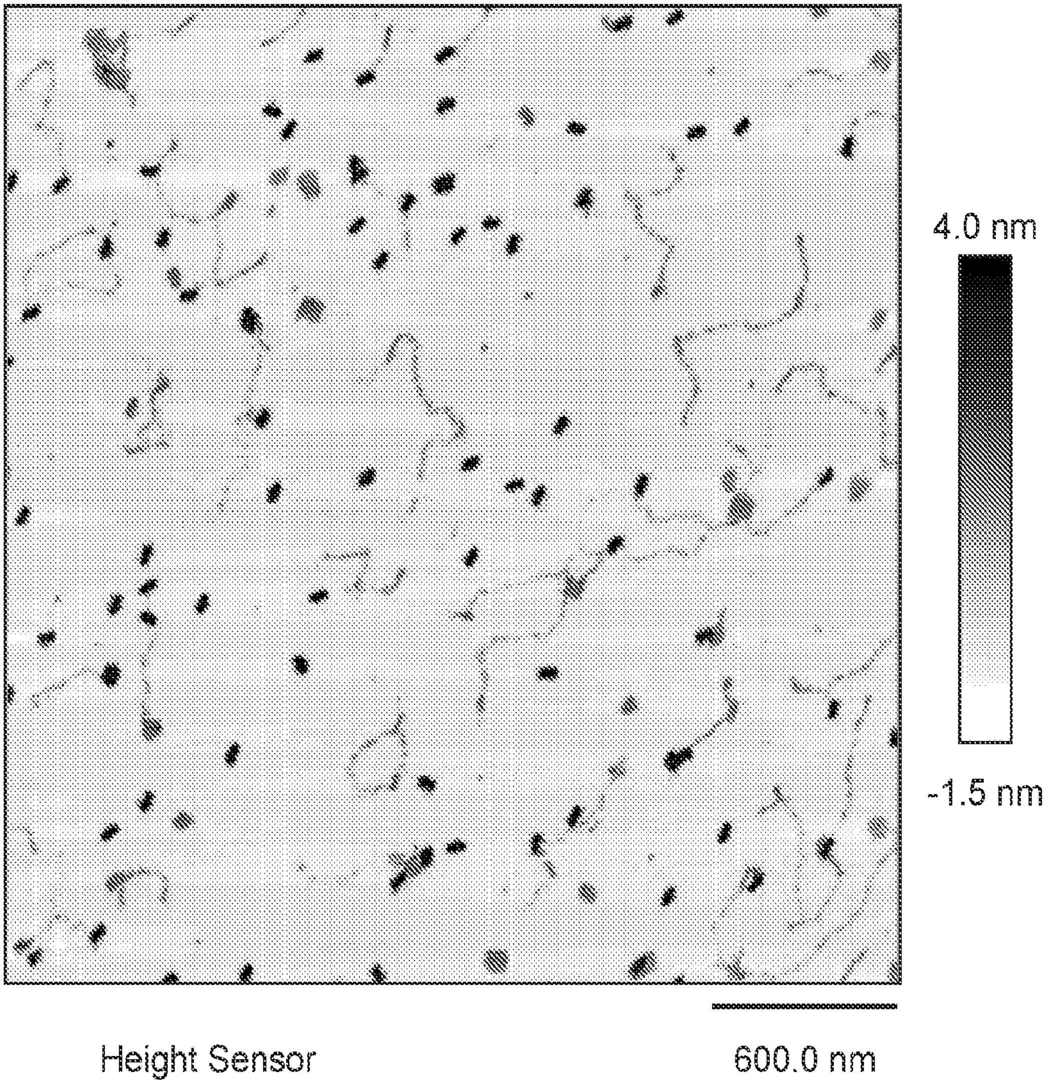

FIG. 11A-11E depict incorporation of DNA nanostructures encoding a human genome into human primary cells. The data show that DNA nanostructures encoding a human genome are incorporated into human primary cells with high efficiency. FIG. 11A. Schematic of knockin strategy of a 3.5 kb HDR template encoding IL2RA with a linked GFP, as well as an mCherry under a EF1a promoter. FIG. 11B. Different DNA nanostructure designs using the template shown in FIG. 11A). FIG. 11C. Live cell count shows the 18-helix bundle has a slightly higher toxicity compared to other structures and unstructured ssDNA. FIG. 11D. Structured templates show increased knockin efficiency compared to ssDNA alone, except for the 18-helix bundle. FIG. 11E. A mix of 18-helix bundles and unstructured dsDNA showed a striking end-to-end size difference.

Figure 12:
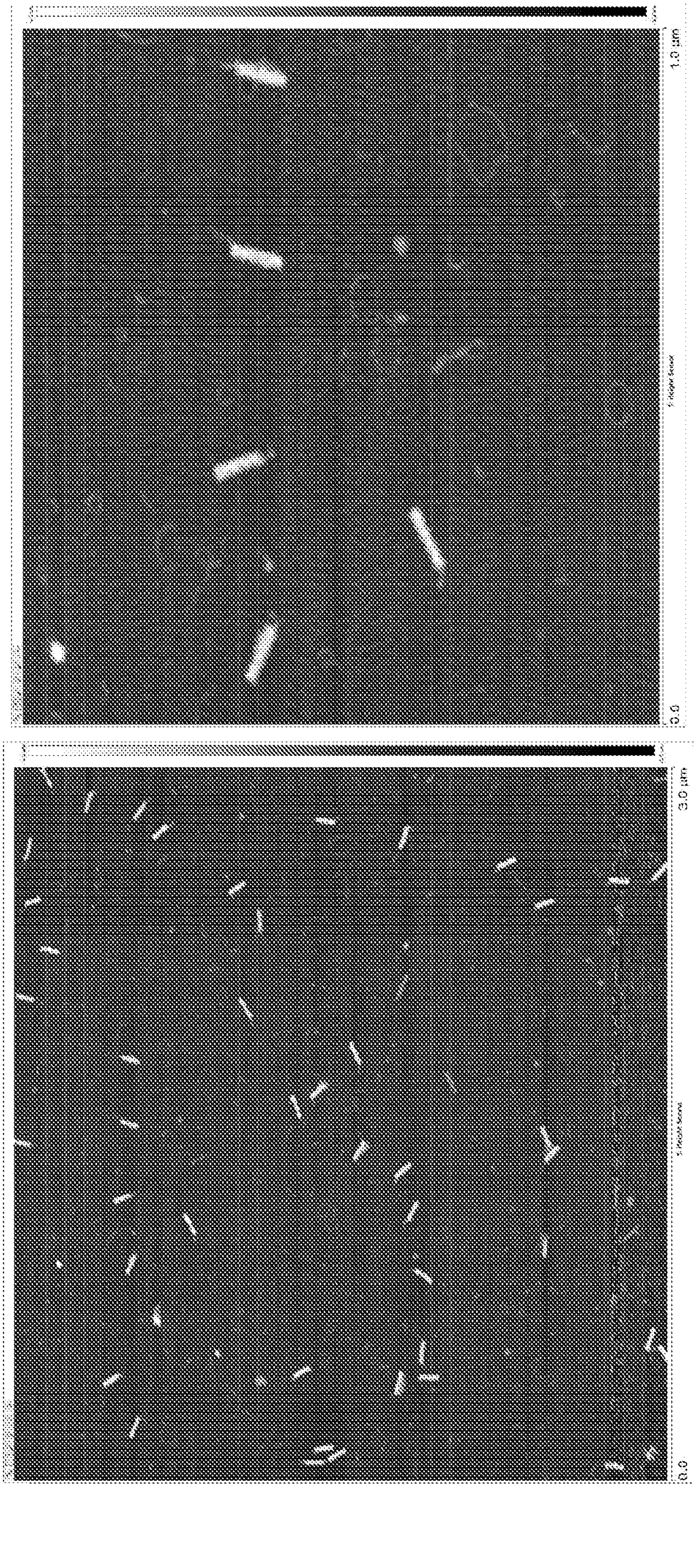
FIG. 12 depicts an atomic force microscope (AFM) image of a 5 kb ssDNA encoding IL2Ra, folded into a long 18-helix bundle.

FIG. 12 depicts an atomic force microscope (AFM) image of a 5 kb ssDNA encoding IL2Ra, folded into a long 18-helix bundle. The image shows that a longer 18-helix bundle encoding IL2Ra is folded with high precision.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising:

a) a gene-editing polypeptide; and b) a DNA nanostructure, wherein the DNA nanostructure comprises a single stranded donor DNA (ssDNA donor) and staple oligonucleotides, wherein the ssDNA donor comprises, in order from 5' to 3':

i) a first homology arm;

ii) a nucleotide sequence of interest that is hybridized to the staple oligonucleotides, wherein the nucleotide sequence of interest is folded via the staple oligonucleotides such that the nucleotide sequence of interest has a length of from about 5 nm to about 500 nm; and iii) a second homology arm.

2. The composition of claim 1, wherein the DNA nanostructure comprises an 18-helix bundle, a 6-helix bundle, a 24-helix bundle, a tube, a cube, a square lattice, or a honeycomb lattice.

3. The composition of claim 1, wherein the ssDNA donor comprises one or more single-stranded regions that do not comprise a hybridized staple oligonucleotide.

4. The composition of claim 1, wherein the composition is packaged in a virus-like particle.

5. The composition of claim 1, wherein the DNA nanostructure comprises a small molecule, a nucleic acid, or a polypeptide encapsulated within the DNA nanostructure.

6. A method of making a genetically modified cell, the method comprising introducing into a target cell comprising a target DNA, a composition according to claim 1, wherein said introducing results in modification of the target DNA by homology directed repair, thereby producing a genetically modified cell.

7. The method of claim 6, wherein the cell is a eukaryotic cell.

8. The method of claim 7, wherein the cell is in vivo.

9. The method of claim 7, wherein the eukaryotic cell is a mammalian T cell or a mammalian NK cell.

10. The composition of claim 1, wherein the gene-editing polypeptide is a CRISPR/Cas effector polypeptide and wherein the composition further comprises a guide nucleic acid.

11. The composition of claim 10, wherein the CRISPR/Cas effector polypeptide is a type II CRISPR/Cas effector polypeptide.

12. The composition of claim 1, wherein the gene-editing polypeptide is a transcription activator-like effector nuclease or a zinc finger nuclease.

13. The composition of claim 1, wherein the nucleotide sequence of interest is folded via the staple oligonucleotides such that the nucleotide sequence of interest has a length of from about 10 nm to about 50 nm.

14. The composition of claim 1, wherein the nucleotide sequence of interest is folded via the staple oligonucleotides such that the nucleotide sequence of interest has a length of from about 25 nm to about 50 nm.

15. The composition of claim 1, wherein the nucleotide sequence of interest is folded via the staple oligonucleotides such that the nucleotide sequence of interest has a length of about 25 nm.

16. The composition of claim 1, wherein the nucleotide sequence of interest is 2000-5000 nt in length.

17. The composition of claim 1, wherein the nucleotide sequence of interest is about 2500 nt in length.

18. A composition comprising:

a) a gene-editing polypeptide; and b) a DNA nanostructure, wherein the DNA nanostructure comprises a single stranded donor DNA (ssDNA donor) and staple oligonucleotides, wherein the ssDNA donor comprises, in order from 5' to 3':

i) a first homology arm;

ii) a nucleotide sequence of interest that is hybridized to the staple oligonucleotides, wherein the nucleotide sequence of interest is folded via the staple oligonucleotides such that the nucleotide sequence of interest has a length of from about 5 nm to about 500 nm; and iii) a second homology arm, wherein the DNA nanostructure comprises an 18-helix bundle.

19. A method of making a genetically modified cell, the method comprising introducing into a target cell comprising a target DNA, a composition according to claim 18, wherein said introducing results in modification of the target DNA by homology directed repair, thereby producing a genetically modified cell.

* * * * *

SEQUENCE LISTING

<160> NUMBER OF SEQ ID NOS: 29

<210> SEQ ID NO 1
<211> LENGTH: 7
<212> TYPE: PRT
<213> ORGANISM: Unknown
<220> FEATURE:
<223> OTHER INFORMATION: nuclear localization signal

<400> SEQUENCE: 1

```
Pro Lys Lys Lys Arg Lys Val
1               5
```

<210> SEQ ID NO 2
<211> LENGTH: 8
<212> TYPE: PRT
<213> ORGANISM: Unknown
<220> FEATURE:
<223> OTHER INFORMATION: nuclear localization signal

<400> SEQUENCE: 2

```
Val Ser Arg Lys Arg Pro Arg Pro
1               5
```

<210> SEQ ID NO 3
<211> LENGTH: 6
<212> TYPE: PRT
<213> ORGANISM: Unknown
<220> FEATURE:
<223> OTHER INFORMATION: nuclear localization signal

<400> SEQUENCE: 3

```
Gln Arg Lys Arg Lys Gln
1               5
```

<210> SEQ ID NO 4
<211> LENGTH: 1368
<212> TYPE: PRT
<213> ORGANISM: Streptococcus pyogenes

<400> SEQUENCE: 4

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

-continued

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
```

-continued

```
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                 1005
```

-continued

Val Tyr Gly Asp Tyr Lys Val Tyr Asp Val Arg Lys Met Ile Ala
1010 1015 1020

Lys Ser Glu Gln Glu Ile Gly Lys Ala Thr Ala Lys Tyr Phe Phe
1025 1030 1035

Tyr Ser Asn Ile Met Asn Phe Phe Lys Thr Glu Ile Thr Leu Ala
1040 1045 1050

Asn Gly Glu Ile Arg Lys Arg Pro Leu Ile Glu Thr Asn Gly Glu
1055 1060 1065

Thr Gly Glu Ile Val Trp Asp Lys Gly Arg Asp Phe Ala Thr Val
1070 1075 1080

Arg Lys Val Leu Ser Met Pro Gln Val Asn Ile Val Lys Lys Thr
1085 1090 1095

Glu Val Gln Thr Gly Gly Phe Ser Lys Glu Ser Ile Leu Pro Lys
1100 1105 1110

Arg Asn Ser Asp Lys Leu Ile Ala Arg Lys Lys Asp Trp Asp Pro
1115 1120 1125

Lys Lys Tyr Gly Gly Phe Asp Ser Pro Thr Val Ala Tyr Ser Val
1130 1135 1140

Leu Val Val Ala Lys Val Glu Lys Gly Lys Ser Lys Lys Leu Lys
1145 1150 1155

Ser Val Lys Glu Leu Leu Gly Ile Thr Ile Met Glu Arg Ser Ser
1160 1165 1170

Phe Glu Lys Asn Pro Ile Asp Phe Leu Glu Ala Lys Gly Tyr Lys
1175 1180 1185

Glu Val Lys Lys Asp Leu Ile Ile Lys Leu Pro Lys Tyr Ser Leu
1190 1195 1200

Phe Glu Leu Glu Asn Gly Arg Lys Arg Met Leu Ala Ser Ala Gly
1205 1210 1215

Glu Leu Gln Lys Gly Asn Glu Leu Ala Leu Pro Ser Lys Tyr Val
1220 1225 1230

Asn Phe Leu Tyr Leu Ala Ser His Tyr Glu Lys Leu Lys Gly Ser
1235 1240 1245

Pro Glu Asp Asn Glu Gln Lys Gln Leu Phe Val Glu Gln His Lys
1250 1255 1260

His Tyr Leu Asp Glu Ile Ile Glu Gln Ile Ser Glu Phe Ser Lys
1265 1270 1275

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 5
<211> LENGTH: 1368
<212> TYPE: PRT
<213> ORGANISM: Artificial sequence
<220> FEATURE:

<223> OTHER INFORMATION: SpCas9 D10A

<400> SEQUENCE: 5

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp
275 280 285

Leu Phe Leu Ala Ala Lys Asn Leu Ser Asp Ala Ile Leu Leu Ser Asp
290 295 300

Ile Leu Arg Val Asn Thr Glu Ile Thr Lys Ala Pro Leu Ser Ala Ser
305 310 315 320

Met Ile Lys Arg Tyr Asp Glu His His Gln Asp Leu Thr Leu Leu Lys
325 330 335

Ala Leu Val Arg Gln Gln Leu Pro Glu Lys Tyr Lys Glu Ile Phe Phe
340 345 350

Asp Gln Ser Lys Asn Gly Tyr Ala Gly Tyr Ile Asp Gly Gly Ala Ser
355 360 365

Gln Glu Glu Phe Tyr Lys Phe Ile Lys Pro Ile Leu Glu Lys Met Asp
370 375 380

Gly Thr Glu Glu Leu Leu Val Lys Leu Asn Arg Glu Asp Leu Leu Arg
385 390 395 400

-continued

```
Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
```

-continued

```
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230
```

```
Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365


<210> SEQ ID NO 6
<211> LENGTH: 1368
<212> TYPE: PRT
<213> ORGANISM: Artificial sequence
<220> FEATURE:
<223> OTHER INFORMATION: SpCas9 H840A

<400> SEQUENCE: 6

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220
```

-continued

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp
275 280 285

Leu Phe Leu Ala Ala Lys Asn Leu Ser Asp Ala Ile Leu Leu Ser Asp
290 295 300

Ile Leu Arg Val Asn Thr Glu Ile Thr Lys Ala Pro Leu Ser Ala Ser
305 310 315 320

Met Ile Lys Arg Tyr Asp Glu His His Gln Asp Leu Thr Leu Leu Lys
325 330 335

Ala Leu Val Arg Gln Gln Leu Pro Glu Lys Tyr Lys Glu Ile Phe Phe
340 345 350

Asp Gln Ser Lys Asn Gly Tyr Ala Gly Tyr Ile Asp Gly Gly Ala Ser
355 360 365

Gln Glu Glu Phe Tyr Lys Phe Ile Lys Pro Ile Leu Glu Lys Met Asp
370 375 380

Gly Thr Glu Glu Leu Leu Val Lys Leu Asn Arg Glu Asp Leu Leu Arg
385 390 395 400

Lys Gln Arg Thr Phe Asp Asn Gly Ser Ile Pro His Gln Ile His Leu
405 410 415

Gly Glu Leu His Ala Ile Leu Arg Arg Gln Glu Asp Phe Tyr Pro Phe
420 425 430

Leu Lys Asp Asn Arg Glu Lys Ile Glu Lys Ile Leu Thr Phe Arg Ile
435 440 445

Pro Tyr Tyr Val Gly Pro Leu Ala Arg Gly Asn Ser Arg Phe Ala Trp
450 455 460

Met Thr Arg Lys Ser Glu Glu Thr Ile Thr Pro Trp Asn Phe Glu Glu
465 470 475 480

Val Val Asp Lys Gly Ala Ser Ala Gln Ser Phe Ile Glu Arg Met Thr
485 490 495

Asn Phe Asp Lys Asn Leu Pro Asn Glu Lys Val Leu Pro Lys His Ser
500 505 510

Leu Leu Tyr Glu Tyr Phe Thr Val Tyr Asn Glu Leu Thr Lys Val Lys
515 520 525

Tyr Val Thr Glu Gly Met Arg Lys Pro Ala Phe Leu Ser Gly Glu Gln
530 535 540

Lys Lys Ala Ile Val Asp Leu Leu Phe Lys Thr Asn Arg Lys Val Thr
545 550 555 560

Val Lys Gln Leu Lys Glu Asp Tyr Phe Lys Lys Ile Glu Cys Phe Asp
565 570 575

Ser Val Glu Ile Ser Gly Val Glu Asp Arg Phe Asn Ala Ser Leu Gly
580 585 590

Thr Tyr His Asp Leu Leu Lys Ile Ile Lys Asp Lys Asp Phe Leu Asp
595 600 605

Asn Glu Glu Asn Glu Asp Ile Leu Glu Asp Ile Val Leu Thr Leu Thr
610 615 620

Leu Phe Glu Asp Arg Glu Met Ile Glu Glu Arg Leu Lys Thr Tyr Ala
625 630 635 640

-continued

```
His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
```

```
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365


<210> SEQ ID NO 7
<211> LENGTH: 1368
<212> TYPE: PRT
<213> ORGANISM: Artificial sequence
<220> FEATURE:
<223> OTHER INFORMATION: SpCas9 D10A; H840A

<400> SEQUENCE: 7

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
```

-continued

```
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460
```

-continued

```
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880
```

-continued

```
Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
```

-continued 1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 8
<211> LENGTH: 1368
<212> TYPE: PRT
<213> ORGANISM: Artificial sequence
<220> FEATURE:
<223> OTHER INFORMATION: nCas9 with K848A/K1003A/R1060A mutations

<400> SEQUENCE: 8

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp

-continued

```
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700
```

-continued

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Ala
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Ala Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Ala  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110
```

-continued

Arg Asn Ser Asp Lys Leu Ile Ala Arg Lys Lys Asp Trp Asp Pro
1115 1120 1125

Lys Lys Tyr Gly Gly Phe Asp Ser Pro Thr Val Ala Tyr Ser Val
1130 1135 1140

Leu Val Val Ala Lys Val Glu Lys Gly Lys Ser Lys Lys Leu Lys
1145 1150 1155

Ser Val Lys Glu Leu Leu Gly Ile Thr Ile Met Glu Arg Ser Ser
1160 1165 1170

Phe Glu Lys Asn Pro Ile Asp Phe Leu Glu Ala Lys Gly Tyr Lys
1175 1180 1185

Glu Val Lys Lys Asp Leu Ile Ile Lys Leu Pro Lys Tyr Ser Leu
1190 1195 1200

Phe Glu Leu Glu Asn Gly Arg Lys Arg Met Leu Ala Ser Ala Gly
1205 1210 1215

Glu Leu Gln Lys Gly Asn Glu Leu Ala Leu Pro Ser Lys Tyr Val
1220 1225 1230

Asn Phe Leu Tyr Leu Ala Ser His Tyr Glu Lys Leu Lys Gly Ser
1235 1240 1245

Pro Glu Asp Asn Glu Gln Lys Gln Leu Phe Val Glu Gln His Lys
1250 1255 1260

His Tyr Leu Asp Glu Ile Ile Glu Gln Ile Ser Glu Phe Ser Lys
1265 1270 1275

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 9
<211> LENGTH: 1367
<212> TYPE: PRT
<213> ORGANISM: Artificial sequence
<220> FEATURE:
<223> OTHER INFORMATION: nSpCas9-HF1

<400> SEQUENCE: 9

Asp Lys Lys Tyr Ser Ile Gly Leu Ala Ile Gly Thr Asn Ser Val Gly
1 5 10 15

Trp Ala Val Ile Thr Asp Glu Tyr Lys Val Pro Ser Lys Lys Phe Lys
20 25 30

Val Leu Gly Asn Thr Asp Arg His Ser Ile Lys Lys Asn Leu Ile Gly
35 40 45

Ala Leu Leu Phe Asp Ser Gly Glu Thr Ala Glu Ala Thr Arg Leu Lys
50 55 60

Arg Thr Ala Arg Arg Arg Tyr Thr Arg Arg Lys Asn Arg Ile Cys Tyr
65 70 75 80

Leu Gln Glu Ile Phe Ser Asn Glu Met Ala Lys Val Asp Asp Ser Phe
85 90 95

-continued

```
Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Ala
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
```

-continued

```
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Ala Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Ala Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Ala Ile Thr Lys
        915                 920                 925

His Val Ala Gln Ile Leu Asp Ser Arg Met Asn Thr Lys Tyr Asp Glu
    930                 935                 940
```

-continued

```
Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                 1015                1020

Ser Glu  Gln Glu Ile Gly Lys  Ala Thr Ala Lys Tyr  Phe Phe Tyr
    1025                 1030                1035

Ser Asn  Ile Met Asn Phe Phe  Lys Thr Glu Ile Thr  Leu Ala Asn
    1040                 1045                1050

Gly Glu  Ile Arg Lys Arg Pro  Leu Ile Glu Thr Asn  Gly Glu Thr
    1055                 1060                1065

Gly Glu  Ile Val Trp Asp Lys  Gly Arg Asp Phe Ala  Thr Val Arg
    1070                 1075                1080

Lys Val  Leu Ser Met Pro Gln  Val Asn Ile Val Lys  Lys Thr Glu
    1085                 1090                1095

Val Gln  Thr Gly Gly Phe Ser  Lys Glu Ser Ile Leu  Pro Lys Arg
    1100                 1105                1110

Asn Ser  Asp Lys Leu Ile Ala  Arg Lys Lys Asp Trp  Asp Pro Lys
    1115                 1120                1125

Lys Tyr  Gly Gly Phe Asp Ser  Pro Thr Val Ala Tyr  Ser Val Leu
    1130                 1135                1140

Val Val  Ala Lys Val Glu Lys  Gly Lys Ser Lys Lys  Leu Lys Ser
    1145                 1150                1155

Val Lys  Glu Leu Leu Gly Ile  Thr Ile Met Glu Arg  Ser Ser Phe
    1160                 1165                1170

Glu Lys  Asn Pro Ile Asp Phe  Leu Glu Ala Lys Gly  Tyr Lys Glu
    1175                 1180                1185

Val Lys  Lys Asp Leu Ile Ile  Lys Leu Pro Lys Tyr  Ser Leu Phe
    1190                 1195                1200

Glu Leu  Glu Asn Gly Arg Lys  Arg Met Leu Ala Ser  Ala Gly Glu
    1205                 1210                1215

Leu Gln  Lys Gly Asn Glu Leu  Ala Leu Pro Ser Lys  Tyr Val Asn
    1220                 1225                1230

Phe Leu  Tyr Leu Ala Ser His  Tyr Glu Lys Leu Lys  Gly Ser Pro
    1235                 1240                1245

Glu Asp  Asn Glu Gln Lys Gln  Leu Phe Val Glu Gln  His Lys His
    1250                 1255                1260

Tyr Leu  Asp Glu Ile Ile Glu  Gln Ile Ser Glu Phe  Ser Lys Arg
    1265                 1270                1275

Val Ile  Leu Ala Asp Ala Asn  Leu Asp Lys Val Leu  Ser Ala Tyr
    1280                 1285                1290

Asn Lys  His Arg Asp Lys Pro  Ile Arg Glu Gln Ala  Glu Asn Ile
    1295                 1300                1305

Ile His  Leu Phe Thr Leu Thr  Asn Leu Gly Ala Pro  Ala Ala Phe
    1310                 1315                1320

Lys Tyr  Phe Asp Thr Thr Ile  Asp Arg Lys Arg Tyr  Thr Ser Thr
    1325                 1330                1335
```

-continued

```
Lys Glu  Val Leu Asp Ala Thr  Leu Ile His Gln Ser  Ile Thr Gly
    1340                1345                1350

Leu Tyr  Glu Thr Arg Ile Asp  Leu Ser Gln Leu Gly  Gly Asp
    1355                1360                1365


<210> SEQ ID NO 10
<211> LENGTH: 1053
<212> TYPE: PRT
<213> ORGANISM: Staphylococcus aureus

<400> SEQUENCE: 10

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350
```

-continued

```
Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765
```

```
Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
        995                 1000                1005

Asn Asp  Lys Arg Pro Pro Arg  Ile Ile Lys Thr Ile  Ala Ser Lys
    1010                1015                1020

Thr Gln  Ser Ile Lys Lys Tyr  Ser Thr Asp Ile Leu  Gly Asn Leu
    1025                1030                1035

Tyr Glu  Val Lys Ser Lys Lys  His Pro Gln Ile Ile  Lys Lys Gly
    1040                1045                1050
```

<210> SEQ ID NO 11
<211> LENGTH: 1300
<212> TYPE: PRT
<213> ORGANISM: Francisella tularensis

<400> SEQUENCE: 11

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95
```

-continued

```
Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510
```

-continued

```
Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
```

```
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
    1085                1090                1095

Tyr Glu  Ser Val Ser Lys Ser  Gln Glu Phe Phe Ser  Lys Phe Asp
    1100                1105                1110

Lys Ile  Cys Tyr Asn Leu Asp  Lys Gly Tyr Phe Glu  Phe Ser Phe
    1115                1120                1125

Asp Tyr  Lys Asn Phe Gly Asp  Lys Ala Ala Lys Gly  Lys Trp Thr
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170

Leu Glu  Lys Leu Leu Lys Asp  Tyr Ser Ile Glu Tyr  Gly His Gly
    1175                1180                1185

Glu Cys  Ile Lys Ala Ala Ile  Cys Gly Glu Ser Asp  Lys Lys Phe
    1190                1195                1200

Phe Ala  Lys Leu Thr Ser Val  Leu Asn Thr Ile Leu  Gln Met Arg
    1205                1210                1215

Asn Ser  Lys Thr Gly Thr Glu  Leu Asp Tyr Leu Ile  Ser Pro Val
    1220                1225                1230

Ala Asp  Val Asn Gly Asn Phe  Phe Asp Ser Arg Gln  Ala Pro Lys
    1235                1240                1245

Asn Met  Pro Gln Asp Ala Asp  Ala Asn Gly Ala Tyr  His Ile Gly
    1250                1255                1260

Leu Lys  Gly Leu Met Leu Leu  Gly Arg Ile Lys Asn  Asn Gln Glu
    1265                1270                1275

Gly Lys  Lys Leu Asn Leu Val  Ile Lys Asn Glu Glu  Tyr Phe Glu
    1280                1285                1290

Phe Val  Gln Asn Arg Asn Asn
    1295                1300
```

<210> SEQ ID NO 12
<211> LENGTH: 1306
<212> TYPE: PRT
<213> ORGANISM: Acidaminococcus sp.

<400> SEQUENCE: 12

Thr Gln Phe Glu Gly Phe Thr Asn Leu Tyr Gln Val Ser Lys Thr Leu
1 5 10 15

Arg Phe Glu Leu Ile Pro Gln Gly Lys Thr Leu Lys His Ile Gln Glu
20 25 30

Gln Gly Phe Ile Glu Glu Asp Lys Ala Arg Asn Asp His Tyr Lys Glu
35 40 45

Leu Lys Pro Ile Ile Asp Arg Ile Tyr Lys Thr Tyr Ala Asp Gln Cys
50 55 60

Leu Gln Leu Val Gln Leu Asp Trp Glu Asn Leu Ser Ala Ala Ile Asp
65 70 75 80

Ser Tyr Arg Lys Glu Lys Thr Glu Glu Thr Arg Asn Ala Leu Ile Glu
85 90 95

Glu Gln Ala Thr Tyr Arg Asn Ala Ile His Asp Tyr Phe Ile Gly Arg
100 105 110

Thr Asp Asn Leu Thr Asp Ala Ile Asn Lys Arg His Ala Glu Ile Tyr
115 120 125

Lys Gly Leu Phe Lys Ala Glu Leu Phe Asn Gly Lys Val Leu Lys Gln
130 135 140

Leu Gly Thr Val Thr Thr Thr Glu His Glu Asn Ala Leu Leu Arg Ser
145 150 155 160

Phe Asp Lys Phe Thr Thr Tyr Phe Ser Gly Phe Tyr Glu Asn Arg Lys
165 170 175

Asn Val Phe Ser Ala Glu Asp Ile Ser Thr Ala Ile Pro His Arg Ile
180 185 190

Val Gln Asp Asn Phe Pro Lys Phe Lys Glu Asn Cys His Ile Phe Thr
195 200 205

Arg Leu Ile Thr Ala Val Pro Ser Leu Arg Glu His Phe Glu Asn Val
210 215 220

Lys Lys Ala Ile Gly Ile Phe Val Ser Thr Ser Ile Glu Glu Val Phe
225 230 235 240

Ser Phe Pro Phe Tyr Asn Gln Leu Leu Thr Gln Thr Gln Ile Asp Leu
245 250 255

Tyr Asn Gln Leu Leu Gly Gly Ile Ser Arg Glu Ala Gly Thr Glu Lys
260 265 270

Ile Lys Gly Leu Asn Glu Val Leu Asn Leu Ala Ile Gln Lys Asn Asp
275 280 285

Glu Thr Ala His Ile Ile Ala Ser Leu Pro His Arg Phe Ile Pro Leu
290 295 300

Phe Lys Gln Ile Leu Ser Asp Arg Asn Thr Leu Ser Phe Ile Leu Glu
305 310 315 320

Glu Phe Lys Ser Asp Glu Glu Val Ile Gln Ser Phe Cys Lys Tyr Lys
325 330 335

Thr Leu Leu Arg Asn Glu Asn Val Leu Glu Thr Ala Glu Ala Leu Phe
340 345 350

Asn Glu Leu Asn Ser Ile Asp Leu Thr His Ile Phe Ile Ser His Lys
355 360 365

Lys Leu Glu Thr Ile Ser Ser Ala Leu Cys Asp His Trp Asp Thr Leu
370 375 380

Arg Asn Ala Leu Tyr Glu Arg Arg Ile Ser Glu Leu Thr Gly Lys Ile
385 390 395 400

Thr Lys Ser Ala Lys Glu Lys Val Gln Arg Ser Leu Lys His Glu Asp

-continued 405 410 415

Ile Asn Leu Gln Glu Ile Ile Ser Ala Ala Gly Lys Glu Leu Ser Glu
420 425 430

Ala Phe Lys Gln Lys Thr Ser Glu Ile Leu Ser His Ala His Ala Ala
435 440 445

Leu Asp Gln Pro Leu Pro Thr Thr Leu Lys Lys Gln Glu Glu Lys Glu
450 455 460

Ile Leu Lys Ser Gln Leu Asp Ser Leu Leu Gly Leu Tyr His Leu Leu
465 470 475 480

Asp Trp Phe Ala Val Asp Glu Ser Asn Glu Val Asp Pro Glu Phe Ser
485 490 495

Ala Arg Leu Thr Gly Ile Lys Leu Glu Met Glu Pro Ser Leu Ser Phe
500 505 510

Tyr Asn Lys Ala Arg Asn Tyr Ala Thr Lys Lys Pro Tyr Ser Val Glu
515 520 525

Lys Phe Lys Leu Asn Phe Gln Met Pro Thr Leu Ala Ser Gly Trp Asp
530 535 540

Val Asn Lys Glu Lys Asn Asn Gly Ala Ile Leu Phe Val Lys Asn Gly
545 550 555 560

Leu Tyr Tyr Leu Gly Ile Met Pro Lys Gln Lys Gly Arg Tyr Lys Ala
565 570 575

Leu Ser Phe Glu Pro Thr Glu Lys Thr Ser Glu Gly Phe Asp Lys Met
580 585 590

Tyr Tyr Asp Tyr Phe Pro Asp Ala Ala Lys Met Ile Pro Lys Cys Ser
595 600 605

Thr Gln Leu Lys Ala Val Thr Ala His Phe Gln Thr His Thr Thr Pro
610 615 620

Ile Leu Leu Ser Asn Asn Phe Ile Glu Pro Leu Glu Ile Thr Lys Glu
625 630 635 640

Ile Tyr Asp Leu Asn Asn Pro Glu Lys Glu Pro Lys Lys Phe Gln Thr
645 650 655

Ala Tyr Ala Lys Lys Thr Gly Asp Gln Lys Gly Tyr Arg Glu Ala Leu
660 665 670

Cys Lys Trp Ile Asp Phe Thr Arg Asp Phe Leu Ser Lys Tyr Thr Lys
675 680 685

Thr Thr Ser Ile Asp Leu Ser Ser Leu Arg Pro Ser Ser Gln Tyr Lys
690 695 700

Asp Leu Gly Glu Tyr Tyr Ala Glu Leu Asn Pro Leu Leu Tyr His Ile
705 710 715 720

Ser Phe Gln Arg Ile Ala Glu Lys Glu Ile Met Asp Ala Val Glu Thr
725 730 735

Gly Lys Leu Tyr Leu Phe Gln Ile Tyr Asn Lys Asp Phe Ala Lys Gly
740 745 750

His His Gly Lys Pro Asn Leu His Thr Leu Tyr Trp Thr Gly Leu Phe
755 760 765

Ser Pro Glu Asn Leu Ala Lys Thr Ser Ile Lys Leu Asn Gly Gln Ala
770 775 780

Glu Leu Phe Tyr Arg Pro Lys Ser Arg Met Lys Arg Met Ala His Arg
785 790 795 800

Leu Gly Glu Lys Met Leu Asn Lys Lys Leu Lys Asp Gln Lys Thr Pro
805 810 815

Ile Pro Asp Thr Leu Tyr Gln Glu Leu Tyr Asp Tyr Val Asn His Arg
820 825 830

```
Leu Ser His Asp Leu Ser Asp Glu Ala Arg Ala Leu Leu Pro Asn Val
        835                 840                 845

Ile Thr Lys Glu Val Ser His Glu Ile Ile Lys Asp Arg Arg Phe Thr
    850                 855                 860

Ser Asp Lys Phe Phe Phe His Val Pro Ile Thr Leu Asn Tyr Gln Ala
865                 870                 875                 880

Ala Asn Ser Pro Ser Lys Phe Asn Gln Arg Val Asn Ala Tyr Leu Lys
                885                 890                 895

Glu His Pro Glu Thr Pro Ile Ile Gly Ile Asp Arg Gly Glu Arg Asn
            900                 905                 910

Leu Ile Tyr Ile Thr Val Ile Asp Ser Thr Gly Lys Ile Leu Glu Gln
        915                 920                 925

Arg Ser Leu Asn Thr Ile Gln Gln Phe Asp Tyr Gln Lys Lys Leu Asp
    930                 935                 940

Asn Arg Glu Lys Glu Arg Val Ala Ala Arg Gln Ala Trp Ser Val Val
945                 950                 955                 960

Gly Thr Ile Lys Asp Leu Lys Gln Gly Tyr Leu Ser Gln Val Ile His
                965                 970                 975

Glu Ile Val Asp Leu Met Ile His Tyr Gln Ala Val Val Val Leu Glu
            980                 985                 990

Asn Leu Asn Phe Gly Phe Lys Ser  Lys Arg Thr Gly Ile  Ala Glu Lys
        995                 1000                1005

Ala Val  Tyr Gln Gln Phe Glu  Lys Met Leu Ile Asp  Lys Leu Asn
    1010                 1015                 1020

Cys Leu  Val Leu Lys Asp Tyr  Pro Ala Glu Lys Val  Gly Gly Val
    1025                 1030                 1035

Leu Asn  Pro Tyr Gln Leu Thr  Asp Gln Phe Thr Ser  Phe Ala Lys
    1040                 1045                 1050

Met Gly  Thr Gln Ser Gly Phe  Leu Phe Tyr Val Pro  Ala Pro Tyr
    1055                 1060                 1065

Thr Ser  Lys Ile Asp Pro Leu  Thr Gly Phe Val Asp  Pro Phe Val
    1070                 1075                 1080

Trp Lys  Thr Ile Lys Asn His  Glu Ser Arg Lys His  Phe Leu Glu
    1085                 1090                 1095

Gly Phe  Asp Phe Leu His Tyr  Asp Val Lys Thr Gly  Asp Phe Ile
    1100                 1105                 1110

Leu His  Phe Lys Met Asn Arg  Asn Leu Ser Phe Gln  Arg Gly Leu
    1115                 1120                 1125

Pro Gly  Phe Met Pro Ala Trp  Asp Ile Val Phe Glu  Lys Asn Glu
    1130                 1135                 1140

Thr Gln  Phe Asp Ala Lys Gly  Thr Pro Phe Ile Ala  Gly Lys Arg
    1145                 1150                 1155

Ile Val  Pro Val Ile Glu Asn  His Arg Phe Thr Gly  Arg Tyr Arg
    1160                 1165                 1170

Asp Leu  Tyr Pro Ala Asn Glu  Leu Ile Ala Leu Leu  Glu Glu Lys
    1175                 1180                 1185

Gly Ile  Val Phe Arg Asp Gly  Ser Asn Ile Leu Pro  Lys Leu Leu
    1190                 1195                 1200

Glu Asn  Asp Asp Ser His Ala  Ile Asp Thr Met Val  Ala Leu Ile
    1205                 1210                 1215

Arg Ser  Val Leu Gln Met Arg  Asn Ser Asn Ala Ala  Thr Gly Glu
    1220                 1225                 1230
```

-continued

Asp Tyr Ile Asn Ser Pro Val Arg Asp Leu Asn Gly Val Cys Phe
1235 1240 1245

Asp Ser Arg Phe Gln Asn Pro Glu Trp Pro Met Asp Ala Asp Ala
1250 1255 1260

Asn Gly Ala Tyr His Ile Ala Leu Lys Gly Gln Leu Leu Leu Asn
1265 1270 1275

His Leu Lys Glu Ser Lys Asp Leu Lys Leu Gln Asn Gly Ile Ser
1280 1285 1290

Asn Gln Asp Trp Leu Ala Tyr Ile Gln Glu Leu Arg Asn
1295 1300 1305

<210> SEQ ID NO 13
<211> LENGTH: 1306
<212> TYPE: PRT
<213> ORGANISM: Artificial sequence
<220> FEATURE:
<223> OTHER INFORMATION: AsCpf1 R1225A

<400> SEQUENCE: 13

Thr Gln Phe Glu Gly Phe Thr Asn Leu Tyr Gln Val Ser Lys Thr Leu
1 5 10 15

Arg Phe Glu Leu Ile Pro Gln Gly Lys Thr Leu Lys His Ile Gln Glu
20 25 30

Gln Gly Phe Ile Glu Glu Asp Lys Ala Arg Asn Asp His Tyr Lys Glu
35 40 45

Leu Lys Pro Ile Ile Asp Arg Ile Tyr Lys Thr Tyr Ala Asp Gln Cys
50 55 60

Leu Gln Leu Val Gln Leu Asp Trp Glu Asn Leu Ser Ala Ala Ile Asp
65 70 75 80

Ser Tyr Arg Lys Glu Lys Thr Glu Glu Thr Arg Asn Ala Leu Ile Glu
85 90 95

Glu Gln Ala Thr Tyr Arg Asn Ala Ile His Asp Tyr Phe Ile Gly Arg
100 105 110

Thr Asp Asn Leu Thr Asp Ala Ile Asn Lys Arg His Ala Glu Ile Tyr
115 120 125

Lys Gly Leu Phe Lys Ala Glu Leu Phe Asn Gly Lys Val Leu Lys Gln
130 135 140

Leu Gly Thr Val Thr Thr Thr Glu His Glu Asn Ala Leu Leu Arg Ser
145 150 155 160

Phe Asp Lys Phe Thr Thr Tyr Phe Ser Gly Phe Tyr Glu Asn Arg Lys
165 170 175

Asn Val Phe Ser Ala Glu Asp Ile Ser Thr Ala Ile Pro His Arg Ile
180 185 190

Val Gln Asp Asn Phe Pro Lys Phe Lys Glu Asn Cys His Ile Phe Thr
195 200 205

Arg Leu Ile Thr Ala Val Pro Ser Leu Arg Glu His Phe Glu Asn Val
210 215 220

Lys Lys Ala Ile Gly Ile Phe Val Ser Thr Ser Ile Glu Glu Val Phe
225 230 235 240

Ser Phe Pro Phe Tyr Asn Gln Leu Leu Thr Gln Thr Gln Ile Asp Leu
245 250 255

Tyr Asn Gln Leu Leu Gly Gly Ile Ser Arg Glu Ala Gly Thr Glu Lys
260 265 270

Ile Lys Gly Leu Asn Glu Val Leu Asn Leu Ala Ile Gln Lys Asn Asp
275 280 285

-continued

Glu Thr Ala His Ile Ile Ala Ser Leu Pro His Arg Phe Ile Pro Leu
    290                 295                 300

Phe Lys Gln Ile Leu Ser Asp Arg Asn Thr Leu Ser Phe Ile Leu Glu
305                 310                 315                 320

Glu Phe Lys Ser Asp Glu Glu Val Ile Gln Ser Phe Cys Lys Tyr Lys
                325                 330                 335

Thr Leu Leu Arg Asn Glu Asn Val Leu Glu Thr Ala Glu Ala Leu Phe
            340                 345                 350

Asn Glu Leu Asn Ser Ile Asp Leu Thr His Ile Phe Ile Ser His Lys
        355                 360                 365

Lys Leu Glu Thr Ile Ser Ser Ala Leu Cys Asp His Trp Asp Thr Leu
    370                 375                 380

Arg Asn Ala Leu Tyr Glu Arg Arg Ile Ser Glu Leu Thr Gly Lys Ile
385                 390                 395                 400

Thr Lys Ser Ala Lys Glu Lys Val Gln Arg Ser Leu Lys His Glu Asp
                405                 410                 415

Ile Asn Leu Gln Glu Ile Ile Ser Ala Ala Gly Lys Glu Leu Ser Glu
            420                 425                 430

Ala Phe Lys Gln Lys Thr Ser Glu Ile Leu Ser His Ala His Ala Ala
        435                 440                 445

Leu Asp Gln Pro Leu Pro Thr Thr Leu Lys Lys Gln Glu Glu Lys Glu
    450                 455                 460

Ile Leu Lys Ser Gln Leu Asp Ser Leu Leu Gly Leu Tyr His Leu Leu
465                 470                 475                 480

Asp Trp Phe Ala Val Asp Glu Ser Asn Glu Val Asp Pro Glu Phe Ser
                485                 490                 495

Ala Arg Leu Thr Gly Ile Lys Leu Glu Met Glu Pro Ser Leu Ser Phe
            500                 505                 510

Tyr Asn Lys Ala Arg Asn Tyr Ala Thr Lys Lys Pro Tyr Ser Val Glu
        515                 520                 525

Lys Phe Lys Leu Asn Phe Gln Met Pro Thr Leu Ala Ser Gly Trp Asp
    530                 535                 540

Val Asn Lys Glu Lys Asn Asn Gly Ala Ile Leu Phe Val Lys Asn Gly
545                 550                 555                 560

Leu Tyr Tyr Leu Gly Ile Met Pro Lys Gln Lys Gly Arg Tyr Lys Ala
                565                 570                 575

Leu Ser Phe Glu Pro Thr Glu Lys Thr Ser Glu Gly Phe Asp Lys Met
            580                 585                 590

Tyr Tyr Asp Tyr Phe Pro Asp Ala Ala Lys Met Ile Pro Lys Cys Ser
        595                 600                 605

Thr Gln Leu Lys Ala Val Thr Ala His Phe Gln Thr His Thr Thr Pro
    610                 615                 620

Ile Leu Leu Ser Asn Asn Phe Ile Glu Pro Leu Glu Ile Thr Lys Glu
625                 630                 635                 640

Ile Tyr Asp Leu Asn Asn Pro Glu Lys Glu Pro Lys Lys Phe Gln Thr
                645                 650                 655

Ala Tyr Ala Lys Lys Thr Gly Asp Gln Lys Gly Tyr Arg Glu Ala Leu
            660                 665                 670

Cys Lys Trp Ile Asp Phe Thr Arg Asp Phe Leu Ser Lys Tyr Thr Lys
        675                 680                 685

Thr Thr Ser Ile Asp Leu Ser Ser Leu Arg Pro Ser Ser Gln Tyr Lys
    690                 695                 700

Asp Leu Gly Glu Tyr Tyr Ala Glu Leu Asn Pro Leu Leu Tyr His Ile

-continued

```
705                 710                 715                 720

Ser Phe Gln Arg Ile Ala Glu Lys Glu Ile Met Asp Ala Val Glu Thr
                725                 730                 735

Gly Lys Leu Tyr Leu Phe Gln Ile Tyr Asn Lys Asp Phe Ala Lys Gly
            740                 745                 750

His His Gly Lys Pro Asn Leu His Thr Leu Tyr Trp Thr Gly Leu Phe
        755                 760                 765

Ser Pro Glu Asn Leu Ala Lys Thr Ser Ile Lys Leu Asn Gly Gln Ala
    770                 775                 780

Glu Leu Phe Tyr Arg Pro Lys Ser Arg Met Lys Arg Met Ala His Arg
785                 790                 795                 800

Leu Gly Glu Lys Met Leu Asn Lys Lys Leu Lys Asp Gln Lys Thr Pro
                805                 810                 815

Ile Pro Asp Thr Leu Tyr Gln Glu Leu Tyr Asp Tyr Val Asn His Arg
            820                 825                 830

Leu Ser His Asp Leu Ser Asp Glu Ala Arg Ala Leu Leu Pro Asn Val
        835                 840                 845

Ile Thr Lys Glu Val Ser His Glu Ile Ile Lys Asp Arg Arg Phe Thr
    850                 855                 860

Ser Asp Lys Phe Phe Phe His Val Pro Ile Thr Leu Asn Tyr Gln Ala
865                 870                 875                 880

Ala Asn Ser Pro Ser Lys Phe Asn Gln Arg Val Asn Ala Tyr Leu Lys
                885                 890                 895

Glu His Pro Glu Thr Pro Ile Ile Gly Ile Asp Arg Gly Glu Arg Asn
            900                 905                 910

Leu Ile Tyr Ile Thr Val Ile Asp Ser Thr Gly Lys Ile Leu Glu Gln
        915                 920                 925

Arg Ser Leu Asn Thr Ile Gln Gln Phe Asp Tyr Gln Lys Lys Leu Asp
    930                 935                 940

Asn Arg Glu Lys Glu Arg Val Ala Ala Arg Gln Ala Trp Ser Val Val
945                 950                 955                 960

Gly Thr Ile Lys Asp Leu Lys Gln Gly Tyr Leu Ser Gln Val Ile His
                965                 970                 975

Glu Ile Val Asp Leu Met Ile His Tyr Gln Ala Val Val Val Leu Glu
            980                 985                 990

Asn Leu Asn Phe Gly Phe Lys Ser  Lys Arg Thr Gly Ile  Ala Glu Lys
        995                 1000                1005

Ala Val  Tyr Gln Gln Phe Glu  Lys Met Leu Ile Asp  Lys Leu Asn
    1010                 1015                 1020

Cys Leu  Val Leu Lys Asp Tyr  Pro Ala Glu Lys Val  Gly Gly Val
    1025                 1030                 1035

Leu Asn  Pro Tyr Gln Leu Thr  Asp Gln Phe Thr Ser  Phe Ala Lys
    1040                 1045                 1050

Met Gly  Thr Gln Ser Gly Phe  Leu Phe Tyr Val Pro  Ala Pro Tyr
    1055                 1060                 1065

Thr Ser  Lys Ile Asp Pro Leu  Thr Gly Phe Val Asp  Pro Phe Val
    1070                 1075                 1080

Trp Lys  Thr Ile Lys Asn His  Glu Ser Arg Lys His  Phe Leu Glu
    1085                 1090                 1095

Gly Phe  Asp Phe Leu His Tyr  Asp Val Lys Thr Gly  Asp Phe Ile
    1100                 1105                 1110

Leu His  Phe Lys Met Asn Arg  Asn Leu Ser Phe Gln  Arg Gly Leu
    1115                 1120                 1125
```

```
Pro Gly  Phe Met Pro Ala Trp  Asp Ile Val Phe Glu  Lys Asn Glu
    1130                 1135                 1140

Thr Gln  Phe Asp Ala Lys Gly  Thr Pro Phe Ile Ala  Gly Lys Arg
    1145                 1150                 1155

Ile Val  Pro Val Ile Glu Asn  His Arg Phe Thr Gly  Arg Tyr Arg
    1160                 1165                 1170

Asp Leu  Tyr Pro Ala Asn Glu  Leu Ile Ala Leu Leu  Glu Glu Lys
    1175                 1180                 1185

Gly Ile  Val Phe Arg Asp Gly  Ser Asn Ile Leu Pro  Lys Leu Leu
    1190                 1195                 1200

Glu Asn  Asp Asp Ser His Ala  Ile Asp Thr Met Val  Ala Leu Ile
    1205                 1210                 1215

Arg Ser  Val Leu Gln Met Ala  Asn Ser Asn Ala Ala  Thr Gly Glu
    1220                 1225                 1230

Asp Tyr  Ile Asn Ser Pro Val  Arg Asp Leu Asn Gly  Val Cys Phe
    1235                 1240                 1245

Asp Ser  Arg Phe Gln Asn Pro  Glu Trp Pro Met Asp  Ala Asp Ala
    1250                 1255                 1260

Asn Gly  Ala Tyr His Ile Ala  Leu Lys Gly Gln Leu  Leu Leu Asn
    1265                 1270                 1275

His Leu  Lys Glu Ser Lys Asp  Leu Lys Leu Gln Asn  Gly Ile Ser
    1280                 1285                 1290

Asn Gln  Asp Trp Leu Ala Tyr  Ile Gln Glu Leu Arg  Asn
    1295                 1300                 1305
```

<210> SEQ ID NO 14
<211> LENGTH: 1120
<212> TYPE: PRT
<213> ORGANISM: Listeria seeligeri

<400> SEQUENCE: 14

```
Met Trp Ile Ser Ile Lys Thr Leu Ile His His Leu Gly Val Leu Phe
1               5                   10                  15

Phe Cys Asp Tyr Met Tyr Asn Arg Arg Glu Lys Lys Ile Ile Glu Val
            20                  25                  30

Lys Thr Met Arg Ile Thr Lys Val Glu Val Asp Arg Lys Lys Val Leu
        35                  40                  45

Ile Ser Arg Asp Lys Asn Gly Gly Lys Leu Val Tyr Glu Asn Glu Met
    50                  55                  60

Gln Asp Asn Thr Glu Gln Ile Met His His Lys Lys Ser Ser Phe Tyr
65                  70                  75                  80

Lys Ser Val Val Asn Lys Thr Ile Cys Arg Pro Glu Gln Lys Gln Met
                85                  90                  95

Lys Lys Leu Val His Gly Leu Leu Gln Glu Asn Ser Gln Glu Lys Ile
            100                 105                 110

Lys Val Ser Asp Val Thr Lys Leu Asn Ile Ser Asn Phe Leu Asn His
        115                 120                 125

Arg Phe Lys Lys Ser Leu Tyr Tyr Phe Pro Glu Asn Ser Pro Asp Lys
    130                 135                 140

Ser Glu Glu Tyr Arg Ile Glu Ile Asn Leu Ser Gln Leu Leu Glu Asp
145                 150                 155                 160

Ser Leu Lys Lys Gln Gln Gly Thr Phe Ile Cys Trp Glu Ser Phe Ser
                165                 170                 175

Lys Asp Met Glu Leu Tyr Ile Asn Trp Ala Glu Asn Tyr Ile Ser Ser
```

-continued

```
            180                 185                 190

Lys Thr Lys Leu Ile Lys Lys Ser Ile Arg Asn Asn Arg Ile Gln Ser
        195                 200                 205

Thr Glu Ser Arg Ser Gly Gln Leu Met Asp Arg Tyr Met Lys Asp Ile
    210                 215                 220

Leu Asn Lys Asn Lys Pro Phe Asp Ile Gln Ser Val Ser Glu Lys Tyr
225                 230                 235                 240

Gln Leu Glu Lys Leu Thr Ser Ala Leu Lys Ala Thr Phe Lys Glu Ala
                245                 250                 255

Lys Lys Asn Asp Lys Glu Ile Asn Tyr Lys Leu Lys Ser Thr Leu Gln
            260                 265                 270

Asn His Glu Arg Gln Ile Ile Glu Glu Leu Lys Glu Asn Ser Glu Leu
        275                 280                 285

Asn Gln Phe Asn Ile Glu Ile Arg Lys His Leu Glu Thr Tyr Phe Pro
    290                 295                 300

Ile Lys Lys Thr Asn Arg Lys Val Gly Asp Ile Arg Asn Leu Glu Ile
305                 310                 315                 320

Gly Glu Ile Gln Lys Ile Val Asn His Arg Leu Lys Asn Lys Ile Val
                325                 330                 335

Gln Arg Ile Leu Gln Glu Gly Lys Leu Ala Ser Tyr Glu Ile Glu Ser
            340                 345                 350

Thr Val Asn Ser Asn Ser Leu Gln Lys Ile Lys Ile Glu Glu Ala Phe
        355                 360                 365

Ala Leu Lys Phe Ile Asn Ala Cys Leu Phe Ala Ser Asn Asn Leu Arg
    370                 375                 380

Asn Met Val Tyr Pro Val Cys Lys Lys Asp Ile Leu Met Ile Gly Glu
385                 390                 395                 400

Phe Lys Asn Ser Phe Lys Glu Ile Lys His Lys Lys Phe Ile Arg Gln
                405                 410                 415

Trp Ser Gln Phe Phe Ser Gln Glu Ile Thr Val Asp Asp Ile Glu Leu
            420                 425                 430

Ala Ser Trp Gly Leu Arg Gly Ala Ile Ala Pro Ile Arg Asn Glu Ile
        435                 440                 445

Ile His Leu Lys Lys His Ser Trp Lys Lys Phe Phe Asn Asn Pro Thr
    450                 455                 460

Phe Lys Val Lys Lys Ser Lys Ile Ile Asn Gly Lys Thr Lys Asp Val
465                 470                 475                 480

Thr Ser Glu Phe Leu Tyr Lys Glu Thr Leu Phe Lys Asp Tyr Phe Tyr
                485                 490                 495

Ser Glu Leu Asp Ser Val Pro Glu Leu Ile Ile Asn Lys Met Glu Ser
            500                 505                 510

Ser Lys Ile Leu Asp Tyr Tyr Ser Ser Asp Gln Leu Asn Gln Val Phe
        515                 520                 525

Thr Ile Pro Asn Phe Glu Leu Ser Leu Leu Thr Ser Ala Val Pro Phe
    530                 535                 540

Ala Pro Ser Phe Lys Arg Val Tyr Leu Lys Gly Phe Asp Tyr Gln Asn
545                 550                 555                 560

Gln Asp Glu Ala Gln Pro Asp Tyr Asn Leu Lys Leu Asn Ile Tyr Asn
                565                 570                 575

Glu Lys Ala Phe Asn Ser Glu Ala Phe Gln Ala Gln Tyr Ser Leu Phe
            580                 585                 590

Lys Met Val Tyr Tyr Gln Val Phe Leu Pro Gln Phe Thr Thr Asn Asn
        595                 600                 605
```

-continued

```
Asp Leu Phe Lys Ser Ser Val Asp Phe Ile Leu Thr Leu Asn Lys Glu
    610                 615                 620

Arg Lys Gly Tyr Ala Lys Ala Phe Gln Asp Ile Arg Lys Met Asn Lys
625                 630                 635                 640

Asp Glu Lys Pro Ser Glu Tyr Met Ser Tyr Ile Gln Ser Gln Leu Met
                645                 650                 655

Leu Tyr Gln Lys Lys Gln Glu Glu Lys Glu Lys Ile Asn His Phe Glu
            660                 665                 670

Lys Phe Ile Asn Gln Val Phe Ile Lys Gly Phe Asn Ser Phe Ile Glu
        675                 680                 685

Lys Asn Arg Leu Thr Tyr Ile Cys His Pro Thr Lys Asn Thr Val Pro
    690                 695                 700

Glu Asn Asp Asn Ile Glu Ile Pro Phe His Thr Asp Met Asp Asp Ser
705                 710                 715                 720

Asn Ile Ala Phe Trp Leu Met Cys Lys Leu Leu Asp Ala Lys Gln Leu
                725                 730                 735

Ser Glu Leu Arg Asn Glu Met Ile Lys Phe Ser Cys Ser Leu Gln Ser
            740                 745                 750

Thr Glu Glu Ile Ser Thr Phe Thr Lys Ala Arg Glu Val Ile Gly Leu
        755                 760                 765

Ala Leu Leu Asn Gly Glu Lys Gly Cys Asn Asp Trp Lys Glu Leu Phe
    770                 775                 780

Asp Asp Lys Glu Ala Trp Lys Lys Asn Met Ser Leu Tyr Val Ser Glu
785                 790                 795                 800

Glu Leu Leu Gln Ser Leu Pro Tyr Thr Gln Glu Asp Gly Gln Thr Pro
                805                 810                 815

Val Ile Asn Arg Ser Ile Asp Leu Val Lys Lys Tyr Gly Thr Glu Thr
            820                 825                 830

Ile Leu Glu Lys Leu Phe Ser Ser Ser Asp Asp Tyr Lys Val Ser Ala
        835                 840                 845

Lys Asp Ile Ala Lys Leu His Glu Tyr Asp Val Thr Glu Lys Ile Ala
    850                 855                 860

Gln Gln Glu Ser Leu His Lys Gln Trp Ile Glu Lys Pro Gly Leu Ala
865                 870                 875                 880

Arg Asp Ser Ala Trp Thr Lys Lys Tyr Gln Asn Val Ile Asn Asp Ile
                885                 890                 895

Ser Asn Tyr Gln Trp Ala Lys Thr Lys Val Glu Leu Thr Gln Val Arg
            900                 905                 910

His Leu His Gln Leu Thr Ile Asp Leu Leu Ser Arg Leu Ala Gly Tyr
        915                 920                 925

Met Ser Ile Ala Asp Arg Asp Phe Gln Phe Ser Ser Asn Tyr Ile Leu
    930                 935                 940

Glu Arg Glu Asn Ser Glu Tyr Arg Val Thr Ser Trp Ile Leu Leu Ser
945                 950                 955                 960

Glu Asn Lys Asn Lys Asn Lys Tyr Asn Asp Tyr Glu Leu Tyr Asn Leu
                965                 970                 975

Lys Asn Ala Ser Ile Lys Val Ser Ser Lys Asn Asp Pro Gln Leu Lys
            980                 985                 990

Val Asp Leu Lys Gln Leu Arg Leu  Thr Leu Glu Tyr Leu  Glu Leu Phe
        995                 1000                1005

Asp Asn  Arg Leu Lys Glu Lys  Arg Asn Asn Ile Ser  His Phe Asn
    1010                1015                1020
```

Tyr Leu Asn Gly Gln Leu Gly Asn Ser Ile Leu Glu Leu Phe Asp
    1025                1030                1035

Asp Ala Arg Asp Val Leu Ser Tyr Asp Arg Lys Leu Lys Asn Ala
    1040                1045                1050

Val Ser Lys Ser Leu Lys Glu Ile Leu Ser Ser His Gly Met Glu
    1055                1060                1065

Val Thr Phe Lys Pro Leu Tyr Gln Thr Asn His His Leu Lys Ile
    1070                1075                1080

Asp Lys Leu Gln Pro Lys Lys Ile His His Leu Gly Glu Lys Ser
    1085                1090                1095

Thr Val Ser Ser Asn Gln Val Ser Asn Glu Tyr Cys Gln Leu Val
    1100                1105                1110

Arg Thr Leu Leu Thr Met Lys
    1115                1120

<210> SEQ ID NO 15
<211> LENGTH: 1159
<212> TYPE: PRT
<213> ORGANISM: Leptotrichia buccalis

<400> SEQUENCE: 15

Met Lys Val Thr Lys Val Gly Gly Ile Ser His Lys Lys Tyr Thr Ser
1               5                   10                  15

Glu Gly Arg Leu Val Lys Ser Glu Ser Glu Glu Asn Arg Thr Asp Glu
            20                  25                  30

Arg Leu Ser Ala Leu Leu Asn Met Arg Leu Asp Met Tyr Ile Lys Asn
        35                  40                  45

Pro Ser Ser Thr Glu Thr Lys Glu Asn Gln Lys Arg Ile Gly Lys Leu
    50                  55                  60

Lys Lys Phe Phe Ser Asn Lys Met Val Tyr Leu Lys Asp Asn Thr Leu
65                  70                  75                  80

Ser Leu Lys Asn Gly Lys Lys Glu Asn Ile Asp Arg Glu Tyr Ser Glu
                85                  90                  95

Thr Asp Ile Leu Glu Ser Asp Val Arg Asp Lys Lys Asn Phe Ala Val
            100                 105                 110

Leu Lys Lys Ile Tyr Leu Asn Glu Asn Val Asn Ser Glu Glu Leu Glu
        115                 120                 125

Val Phe Arg Asn Asp Ile Lys Lys Lys Leu Asn Lys Ile Asn Ser Leu
    130                 135                 140

Lys Tyr Ser Phe Glu Lys Asn Lys Ala Asn Tyr Gln Lys Ile Asn Glu
145                 150                 155                 160

Asn Asn Ile Glu Lys Val Glu Gly Lys Ser Lys Arg Asn Ile Ile Tyr
                165                 170                 175

Asp Tyr Tyr Arg Glu Ser Ala Lys Arg Asp Ala Tyr Val Ser Asn Val
            180                 185                 190

Lys Glu Ala Phe Asp Lys Leu Tyr Lys Glu Glu Asp Ile Ala Lys Leu
        195                 200                 205

Val Leu Glu Ile Glu Asn Leu Thr Lys Leu Glu Lys Tyr Lys Ile Arg
    210                 215                 220

Glu Phe Tyr His Glu Ile Ile Gly Arg Lys Asn Asp Lys Glu Asn Phe
225                 230                 235                 240

Ala Lys Ile Ile Tyr Glu Glu Ile Gln Asn Val Asn Asn Met Lys Glu
                245                 250                 255

Leu Ile Glu Lys Val Pro Asp Met Ser Glu Leu Lys Lys Ser Gln Val
            260                 265                 270

-continued

```
Phe Tyr Lys Tyr Tyr Leu Asp Lys Glu Glu Leu Asn Asp Lys Asn Ile
        275                 280                 285

Lys Tyr Ala Phe Cys His Phe Val Glu Ile Glu Met Ser Gln Leu Leu
    290                 295                 300

Lys Asn Tyr Val Tyr Lys Arg Leu Ser Asn Ile Ser Asn Asp Lys Ile
305                 310                 315                 320

Lys Arg Ile Phe Glu Tyr Gln Asn Leu Lys Lys Leu Ile Glu Asn Lys
                325                 330                 335

Leu Leu Asn Lys Leu Asp Thr Tyr Val Arg Asn Cys Gly Lys Tyr Asn
            340                 345                 350

Tyr Tyr Leu Gln Asp Gly Glu Ile Ala Thr Ser Asp Phe Ile Ala Arg
        355                 360                 365

Asn Arg Gln Asn Glu Ala Phe Leu Arg Asn Ile Ile Gly Val Ser Ser
    370                 375                 380

Val Ala Tyr Phe Ser Leu Arg Asn Ile Leu Glu Thr Glu Asn Glu Asn
385                 390                 395                 400

Asp Ile Thr Gly Arg Met Arg Gly Lys Thr Val Lys Asn Asn Lys Gly
                405                 410                 415

Glu Glu Lys Tyr Val Ser Gly Glu Val Asp Lys Ile Tyr Asn Glu Asn
            420                 425                 430

Lys Lys Asn Glu Val Lys Glu Asn Leu Lys Met Phe Tyr Ser Tyr Asp
        435                 440                 445

Phe Asn Met Asp Asn Lys Asn Glu Ile Glu Asp Phe Phe Ala Asn Ile
    450                 455                 460

Asp Glu Ala Ile Ser Ser Ile Arg His Gly Ile Val His Phe Asn Leu
465                 470                 475                 480

Glu Leu Glu Gly Lys Asp Ile Phe Ala Phe Lys Asn Ile Ala Pro Ser
                485                 490                 495

Glu Ile Ser Lys Lys Met Phe Gln Asn Glu Ile Asn Glu Lys Lys Leu
            500                 505                 510

Lys Leu Lys Ile Phe Arg Gln Leu Asn Ser Ala Asn Val Phe Arg Tyr
        515                 520                 525

Leu Glu Lys Tyr Lys Ile Leu Asn Tyr Leu Lys Arg Thr Arg Phe Glu
    530                 535                 540

Phe Val Asn Lys Asn Ile Pro Phe Val Pro Ser Phe Thr Lys Leu Tyr
545                 550                 555                 560

Ser Arg Ile Asp Asp Leu Lys Asn Ser Leu Gly Ile Tyr Trp Lys Thr
                565                 570                 575

Pro Lys Thr Asn Asp Asp Asn Lys Thr Lys Glu Ile Ile Asp Ala Gln
            580                 585                 590

Ile Tyr Leu Leu Lys Asn Ile Tyr Tyr Gly Glu Phe Leu Asn Tyr Phe
        595                 600                 605

Met Ser Asn Asn Gly Asn Phe Phe Glu Ile Ser Lys Glu Ile Ile Glu
    610                 615                 620

Leu Asn Lys Asn Asp Lys Arg Asn Leu Lys Thr Gly Phe Tyr Lys Leu
625                 630                 635                 640

Gln Lys Phe Glu Asp Ile Gln Glu Lys Ile Pro Lys Glu Tyr Leu Ala
                645                 650                 655

Asn Ile Gln Ser Leu Tyr Met Ile Asn Ala Gly Asn Gln Asp Glu Glu
            660                 665                 670

Glu Lys Asp Thr Tyr Ile Asp Phe Ile Gln Lys Ile Phe Leu Lys Gly
        675                 680                 685
```

-continued

```
Phe Met Thr Tyr Leu Ala Asn Asn Gly Arg Leu Ser Leu Ile Tyr Ile
    690                 695                 700

Gly Ser Asp Glu Glu Thr Asn Thr Ser Leu Ala Glu Lys Lys Gln Glu
705                 710                 715                 720

Phe Asp Lys Phe Leu Lys Lys Tyr Glu Gln Asn Asn Asn Ile Lys Ile
                725                 730                 735

Pro Tyr Glu Ile Asn Glu Phe Leu Arg Glu Ile Lys Leu Gly Asn Ile
            740                 745                 750

Leu Lys Tyr Thr Glu Arg Leu Asn Met Phe Tyr Leu Ile Leu Lys Leu
        755                 760                 765

Leu Asn His Lys Glu Leu Thr Asn Leu Lys Gly Ser Leu Glu Lys Tyr
    770                 775                 780

Gln Ser Ala Asn Lys Glu Glu Ala Phe Ser Asp Gln Leu Glu Leu Ile
785                 790                 795                 800

Asn Leu Leu Asn Leu Asp Asn Asn Arg Val Thr Glu Asp Phe Glu Leu
                805                 810                 815

Glu Ala Asp Glu Ile Gly Lys Phe Leu Asp Phe Asn Gly Asn Lys Val
            820                 825                 830

Lys Asp Asn Lys Glu Leu Lys Lys Phe Asp Thr Asn Lys Ile Tyr Phe
        835                 840                 845

Asp Gly Glu Asn Ile Ile Lys His Arg Ala Phe Tyr Asn Ile Lys Lys
    850                 855                 860

Tyr Gly Met Leu Asn Leu Leu Glu Lys Ile Ala Asp Lys Ala Gly Tyr
865                 870                 875                 880

Lys Ile Ser Ile Glu Glu Leu Lys Lys Tyr Ser Asn Lys Lys Asn Glu
                885                 890                 895

Ile Glu Lys Asn His Lys Met Gln Glu Asn Leu His Arg Lys Tyr Ala
            900                 905                 910

Arg Pro Arg Lys Asp Glu Lys Phe Thr Asp Glu Asp Tyr Glu Ser Tyr
        915                 920                 925

Lys Gln Ala Ile Glu Asn Ile Glu Glu Tyr Thr His Leu Lys Asn Lys
    930                 935                 940

Val Glu Phe Asn Glu Leu Asn Leu Leu Gln Gly Leu Leu Leu Arg Ile
945                 950                 955                 960

Leu His Arg Leu Val Gly Tyr Thr Ser Ile Trp Glu Arg Asp Leu Arg
                965                 970                 975

Phe Arg Leu Lys Gly Glu Phe Pro Glu Asn Gln Tyr Ile Glu Glu Ile
            980                 985                 990

Phe Asn Phe Glu Asn Lys Lys Asn  Val Lys Tyr Lys Gly  Gly Gln Ile
        995                 1000                1005

Val Glu  Lys Tyr Ile Lys Phe  Tyr Lys Glu Leu His  Gln Asn Asp
    1010                 1015                 1020

Glu Val  Lys Ile Asn Lys Tyr  Ser Ser Ala Asn Ile  Lys Val Leu
    1025                 1030                 1035

Lys Gln  Glu Lys Lys Asp Leu  Tyr Ile Arg Asn Tyr  Ile Ala His
    1040                 1045                 1050

Phe Asn  Tyr Ile Pro His Ala  Glu Ile Ser Leu Leu  Glu Val Leu
    1055                 1060                 1065

Glu Asn  Leu Arg Lys Leu Leu  Ser Tyr Asp Arg Lys  Leu Lys Asn
    1070                 1075                 1080

Ala Val  Met Lys Ser Val Val  Asp Ile Leu Lys Glu  Tyr Gly Phe
    1085                 1090                 1095

Val Ala  Thr Phe Lys Ile Gly  Ala Asp Lys Lys Ile  Gly Ile Gln
```

-continued

```
    1100                1105                1110

Thr Leu  Glu Ser Glu Lys Ile  Val His Leu Lys Asn  Leu Lys Lys
    1115                1120                1125

Lys Lys  Leu Met Thr Asp Arg  Asn Ser Glu Glu Leu  Cys Lys Leu
    1130                1135                1140

Val Lys  Ile Met Phe Glu Tyr  Lys Met Glu Glu Lys  Lys Ser Glu
    1145                1150                1155

Asn


<210> SEQ ID NO 16
<211> LENGTH: 1389
<212> TYPE: PRT
<213> ORGANISM: Leptotrichia shahii

<400> SEQUENCE: 16

Met Gly Asn Leu Phe Gly His Lys Arg Trp Tyr Glu Val Arg Asp Lys
1               5                   10                  15

Lys Asp Phe Lys Ile Lys Arg Lys Val Lys Val Lys Arg Asn Tyr Asp
            20                  25                  30

Gly Asn Lys Tyr Ile Leu Asn Ile Asn Glu Asn Asn Asn Lys Glu Lys
        35                  40                  45

Ile Asp Asn Asn Lys Phe Ile Arg Lys Tyr Ile Asn Tyr Lys Lys Asn
    50                  55                  60

Asp Asn Ile Leu Lys Glu Phe Thr Arg Lys Phe His Ala Gly Asn Ile
65                  70                  75                  80

Leu Phe Lys Leu Lys Gly Lys Glu Gly Ile Ile Arg Ile Glu Asn Asn
                85                  90                  95

Asp Asp Phe Leu Glu Thr Glu Glu Val Val Leu Tyr Ile Glu Ala Tyr
            100                 105                 110

Gly Lys Ser Glu Lys Leu Lys Ala Leu Gly Ile Thr Lys Lys Lys Ile
        115                 120                 125

Ile Asp Glu Ala Ile Arg Gln Gly Ile Thr Lys Asp Asp Lys Lys Ile
    130                 135                 140

Glu Ile Lys Arg Gln Glu Asn Glu Glu Glu Ile Glu Ile Asp Ile Arg
145                 150                 155                 160

Asp Glu Tyr Thr Asn Lys Thr Leu Asn Asp Cys Ser Ile Ile Leu Arg
                165                 170                 175

Ile Ile Glu Asn Asp Glu Leu Glu Thr Lys Lys Ser Ile Tyr Glu Ile
            180                 185                 190

Phe Lys Asn Ile Asn Met Ser Leu Tyr Lys Ile Ile Glu Lys Ile Ile
        195                 200                 205

Glu Asn Glu Thr Glu Lys Val Phe Glu Asn Arg Tyr Tyr Glu Glu His
    210                 215                 220

Leu Arg Glu Lys Leu Leu Lys Asp Asp Lys Ile Asp Val Ile Leu Thr
225                 230                 235                 240

Asn Phe Met Glu Ile Arg Glu Lys Ile Lys Ser Asn Leu Glu Ile Leu
                245                 250                 255

Gly Phe Val Lys Phe Tyr Leu Asn Val Gly Gly Asp Lys Lys Lys Ser
            260                 265                 270

Lys Asn Lys Lys Met Leu Val Glu Lys Ile Leu Asn Ile Asn Val Asp
        275                 280                 285

Leu Thr Val Glu Asp Ile Ala Asp Phe Val Ile Lys Glu Leu Glu Phe
    290                 295                 300

Trp Asn Ile Thr Lys Arg Ile Glu Lys Val Lys Lys Val Asn Asn Glu
```

-continued

```
305                 310                 315                 320

Phe Leu Glu Lys Arg Arg Asn Arg Thr Tyr Ile Lys Ser Tyr Val Leu
                325                 330                 335

Leu Asp Lys His Glu Lys Phe Lys Ile Glu Arg Glu Asn Lys Lys Asp
            340                 345                 350

Lys Ile Val Lys Phe Phe Val Glu Asn Ile Lys Asn Asn Ser Ile Lys
        355                 360                 365

Glu Lys Ile Glu Lys Ile Leu Ala Glu Phe Lys Ile Asp Glu Leu Ile
    370                 375                 380

Lys Lys Leu Glu Lys Glu Leu Lys Lys Gly Asn Cys Asp Thr Glu Ile
385                 390                 395                 400

Phe Gly Ile Phe Lys Lys His Tyr Lys Val Asn Phe Asp Ser Lys Lys
                405                 410                 415

Phe Ser Lys Lys Ser Asp Glu Glu Lys Glu Leu Tyr Lys Ile Ile Tyr
            420                 425                 430

Arg Tyr Leu Lys Gly Arg Ile Glu Lys Ile Leu Val Asn Glu Gln Lys
        435                 440                 445

Val Arg Leu Lys Lys Met Glu Lys Ile Glu Ile Glu Lys Ile Leu Asn
    450                 455                 460

Glu Ser Ile Leu Ser Glu Lys Ile Leu Lys Arg Val Lys Gln Tyr Thr
465                 470                 475                 480

Leu Glu His Ile Met Tyr Leu Gly Lys Leu Arg His Asn Asp Ile Asp
                485                 490                 495

Met Thr Thr Val Asn Thr Asp Asp Phe Ser Arg Leu His Ala Lys Glu
            500                 505                 510

Glu Leu Asp Leu Glu Leu Ile Thr Phe Phe Ala Ser Thr Asn Met Glu
        515                 520                 525

Leu Asn Lys Ile Phe Ser Arg Glu Asn Ile Asn Asn Asp Glu Asn Ile
    530                 535                 540

Asp Phe Phe Gly Gly Asp Arg Glu Lys Asn Tyr Val Leu Asp Lys Lys
545                 550                 555                 560

Ile Leu Asn Ser Lys Ile Lys Ile Ile Arg Asp Leu Asp Phe Ile Asp
                565                 570                 575

Asn Lys Asn Asn Ile Thr Asn Asn Phe Ile Arg Lys Phe Thr Lys Ile
            580                 585                 590

Gly Thr Asn Glu Arg Asn Arg Ile Leu His Ala Ile Ser Lys Glu Arg
        595                 600                 605

Asp Leu Gln Gly Thr Gln Asp Asp Tyr Asn Lys Val Ile Asn Ile Ile
    610                 615                 620

Gln Asn Leu Lys Ile Ser Asp Glu Glu Val Ser Lys Ala Leu Asn Leu
625                 630                 635                 640

Asp Val Val Phe Lys Asp Lys Lys Asn Ile Ile Thr Lys Ile Asn Asp
                645                 650                 655

Ile Lys Ile Ser Glu Glu Asn Asn Asn Asp Ile Lys Tyr Leu Pro Ser
            660                 665                 670

Phe Ser Lys Val Leu Pro Glu Ile Leu Asn Leu Tyr Arg Asn Asn Pro
        675                 680                 685

Lys Asn Glu Pro Phe Asp Thr Ile Glu Thr Glu Lys Ile Val Leu Asn
    690                 695                 700

Ala Leu Ile Tyr Val Asn Lys Glu Leu Tyr Lys Lys Leu Ile Leu Glu
705                 710                 715                 720

Asp Asp Leu Glu Glu Asn Glu Ser Lys Asn Ile Phe Leu Gln Glu Leu
                725                 730                 735
```

-continued

```
Lys Lys Thr Leu Gly Asn Ile Asp Glu Ile Asp Glu Asn Ile Ile Glu
            740                 745                 750

Asn Tyr Tyr Lys Asn Ala Gln Ile Ser Ala Ser Lys Gly Asn Asn Lys
        755                 760                 765

Ala Ile Lys Lys Tyr Gln Lys Lys Val Ile Glu Cys Tyr Ile Gly Tyr
    770                 775                 780

Leu Arg Lys Asn Tyr Glu Glu Leu Phe Asp Phe Ser Asp Phe Lys Met
785                 790                 795                 800

Asn Ile Gln Glu Ile Lys Lys Gln Ile Lys Asp Ile Asn Asp Asn Lys
                805                 810                 815

Thr Tyr Glu Arg Ile Thr Val Lys Thr Ser Asp Lys Thr Ile Val Ile
            820                 825                 830

Asn Asp Asp Phe Glu Tyr Ile Ile Ser Ile Phe Ala Leu Leu Asn Ser
        835                 840                 845

Asn Ala Val Ile Asn Lys Ile Arg Asn Arg Phe Phe Ala Thr Ser Val
    850                 855                 860

Trp Leu Asn Thr Ser Glu Tyr Gln Asn Ile Ile Asp Ile Leu Asp Glu
865                 870                 875                 880

Ile Met Gln Leu Asn Thr Leu Arg Asn Glu Cys Ile Thr Glu Asn Trp
                885                 890                 895

Asn Leu Asn Leu Glu Glu Phe Ile Gln Lys Met Lys Glu Ile Glu Lys
            900                 905                 910

Asp Phe Asp Asp Phe Lys Ile Gln Thr Lys Lys Glu Ile Phe Asn Asn
        915                 920                 925

Tyr Tyr Glu Asp Ile Lys Asn Asn Ile Leu Thr Glu Phe Lys Asp Asp
    930                 935                 940

Ile Asn Gly Cys Asp Val Leu Glu Lys Lys Leu Glu Lys Ile Val Ile
945                 950                 955                 960

Phe Asp Asp Glu Thr Lys Phe Glu Ile Asp Lys Lys Ser Asn Ile Leu
                965                 970                 975

Gln Asp Glu Gln Arg Lys Leu Ser Asn Ile Asn Lys Lys Asp Leu Lys
            980                 985                 990

Lys Lys Val Asp Gln Tyr Ile Lys  Asp Lys Asp Gln Glu  Ile Lys Ser
        995                 1000                1005

Lys Ile  Leu Cys Arg Ile Ile  Phe Asn Ser Asp Phe  Leu Lys Lys
    1010                 1015                 1020

Tyr Lys  Lys Glu Ile Asp Asn  Leu Ile Glu Asp Met  Glu Ser Glu
    1025                 1030                 1035

Asn Glu  Asn Lys Phe Gln Glu  Ile Tyr Tyr Pro Lys  Glu Arg Lys
    1040                 1045                 1050

Asn Glu  Leu Tyr Ile Tyr Lys  Lys Asn Leu Phe Leu  Asn Ile Gly
    1055                 1060                 1065

Asn Pro  Asn Phe Asp Lys Ile  Tyr Gly Leu Ile Ser  Asn Asp Ile
    1070                 1075                 1080

Lys Met  Ala Asp Ala Lys Phe  Leu Phe Asn Ile Asp  Gly Lys Asn
    1085                 1090                 1095

Ile Arg  Lys Asn Lys Ile Ser  Glu Ile Asp Ala Ile  Leu Lys Asn
    1100                 1105                 1110

Leu Asn  Asp Lys Leu Asn Gly  Tyr Ser Lys Glu Tyr  Lys Glu Lys
    1115                 1120                 1125

Tyr Ile  Lys Lys Leu Lys Glu  Asn Asp Asp Phe Phe  Ala Lys Asn
    1130                 1135                 1140
```

Ile Gln Asn Lys Asn Tyr Lys Ser Phe Glu Lys Asp Tyr Asn Arg
1145 1150 1155

Val Ser Glu Tyr Lys Lys Ile Arg Asp Leu Val Glu Phe Asn Tyr
1160 1165 1170

Leu Asn Lys Ile Glu Ser Tyr Leu Ile Asp Ile Asn Trp Lys Leu
1175 1180 1185

Ala Ile Gln Met Ala Arg Phe Glu Arg Asp Met His Tyr Ile Val
1190 1195 1200

Asn Gly Leu Arg Glu Leu Gly Ile Ile Lys Leu Ser Gly Tyr Asn
1205 1210 1215

Thr Gly Ile Ser Arg Ala Tyr Pro Lys Arg Asn Gly Ser Asp Gly
1220 1225 1230

Phe Tyr Thr Thr Thr Ala Tyr Tyr Lys Phe Phe Asp Glu Glu Ser
1235 1240 1245

Tyr Lys Lys Phe Glu Lys Ile Cys Tyr Gly Phe Gly Ile Asp Leu
1250 1255 1260

Ser Glu Asn Ser Glu Ile Asn Lys Pro Glu Asn Glu Ser Ile Arg
1265 1270 1275

Asn Tyr Ile Ser His Phe Tyr Ile Val Arg Asn Pro Phe Ala Asp
1280 1285 1290

Tyr Ser Ile Ala Glu Gln Ile Asp Arg Val Ser Asn Leu Leu Ser
1295 1300 1305

Tyr Ser Thr Arg Tyr Asn Asn Ser Thr Tyr Ala Ser Val Phe Glu
1310 1315 1320

Val Phe Lys Lys Asp Val Asn Leu Asp Tyr Asp Glu Leu Lys Lys
1325 1330 1335

Lys Phe Lys Leu Ile Gly Asn Asn Asp Ile Leu Glu Arg Leu Met
1340 1345 1350

Lys Pro Lys Lys Val Ser Val Leu Glu Leu Glu Ser Tyr Asn Ser
1355 1360 1365

Asp Tyr Ile Lys Asn Leu Ile Ile Glu Leu Leu Thr Lys Ile Glu
1370 1375 1380

Asn Thr Asn Asp Thr Leu
1385

<210> SEQ ID NO 17
<211> LENGTH: 1285
<212> TYPE: PRT
<213> ORGANISM: Rhodobacter capsulatus

<400> SEQUENCE: 17

Met Gln Ile Gly Lys Val Gln Gly Arg Thr Ile Ser Glu Phe Gly Asp
1 5 10 15

Pro Ala Gly Gly Leu Lys Arg Lys Ile Ser Thr Asp Gly Lys Asn Arg
20 25 30

Lys Glu Leu Pro Ala His Leu Ser Ser Asp Pro Lys Ala Leu Ile Gly
35 40 45

Gln Trp Ile Ser Gly Ile Asp Lys Ile Tyr Arg Lys Pro Asp Ser Arg
50 55 60

Lys Ser Asp Gly Lys Ala Ile His Ser Pro Thr Pro Ser Lys Met Gln
65 70 75 80

Phe Asp Ala Arg Asp Asp Leu Gly Glu Ala Phe Trp Lys Leu Val Ser
85 90 95

Glu Ala Gly Leu Ala Gln Asp Ser Asp Tyr Asp Gln Phe Lys Arg Arg
100 105 110

-continued

```
Leu His Pro Tyr Gly Asp Lys Phe Gln Pro Ala Asp Ser Gly Ala Lys
        115                 120                 125

Leu Lys Phe Glu Ala Asp Pro Pro Glu Pro Gln Ala Phe His Gly Arg
    130                 135                 140

Trp Tyr Gly Ala Met Ser Lys Arg Gly Asn Asp Ala Lys Glu Leu Ala
145                 150                 155                 160

Ala Ala Leu Tyr Glu His Leu His Val Asp Glu Lys Arg Ile Asp Gly
                165                 170                 175

Gln Pro Lys Arg Asn Pro Lys Thr Asp Lys Phe Ala Pro Gly Leu Val
            180                 185                 190

Val Ala Arg Ala Leu Gly Ile Glu Ser Ser Val Leu Pro Arg Gly Met
        195                 200                 205

Ala Arg Leu Ala Arg Asn Trp Gly Glu Glu Glu Ile Gln Thr Tyr Phe
    210                 215                 220

Val Val Asp Val Ala Ala Ser Val Lys Glu Val Ala Lys Ala Ala Val
225                 230                 235                 240

Ser Ala Ala Gln Ala Phe Asp Pro Pro Arg Gln Val Ser Gly Arg Ser
                245                 250                 255

Leu Ser Pro Lys Val Gly Phe Ala Leu Ala Glu His Leu Glu Arg Val
            260                 265                 270

Thr Gly Ser Lys Arg Cys Ser Phe Asp Pro Ala Ala Gly Pro Ser Val
        275                 280                 285

Leu Ala Leu His Asp Glu Val Lys Lys Thr Tyr Lys Arg Leu Cys Ala
    290                 295                 300

Arg Gly Lys Asn Ala Ala Arg Ala Phe Pro Ala Asp Lys Thr Glu Leu
305                 310                 315                 320

Leu Ala Leu Met Arg His Thr His Glu Asn Arg Val Arg Asn Gln Met
                325                 330                 335

Val Arg Met Gly Arg Val Ser Glu Tyr Arg Gly Gln Gln Ala Gly Asp
            340                 345                 350

Leu Ala Gln Ser His Tyr Trp Thr Ser Ala Gly Gln Thr Glu Ile Lys
        355                 360                 365

Glu Ser Glu Ile Phe Val Arg Leu Trp Val Gly Ala Phe Ala Leu Ala
    370                 375                 380

Gly Arg Ser Met Lys Ala Trp Ile Asp Pro Met Gly Lys Ile Val Asn
385                 390                 395                 400

Thr Glu Lys Asn Asp Arg Asp Leu Thr Ala Ala Val Asn Ile Arg Gln
                405                 410                 415

Val Ile Ser Asn Lys Glu Met Val Ala Glu Ala Met Ala Arg Arg Gly
            420                 425                 430

Ile Tyr Phe Gly Glu Thr Pro Glu Leu Asp Arg Leu Gly Ala Glu Gly
        435                 440                 445

Asn Glu Gly Phe Val Phe Ala Leu Leu Arg Tyr Leu Arg Gly Cys Arg
    450                 455                 460

Asn Gln Thr Phe His Leu Gly Ala Arg Ala Gly Phe Leu Lys Glu Ile
465                 470                 475                 480

Arg Lys Glu Leu Glu Lys Thr Arg Trp Gly Lys Ala Lys Glu Ala Glu
                485                 490                 495

His Val Val Leu Thr Asp Lys Thr Val Ala Ala Ile Arg Ala Ile Ile
            500                 505                 510

Asp Asn Asp Ala Lys Ala Leu Gly Ala Arg Leu Leu Ala Asp Leu Ser
        515                 520                 525
```

-continued

```
Gly Ala Phe Val Ala His Tyr Ala Ser Lys Glu His Phe Ser Thr Leu
    530                 535                 540

Tyr Ser Glu Ile Val Lys Ala Val Lys Asp Ala Pro Glu Val Ser Ser
545                 550                 555                 560

Gly Leu Pro Arg Leu Lys Leu Leu Leu Lys Arg Ala Asp Gly Val Arg
                565                 570                 575

Gly Tyr Val His Gly Leu Arg Asp Thr Arg Lys His Ala Phe Ala Thr
            580                 585                 590

Lys Leu Pro Pro Pro Pro Ala Pro Arg Glu Leu Asp Asp Pro Ala Thr
        595                 600                 605

Lys Ala Arg Tyr Ile Ala Leu Leu Arg Leu Tyr Asp Gly Pro Phe Arg
    610                 615                 620

Ala Tyr Ala Ser Gly Ile Thr Gly Thr Ala Leu Ala Gly Pro Ala Ala
625                 630                 635                 640

Arg Ala Lys Glu Ala Ala Thr Ala Leu Ala Gln Ser Val Asn Val Thr
                645                 650                 655

Lys Ala Tyr Ser Asp Val Met Glu Gly Arg Ser Ser Arg Leu Arg Pro
            660                 665                 670

Pro Asn Asp Gly Glu Thr Leu Arg Glu Tyr Leu Ser Ala Leu Thr Gly
        675                 680                 685

Glu Thr Ala Thr Glu Phe Arg Val Gln Ile Gly Tyr Glu Ser Asp Ser
    690                 695                 700

Glu Asn Ala Arg Lys Gln Ala Glu Phe Ile Glu Asn Tyr Arg Arg Asp
705                 710                 715                 720

Met Leu Ala Phe Met Phe Glu Asp Tyr Ile Arg Ala Lys Gly Phe Asp
                725                 730                 735

Trp Ile Leu Lys Ile Glu Pro Gly Ala Thr Ala Met Thr Arg Ala Pro
            740                 745                 750

Val Leu Pro Glu Pro Ile Asp Thr Arg Gly Gln Tyr Glu His Trp Gln
        755                 760                 765

Ala Ala Leu Tyr Leu Val Met His Phe Val Pro Ala Ser Asp Val Ser
    770                 775                 780

Asn Leu Leu His Gln Leu Arg Lys Trp Glu Ala Leu Gln Gly Lys Tyr
785                 790                 795                 800

Glu Leu Val Gln Asp Gly Asp Ala Thr Asp Gln Ala Asp Ala Arg Arg
                805                 810                 815

Glu Ala Leu Asp Leu Val Lys Arg Phe Arg Asp Val Leu Val Leu Phe
            820                 825                 830

Leu Lys Thr Gly Glu Ala Arg Phe Glu Gly Arg Ala Ala Pro Phe Asp
        835                 840                 845

Leu Lys Pro Phe Arg Ala Leu Phe Ala Asn Pro Ala Thr Phe Asp Arg
    850                 855                 860

Leu Phe Met Ala Thr Pro Thr Thr Ala Arg Pro Ala Glu Asp Asp Pro
865                 870                 875                 880

Glu Gly Asp Gly Ala Ser Glu Pro Glu Leu Arg Val Ala Arg Thr Leu
                885                 890                 895

Arg Gly Leu Arg Gln Ile Ala Arg Tyr Asn His Met Ala Val Leu Ser
            900                 905                 910

Asp Leu Phe Ala Lys His Lys Val Arg Asp Glu Glu Val Ala Arg Leu
        915                 920                 925

Ala Glu Ile Glu Asp Glu Thr Gln Glu Lys Ser Gln Ile Val Ala Ala
    930                 935                 940

Gln Glu Leu Arg Thr Asp Leu His Asp Lys Val Met Lys Cys His Pro
```

-continued 945 950 955 960

Lys Thr Ile Ser Pro Glu Glu Arg Gln Ser Tyr Ala Ala Ala Ile Lys
965 970 975

Thr Ile Glu Glu His Arg Phe Leu Val Gly Arg Val Tyr Leu Gly Asp
980 985 990

His Leu Arg Leu His Arg Leu Met Met Asp Val Ile Gly Arg Leu Ile
995 1000 1005

Asp Tyr Ala Gly Ala Tyr Glu Arg Asp Thr Gly Thr Phe Leu Ile
1010 1015 1020

Asn Ala Ser Lys Gln Leu Gly Ala Gly Ala Asp Trp Ala Val Thr
1025 1030 1035

Ile Ala Gly Ala Ala Asn Thr Asp Ala Arg Thr Gln Thr Arg Lys
1040 1045 1050

Asp Leu Ala His Phe Asn Val Leu Asp Arg Ala Asp Gly Thr Pro
1055 1060 1065

Asp Leu Thr Ala Leu Val Asn Arg Ala Arg Glu Met Met Ala Tyr
1070 1075 1080

Asp Arg Lys Arg Lys Asn Ala Val Pro Arg Ser Ile Leu Asp Met
1085 1090 1095

Leu Ala Arg Leu Gly Leu Thr Leu Lys Trp Gln Met Lys Asp His
1100 1105 1110

Leu Leu Gln Asp Ala Thr Ile Thr Gln Ala Ala Ile Lys His Leu
1115 1120 1125

Asp Lys Val Arg Leu Thr Val Gly Gly Pro Ala Ala Val Thr Glu
1130 1135 1140

Ala Arg Phe Ser Gln Asp Tyr Leu Gln Met Val Ala Ala Val Phe
1145 1150 1155

Asn Gly Ser Val Gln Asn Pro Lys Pro Arg Arg Arg Asp Asp Gly
1160 1165 1170

Asp Ala Trp His Lys Pro Pro Lys Pro Ala Thr Ala Gln Ser Gln
1175 1180 1185

Pro Asp Gln Lys Pro Pro Asn Lys Ala Pro Ser Ala Gly Ser Arg
1190 1195 1200

Leu Pro Pro Pro Gln Val Gly Glu Val Tyr Glu Gly Val Val Val
1205 1210 1215

Lys Val Ile Asp Thr Gly Ser Leu Gly Phe Leu Ala Val Glu Gly
1220 1225 1230

Val Ala Gly Asn Ile Gly Leu His Ile Ser Arg Leu Arg Arg Ile
1235 1240 1245

Arg Glu Asp Ala Ile Ile Val Gly Arg Arg Tyr Arg Phe Arg Val
1250 1255 1260

Glu Ile Tyr Val Pro Pro Lys Ser Asn Thr Ser Lys Leu Asn Ala
1265 1270 1275

Ala Asp Leu Val Arg Ile Asp
1280 1285

<210> SEQ ID NO 18
<211> LENGTH: 1175
<212> TYPE: PRT
<213> ORGANISM: Carnobacterium gallinarum

<400> SEQUENCE: 18

Met Arg Ile Thr Lys Val Lys Ile Lys Leu Asp Asn Lys Leu Tyr Gln
1 5 10 15

-continued

```
Val Thr Met Gln Lys Glu Glu Lys Tyr Gly Thr Leu Lys Leu Asn Glu
            20                  25                  30

Glu Ser Arg Lys Ser Thr Ala Glu Ile Leu Arg Leu Lys Lys Ala Ser
        35                  40                  45

Phe Asn Lys Ser Phe His Ser Lys Thr Ile Asn Ser Gln Lys Glu Asn
    50                  55                  60

Lys Asn Ala Thr Ile Lys Lys Asn Gly Asp Tyr Ile Ser Gln Ile Phe
65                  70                  75                  80

Glu Lys Leu Val Gly Val Asp Thr Asn Lys Asn Ile Arg Lys Pro Lys
                85                  90                  95

Met Ser Leu Thr Asp Leu Lys Asp Leu Pro Lys Lys Asp Leu Ala Leu
            100                 105                 110

Phe Ile Lys Arg Lys Phe Lys Asn Asp Asp Ile Val Glu Ile Lys Asn
        115                 120                 125

Leu Asp Leu Ile Ser Leu Phe Tyr Asn Ala Leu Gln Lys Val Pro Gly
    130                 135                 140

Glu His Phe Thr Asp Glu Ser Trp Ala Asp Phe Cys Gln Glu Met Met
145                 150                 155                 160

Pro Tyr Arg Glu Tyr Lys Asn Lys Phe Ile Glu Arg Lys Ile Ile Leu
                165                 170                 175

Leu Ala Asn Ser Ile Glu Gln Asn Lys Gly Phe Ser Ile Asn Pro Glu
            180                 185                 190

Thr Phe Ser Lys Arg Lys Arg Val Leu His Gln Trp Ala Ile Glu Val
        195                 200                 205

Gln Glu Arg Gly Asp Phe Ser Ile Leu Asp Glu Lys Leu Ser Lys Leu
    210                 215                 220

Ala Glu Ile Tyr Asn Phe Lys Lys Met Cys Lys Arg Val Gln Asp Glu
225                 230                 235                 240

Leu Asn Asp Leu Glu Lys Ser Met Lys Lys Gly Lys Asn Pro Glu Lys
                245                 250                 255

Glu Lys Glu Ala Tyr Lys Lys Gln Lys Asn Phe Lys Ile Lys Thr Ile
            260                 265                 270

Trp Lys Asp Tyr Pro Tyr Lys Thr His Ile Gly Leu Ile Glu Lys Ile
        275                 280                 285

Lys Glu Asn Glu Glu Leu Asn Gln Phe Asn Ile Glu Ile Gly Lys Tyr
    290                 295                 300

Phe Glu His Tyr Phe Pro Ile Lys Lys Glu Arg Cys Thr Glu Asp Glu
305                 310                 315                 320

Pro Tyr Tyr Leu Asn Ser Glu Thr Ile Ala Thr Thr Val Asn Tyr Gln
                325                 330                 335

Leu Lys Asn Ala Leu Ile Ser Tyr Leu Met Gln Ile Gly Lys Tyr Lys
            340                 345                 350

Gln Phe Gly Leu Glu Asn Gln Val Leu Asp Ser Lys Lys Leu Gln Glu
        355                 360                 365

Ile Gly Ile Tyr Glu Gly Phe Gln Thr Lys Phe Met Asp Ala Cys Val
    370                 375                 380

Phe Ala Thr Ser Ser Leu Lys Asn Ile Ile Glu Pro Met Arg Ser Gly
385                 390                 395                 400

Asp Ile Leu Gly Lys Arg Glu Phe Lys Glu Ala Ile Ala Thr Ser Ser
                405                 410                 415

Phe Val Asn Tyr His His Phe Phe Pro Tyr Phe Pro Phe Glu Leu Lys
            420                 425                 430

Gly Met Lys Asp Arg Glu Ser Glu Leu Ile Pro Phe Gly Glu Gln Thr
```

-continued

```
        435                 440                 445

Glu Ala Lys Gln Met Gln Asn Ile Trp Ala Leu Arg Gly Ser Val Gln
    450                 455                 460

Gln Ile Arg Asn Glu Ile Phe His Ser Phe Asp Lys Asn Gln Lys Phe
465                 470                 475                 480

Asn Leu Pro Gln Leu Asp Lys Ser Asn Phe Glu Phe Asp Ala Ser Glu
                485                 490                 495

Asn Ser Thr Gly Lys Ser Gln Ser Tyr Ile Glu Thr Asp Tyr Lys Phe
            500                 505                 510

Leu Phe Glu Ala Glu Lys Asn Gln Leu Glu Gln Phe Phe Ile Glu Arg
        515                 520                 525

Ile Lys Ser Ser Gly Ala Leu Glu Tyr Tyr Pro Leu Lys Ser Leu Glu
    530                 535                 540

Lys Leu Phe Ala Lys Lys Glu Met Lys Phe Ser Leu Gly Ser Gln Val
545                 550                 555                 560

Val Ala Phe Ala Pro Ser Tyr Lys Lys Leu Val Lys Lys Gly His Ser
                565                 570                 575

Tyr Gln Thr Ala Thr Glu Gly Thr Ala Asn Tyr Leu Gly Leu Ser Tyr
            580                 585                 590

Tyr Asn Arg Tyr Glu Leu Lys Glu Glu Ser Phe Gln Ala Gln Tyr Tyr
        595                 600                 605

Leu Leu Lys Leu Ile Tyr Gln Tyr Val Phe Leu Pro Asn Phe Ser Gln
    610                 615                 620

Gly Asn Ser Pro Ala Phe Arg Glu Thr Val Lys Ala Ile Leu Arg Ile
625                 630                 635                 640

Asn Lys Asp Glu Ala Arg Lys Lys Met Lys Lys Asn Lys Lys Phe Leu
                645                 650                 655

Arg Lys Tyr Ala Phe Glu Gln Val Arg Glu Met Glu Phe Lys Glu Thr
            660                 665                 670

Pro Asp Gln Tyr Met Ser Tyr Leu Gln Ser Glu Met Arg Glu Glu Lys
        675                 680                 685

Val Arg Lys Ala Glu Lys Asn Asp Lys Gly Phe Glu Lys Asn Ile Thr
    690                 695                 700

Met Asn Phe Glu Lys Leu Leu Met Gln Ile Phe Val Lys Gly Phe Asp
705                 710                 715                 720

Val Phe Leu Thr Thr Phe Ala Gly Lys Glu Leu Leu Leu Ser Ser Glu
                725                 730                 735

Glu Lys Val Ile Lys Glu Thr Glu Ile Ser Leu Ser Lys Lys Ile Asn
            740                 745                 750

Glu Arg Glu Lys Thr Leu Lys Ala Ser Ile Gln Val Glu His Gln Leu
        755                 760                 765

Val Ala Thr Asn Ser Ala Ile Ser Tyr Trp Leu Phe Cys Lys Leu Leu
    770                 775                 780

Asp Ser Arg His Leu Asn Glu Leu Arg Asn Glu Met Ile Lys Phe Lys
785                 790                 795                 800

Gln Ser Arg Ile Lys Phe Asn His Thr Gln His Ala Glu Leu Ile Gln
                805                 810                 815

Asn Leu Leu Pro Ile Val Glu Leu Thr Ile Leu Ser Asn Asp Tyr Asp
            820                 825                 830

Glu Lys Asn Asp Ser Gln Asn Val Asp Val Ser Ala Tyr Phe Glu Asp
        835                 840                 845

Lys Ser Leu Tyr Glu Thr Ala Pro Tyr Val Gln Thr Asp Asp Arg Thr
    850                 855                 860
```

```
Arg Val Ser Phe Arg Pro Ile Leu Lys Leu Glu Lys Tyr His Thr Lys
865                 870                 875                 880

Ser Leu Ile Glu Ala Leu Leu Lys Asp Asn Pro Gln Phe Arg Val Ala
                885                 890                 895

Ala Thr Asp Ile Gln Glu Trp Met His Lys Arg Glu Glu Ile Gly Glu
            900                 905                 910

Leu Val Glu Lys Arg Lys Asn Leu His Thr Glu Trp Ala Glu Gly Gln
        915                 920                 925

Gln Thr Leu Gly Ala Glu Lys Arg Glu Glu Tyr Arg Asp Tyr Cys Lys
    930                 935                 940

Lys Ile Asp Arg Phe Asn Trp Lys Ala Asn Lys Val Thr Leu Thr Tyr
945                 950                 955                 960

Leu Ser Gln Leu His Tyr Leu Ile Thr Asp Leu Leu Gly Arg Met Val
                965                 970                 975

Gly Phe Ser Ala Leu Phe Glu Arg Asp Leu Val Tyr Phe Ser Arg Ser
            980                 985                 990

Phe Ser Glu Leu Gly Gly Glu Thr  Tyr His Ile Ser Asp  Tyr Lys Asn
        995                 1000                1005

Leu Ser  Gly Val Leu Arg Leu  Asn Ala Glu Val Lys  Pro Ile Lys
    1010                 1015                 1020

Ile Lys  Asn Ile Lys Val Ile  Asp Asn Glu Glu Asn  Pro Tyr Lys
    1025                 1030                 1035

Gly Asn  Glu Pro Glu Val Lys  Pro Phe Leu Asp Arg  Leu His Ala
    1040                 1045                 1050

Tyr Leu  Glu Asn Val Ile Gly  Ile Lys Ala Val His  Gly Lys Ile
    1055                 1060                 1065

Arg Asn  Gln Thr Ala His Leu  Ser Val Leu Gln Leu  Glu Leu Ser
    1070                 1075                 1080

Met Ile  Glu Ser Met Asn Asn  Leu Arg Asp Leu Met  Ala Tyr Asp
    1085                 1090                 1095

Arg Lys  Leu Lys Asn Ala Val  Thr Lys Ser Met Ile  Lys Ile Leu
    1100                 1105                 1110

Asp Lys  His Gly Met Ile Leu  Lys Leu Lys Ile Asp  Glu Asn His
    1115                 1120                 1125

Lys Asn  Phe Glu Ile Glu Ser  Leu Ile Pro Lys Glu  Ile Ile His
    1130                 1135                 1140

Leu Lys  Asp Lys Ala Ile Lys  Thr Asn Gln Val Ser  Glu Glu Tyr
    1145                 1150                 1155

Cys Gln  Leu Val Leu Ala Leu  Leu Thr Thr Asn Pro  Gly Asn Gln
    1160                 1165                 1170

Leu Asn
    1175
```

<210> SEQ ID NO 19
<211> LENGTH: 1285
<212> TYPE: PRT
<213> ORGANISM: Herbinix hemicellulosilytica

<400> SEQUENCE: 19

```
Met Lys Leu Thr Arg Arg Arg Ile Ser Gly Asn Ser Val Asp Gln Lys
1               5                   10                  15

Ile Thr Ala Ala Phe Tyr Arg Asp Met Ser Gln Gly Leu Leu Tyr Tyr
            20                  25                  30

Asp Ser Glu Asp Asn Asp Cys Thr Asp Lys Val Ile Glu Ser Met Asp
```

-continued

```
        35                  40                  45

Phe Glu Arg Ser Trp Arg Gly Arg Ile Leu Lys Asn Gly Glu Asp Asp
    50                  55                  60

Lys Asn Pro Phe Tyr Met Phe Val Lys Gly Leu Val Gly Ser Asn Asp
65                  70                  75                  80

Lys Ile Val Cys Glu Pro Ile Asp Val Asp Ser Asp Pro Asp Asn Leu
                85                  90                  95

Asp Ile Leu Ile Asn Lys Asn Leu Thr Gly Phe Gly Arg Asn Leu Lys
            100                 105                 110

Ala Pro Asp Ser Asn Asp Thr Leu Glu Asn Leu Ile Arg Lys Ile Gln
        115                 120                 125

Ala Gly Ile Pro Glu Glu Glu Val Leu Pro Glu Leu Lys Lys Ile Lys
    130                 135                 140

Glu Met Ile Gln Lys Asp Ile Val Asn Arg Lys Glu Gln Leu Leu Lys
145                 150                 155                 160

Ser Ile Lys Asn Asn Arg Ile Pro Phe Ser Leu Glu Gly Ser Lys Leu
                165                 170                 175

Val Pro Ser Thr Lys Lys Met Lys Trp Leu Phe Lys Leu Ile Asp Val
            180                 185                 190

Pro Asn Lys Thr Phe Asn Glu Lys Met Leu Glu Lys Tyr Trp Glu Ile
        195                 200                 205

Tyr Asp Tyr Asp Lys Leu Lys Ala Asn Ile Thr Asn Arg Leu Asp Lys
    210                 215                 220

Thr Asp Lys Lys Ala Arg Ser Ile Ser Arg Ala Val Ser Glu Glu Leu
225                 230                 235                 240

Arg Glu Tyr His Lys Asn Leu Arg Thr Asn Tyr Asn Arg Phe Val Ser
                245                 250                 255

Gly Asp Arg Pro Ala Ala Gly Leu Asp Asn Gly Gly Ser Ala Lys Tyr
            260                 265                 270

Asn Pro Asp Lys Glu Glu Phe Leu Leu Phe Leu Lys Glu Val Glu Gln
        275                 280                 285

Tyr Phe Lys Lys Tyr Phe Pro Val Lys Ser Lys His Ser Asn Lys Ser
    290                 295                 300

Lys Asp Lys Ser Leu Val Asp Lys Tyr Lys Asn Tyr Cys Ser Tyr Lys
305                 310                 315                 320

Val Val Lys Lys Glu Val Asn Arg Ser Ile Ile Asn Gln Leu Val Ala
                325                 330                 335

Gly Leu Ile Gln Gln Gly Lys Leu Leu Tyr Tyr Phe Tyr Tyr Asn Asp
            340                 345                 350

Thr Trp Gln Glu Asp Phe Leu Asn Ser Tyr Gly Leu Ser Tyr Ile Gln
        355                 360                 365

Val Glu Glu Ala Phe Lys Lys Ser Val Met Thr Ser Leu Ser Trp Gly
    370                 375                 380

Ile Asn Arg Leu Thr Ser Phe Phe Ile Asp Asp Ser Asn Thr Val Lys
385                 390                 395                 400

Phe Asp Asp Ile Thr Thr Lys Lys Ala Lys Glu Ala Ile Glu Ser Asn
                405                 410                 415

Tyr Phe Asn Lys Leu Arg Thr Cys Ser Arg Met Gln Asp His Phe Lys
            420                 425                 430

Glu Lys Leu Ala Phe Phe Tyr Pro Val Tyr Val Lys Asp Lys Lys Asp
        435                 440                 445

Arg Pro Asp Asp Asp Ile Glu Asn Leu Ile Val Leu Val Lys Asn Ala
    450                 455                 460
```

-continued

```
Ile Glu Ser Val Ser Tyr Leu Arg Asn Arg Thr Phe His Phe Lys Glu
465                 470                 475                 480

Ser Ser Leu Leu Glu Leu Leu Lys Glu Leu Asp Asp Lys Asn Ser Gly
                485                 490                 495

Gln Asn Lys Ile Asp Tyr Ser Val Ala Ala Glu Phe Ile Lys Arg Asp
            500                 505                 510

Ile Glu Asn Leu Tyr Asp Val Phe Arg Glu Gln Ile Arg Ser Leu Gly
        515                 520                 525

Ile Ala Glu Tyr Tyr Lys Ala Asp Met Ile Ser Asp Cys Phe Lys Thr
    530                 535                 540

Cys Gly Leu Glu Phe Ala Leu Tyr Ser Pro Lys Asn Ser Leu Met Pro
545                 550                 555                 560

Ala Phe Lys Asn Val Tyr Lys Arg Gly Ala Asn Leu Asn Lys Ala Tyr
                565                 570                 575

Ile Arg Asp Lys Gly Pro Lys Glu Thr Gly Asp Gln Gly Gln Asn Ser
            580                 585                 590

Tyr Lys Ala Leu Glu Glu Tyr Arg Glu Leu Thr Trp Tyr Ile Glu Val
        595                 600                 605

Lys Asn Asn Asp Gln Ser Tyr Asn Ala Tyr Lys Asn Leu Leu Gln Leu
    610                 615                 620

Ile Tyr Tyr His Ala Phe Leu Pro Glu Val Arg Glu Asn Glu Ala Leu
625                 630                 635                 640

Ile Thr Asp Phe Ile Asn Arg Thr Lys Glu Trp Asn Arg Lys Glu Thr
                645                 650                 655

Glu Glu Arg Leu Asn Thr Lys Asn Asn Lys Lys His Lys Asn Phe Asp
            660                 665                 670

Glu Asn Asp Asp Ile Thr Val Asn Thr Tyr Arg Tyr Glu Ser Ile Pro
        675                 680                 685

Asp Tyr Gln Gly Glu Ser Leu Asp Asp Tyr Leu Lys Val Leu Gln Arg
    690                 695                 700

Lys Gln Met Ala Arg Ala Lys Glu Val Asn Glu Lys Glu Glu Gly Asn
705                 710                 715                 720

Asn Asn Tyr Ile Gln Phe Ile Arg Asp Val Val Val Trp Ala Phe Gly
                725                 730                 735

Ala Tyr Leu Glu Asn Lys Leu Lys Asn Tyr Lys Asn Glu Leu Gln Pro
            740                 745                 750

Pro Leu Ser Lys Glu Asn Ile Gly Leu Asn Asp Thr Leu Lys Glu Leu
        755                 760                 765

Phe Pro Glu Glu Lys Val Lys Ser Pro Phe Asn Ile Lys Cys Arg Phe
    770                 775                 780

Ser Ile Ser Thr Phe Ile Asp Asn Lys Gly Lys Ser Thr Asp Asn Thr
785                 790                 795                 800

Ser Ala Glu Ala Val Lys Thr Asp Gly Lys Glu Asp Glu Lys Asp Lys
                805                 810                 815

Lys Asn Ile Lys Arg Lys Asp Leu Leu Cys Phe Tyr Leu Phe Leu Arg
            820                 825                 830

Leu Leu Asp Glu Asn Glu Ile Cys Lys Leu Gln His Gln Phe Ile Lys
        835                 840                 845

Tyr Arg Cys Ser Leu Lys Glu Arg Arg Phe Pro Gly Asn Arg Thr Lys
    850                 855                 860

Leu Glu Lys Glu Thr Glu Leu Leu Ala Glu Leu Glu Glu Leu Met Glu
865                 870                 875                 880
```

-continued

```
Leu Val Arg Phe Thr Met Pro Ser Ile Pro Glu Ile Ser Ala Lys Ala
                885                 890                 895

Glu Ser Gly Tyr Asp Thr Met Ile Lys Lys Tyr Phe Lys Asp Phe Ile
            900                 905                 910

Glu Lys Lys Val Phe Lys Asn Pro Lys Thr Ser Asn Leu Tyr Tyr His
        915                 920                 925

Ser Asp Ser Lys Thr Pro Val Thr Arg Lys Tyr Met Ala Leu Leu Met
    930                 935                 940

Arg Ser Ala Pro Leu His Leu Tyr Lys Asp Ile Phe Lys Gly Tyr Tyr
945                 950                 955                 960

Leu Ile Thr Lys Lys Glu Cys Leu Glu Tyr Ile Lys Leu Ser Asn Ile
                965                 970                 975

Ile Lys Asp Tyr Gln Asn Ser Leu Asn Glu Leu His Glu Gln Leu Glu
            980                 985                 990

Arg Ile Lys Leu Lys Ser Glu Lys  Gln Asn Gly Lys Asp  Ser Leu Tyr
        995                 1000                1005

Leu Asp  Lys Lys Asp Phe Tyr  Lys Val Lys Glu Tyr  Val Glu Asn
    1010                1015                1020

Leu Glu  Gln Val Ala Arg Tyr  Lys His Leu Gln His  Lys Ile Asn
    1025                1030                1035

Phe Glu  Ser Leu Tyr Arg Ile  Phe Arg Ile His Val  Asp Ile Ala
    1040                1045                1050

Ala Arg  Met Val Gly Tyr Thr  Gln Asp Trp Glu Arg  Asp Met His
    1055                1060                1065

Phe Leu  Phe Lys Ala Leu Val  Tyr Asn Gly Val Leu  Glu Glu Arg
    1070                1075                1080

Arg Phe  Glu Ala Ile Phe Asn  Asn Asn Asp Asp Asn  Asn Asp Gly
    1085                1090                1095

Arg Ile  Val Lys Lys Ile Gln  Asn Asn Leu Asn Asn  Lys Asn Arg
    1100                1105                1110

Glu Leu  Val Ser Met Leu Cys  Trp Asn Lys Lys Leu  Asn Lys Asn
    1115                1120                1125

Glu Phe  Gly Ala Ile Ile Trp  Lys Arg Asn Pro Ile  Ala His Leu
    1130                1135                1140

Asn His  Phe Thr Gln Thr Glu  Gln Asn Ser Lys Ser  Ser Leu Glu
    1145                1150                1155

Ser Leu  Ile Asn Ser Leu Arg  Ile Leu Leu Ala Tyr  Asp Arg Lys
    1160                1165                1170

Arg Gln  Asn Ala Val Thr Lys  Thr Ile Asn Asp Leu  Leu Leu Asn
    1175                1180                1185

Asp Tyr  His Ile Arg Ile Lys  Trp Glu Gly Arg Val  Asp Glu Gly
    1190                1195                1200

Gln Ile  Tyr Phe Asn Ile Lys  Glu Lys Glu Asp Ile  Glu Asn Glu
    1205                1210                1215

Pro Ile  Ile His Leu Lys His  Leu His Lys Lys Asp  Cys Tyr Ile
    1220                1225                1230

Tyr Lys  Asn Ser Tyr Met Phe  Asp Lys Gln Lys Glu  Trp Ile Cys
    1235                1240                1245

Asn Gly  Ile Lys Glu Glu Val  Tyr Asp Lys Ser Ile  Leu Lys Cys
    1250                1255                1260

Ile Gly  Asn Leu Phe Lys Phe  Asp Tyr Glu Asp Lys  Asn Lys Ser
    1265                1270                1275

Ser Ala  Asn Pro Lys His Thr
```

-continued 1280 1285

<210> SEQ ID NO 20
<211> LENGTH: 2677
<212> TYPE: DNA
<213> ORGANISM: Artificial sequence
<220> FEATURE:
<223> OTHER INFORMATION: BFP-mEGFP construct

<400> SEQUENCE: 20

```
ggctccggtg cccgtcagtg ggcagagcgc acatcgccca cagtccccga gaagttgggg     60
ggaggggtcg gcaattgaac cggtgcctag agaaggtggc gcggggtaaa ctgggaaagt    120
gatgtcgtgt actggctccg cctttttccc gagggtgggg gagaaccgta tataagtgca    180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccacct ggctgcagta cgtgattctt gatcccgagc ttcgggttgg aagtgggtgg    360
gagagttcga ggccttgcgc ttaaggagcc ccttcgcctc gtgcttgagt tgaggcctgg    420
cctgggcgct ggggccgccg cgtgcgaatc tggtggcacc ttcgcgcctg tctcgctgct    480
ttcgataagt ctctagccat ttaaaatttt tgatgacctg ctgcgacgct ttttttctgg    540
caagatagtc ttgtaaatgc gggccaagat ctgcacactg gtatttcggt ttttggggcc    600
gcgggcggcg acggggcccg tgcgtcccag cgcacatgtt cggcgaggcg gggcctgcga    660
gcgcggccac cgagaatcgg acgggggtag tctcaagctg gccggcctgc tctggtgcct    720
ggcctcgcgc cgccgtgtat cgccccgccc tgggcggcaa ggctggcccg gtcggcacca    780
gttgcgtgag cggaaagatg gccgcttccc ggccctgctg cagggagctc aaaatggagg    840
acgcggcgct cgggagagcg ggcgggtgag tcacccacac aaaggaaaag ggcctttccg    900
tcctcagccg tcgcttcatg tgactccacg gagtaccggg cgccgtccag gcacctcgat    960
tagttctcga gcttttggag tacgtcgtct ttaggttggg gggaggggtt ttatgcgatg   1020
gagtttcccc acactgagtg ggtggagact gaagttaggc cagcttggca cttgatgtaa   1080
ttctccttgg aatttgccct ttttgagttt ggatcttggt tcattctcaa gcctcagaca   1140
gtggttcaaa gtttttttct tccatttcag gtgtcgtgag gaattagctt ggtactaata   1200
cgactcacta tagggagacc caagctggct aggtaagctt ggtaccgagc tcggatccgg   1260
taccgccacc atggtgagca agggcgagga gctgttcacc ggggtggtgc ccatcctggt   1320
cgagctggac ggcgacgtaa acggccacaa gttcagcgtg tccggcgagg gcgagggcga   1380
tgccacctac ggcaagctga ccctgaagtt catctgcacc accggcaagc tgccggtgcc   1440
ctggcccacc ctcgtgacca ccctgaccca tggcgtgcag tgcttcagcc gctaccccga   1500
ccacatgaag cagcacgact tcttcaagtc cgccatgccc gaaggctacg tccaggagcg   1560
caccatcttc ttcaaggacg acggcaacta caagacccgc gccgaggtga agttcgaggg   1620
cgacaccctg gtgaaccgca tcgagctgaa gggcatcgac ttcaaggagg acggcaacat   1680
cctggggcac aagctggagt acaactacaa cagccacaac gtctatatca tggccgacaa   1740
gcagaagaac ggcatcaagg tgaacttcaa gatccgccac aacatcgagg acggcagcgt   1800
gcagctcgcc gaccactacc agcagaacac ccccatcggc gacggccccg tgctgctgcc   1860
cgacaaccac tacctgagca cccagtccaa gctgagcaaa gaccccaacg agaagcgcga   1920
tcacatggtc ctgctggagt tcgtgaccgc cgccgggatc actctcggca tggacgagct   1980
gtacaagtaa ctcgagatat ctagacccag ctttcttgta caaagtggtt gatatccagc   2040
```

acagtggcgg ccgctcgaca atcaacctct ggattacaaa atttgtgaaa gattgactgg 2100
tattcttaac tatgttgctc cttttacgct atgtggatac gctgctttaa tgcctttgta 2160
tcatgctatt gcttcccgta tggctttcat tttctcctcc ttgtataaat cctggttgct 2220
gtctctttat gaggagttgt ggcccgttgt caggcaacgt ggcgtggtgt gcactgtgtt 2280
tgctgacgca acccccactg gttggggcat tgccaccacc tgtcagctcc tttccgggac 2340
tttcgctttc cccctcccta ttgccacggc ggaactcatc gccgcctgcc ttgcccgctg 2400
ctggacaggg gctcggctgt tgggcactga caattccgtg gtgttgtcgg ggaagctgac 2460
gtcctttcca tggctgctcg cctgtgttgc cacctggatt ctgcgcggga cgtccttctg 2520
ctacgtccct tcggccctca atccagcgga ccttccttcc cgcggcctgc tgccggctct 2580
gcggcctctt ccgcgtcttc gccttcgccc tcagacgagt cggatctccc tttgggccgc 2640
ctccccgcct ggacctgcag gattctgcag atatccg 2677

<210> SEQ ID NO 21
<211> LENGTH: 5318
<212> TYPE: DNA
<213> ORGANISM: Artificial sequence
<220> FEATURE:
<223> OTHER INFORMATION: dCas9-3xFlag-NLS

<400> SEQUENCE: 21
ttaatgacgg ctcgtttctt ttctgtggct gcgtgaaagc cttaaagggc tccgggaggg 60
ccctttgtgc gggggggagc ggctcggggg gtgcgtgcgt gtgtgtgtgc gtggggagcg 120
ccgcgtgcgg cccgcgctgc ccggcggctg tgagcgctgc gggcgcggcg cggggctttg 180
tgcgctccgc gtgtgcgcga ggggagcgcg gccgggggcg gtgccccgcg gtgcgggggg 240
gctgcgaggg gaacaaaggc tgcgtgcggg gtgtgtgcgt gggggggtga gcagggggtg 300
tgggcgcggc ggtcgggctg taaccccccc ctgcaccccc ctccccgagt tgctgagcac 360
ggcccggctt cgggtgcggg gctccgtgcg gggcgtggcg cggggctcgc cgtgccgggc 420
ggggggtggc ggcaggtggg ggtgccgggc ggggcggggc cgcctcgggc cggggagggc 480
tcgggggagg ggcgcggcgg ccccggagcg ccggcggctg tcgaggcgcg gcgagccgca 540
gccattgcct tttatggtaa tcgtgcgaga gggcgcaggg acttcctttg tcccaaatct 600
ggcggagccg aaatctggga ggcgccgccg caccccctct agcgggcgcg ggcgaagcgg 660
tgcggcgccg gcaggaagga aatgggcggg gagggccttc gtgcgtcgcc gcgccgccgt 720
ccccttctcc atctccagcc tcggggctgc cgcaggggga cggctgcctt cggggggac 780 ggggcagggc ggggttcggc ttctggcgtg tgaccggcgg ctctagagcc tctgctaacc 840
atgttcatgc cttcttcttt ttcctacagc tcctgggcaa cgtgctggtt gttgtgctgt 900
ctcatcattt tggcaaagaa ttcgccacca tggacaagaa gtacagcatc ggcctggcca 960
tcggcaccaa ctctgtgggc tgggccgtga tcaccgacga gtacaaggtg cccagcaaga 1020
aattcaaggt gctgggcaac accgaccggc acagcatcaa gaagaacctg atcggcgccc 1080
tgctgttcga cagcggagaa acagccgagg ccacccggct gaagagaacc gccagaagaa 1140
gatacaccag acggaagaac cggatctgct atctgcaaga gatcttcagc aacgagatgg 1200
ccaaggtgga cgacagcttc ttccacagac tggaagagtc cttcctggtg gaagaggata 1260
agaagcacga gcggcacccc atcttcggca acatcgtgga cgaggtggcc taccacgaga 1320
agtaccccac catctaccac ctgagaaaga aactggtgga cagcaccgac aaggccgacc 1380

-continued tgcggctgat ctatctggcc ctggcccaca tgatcaagtt ccggggccac ttcctgatcg 1440
agggcgacct gaaccccgac aacagcgacg tggacaagct gttcatccag ctggtgcaga 1500
cctacaacca gctgttcgag gaaaacccca tcaacgccag cggcgtggac gccaaggcca 1560
tcctgtctgc cagactgagc aagagcagac ggctggaaaa tctgatcgcc cagctgcccg 1620
gcgagaagaa gaatggcctg ttcggcaacc tgattgccct gagcctgggc ctgaccccca 1680
acttcaagag caacttcgac ctggccgagg atgccaaact gcagctgagc aaggacacct 1740
acgacgacga cctggacaac ctgctggccc agatcggcga ccagtacgcc gacctgtttc 1800
tggccgccaa gaacctgtcc gacgccatcc tgctgagcga catcctgaga gtgaacaccg 1860
agatcaccaa ggcccccctg agcgcctcta tgatcaagag atacgacgag caccaccagg 1920
acctgaccct gctgaaagct ctcgtgcggc agcagctgcc tgagaagtac aaagagattt 1980
tcttcgacca gagcaagaac ggctacgccg gctacatcga tggcggagcc agccaggaag 2040
agttctacaa gttcatcaag cccatcctgg aaaagatgga cggcaccgag gaactgctcg 2100
tgaagctgaa cagagaggac ctgctgcgga agcagcggac cttcgacaac ggcagcatcc 2160
cccaccagat ccacctggga gagctgcacg ccattctgcg gcggcaggaa gatttttacc 2220
cattcctgaa ggacaaccgg gaaaagatcg agaagatcct gaccttccgc atcccctact 2280
acgtgggccc tctggccagg ggaaacagca gattcgcctg gatgaccaga aagagcgagg 2340
aaaccatcac cccctggaac ttcgaggaag tggtggacaa gggcgccagc gcccagagct 2400
tcatcgagcg gatgaccaac ttcgataaga acctgcccaa cgagaaggtg ctgcccaagc 2460
acagcctgct gtacgagtac ttcaccgtgt acaacgagct gaccaaagtg aaatacgtga 2520
ccgagggaat gagaaagccc gccttcctga gcggcgagca gaaaaaagcc atcgtggacc 2580
tgctgttcaa gaccaaccgg aaagtgaccg tgaagcagct gaaagaggac tacttcaaga 2640
aaatcgagtg cttcgactcc gtggaaatct ccggcgtgga agatcggttc aacgcctccc 2700
tgggcacata ccacgatctg ctgaaaatta tcaaggacaa ggacttcctg gacaatgagg 2760
aaaacgagga cattctggaa gatatcgtgc tgaccctgac actgtttgag gacagagaga 2820
tgatcgagga acggctgaaa acctatgccc acctgttcga cgacaaagtg atgaagcagc 2880
tgaagcggcg gagatacacc ggctggggca ggctgagccg gaagctgatc aacggcatcc 2940
gggacaagca gtccggcaag acaatcctgg atttcctgaa gtccgacggc ttcgccaaca 3000
gaaacttcat gcagctgatc cacgacgaca gcctgacctt taaagaggac atccagaaag 3060
cccaggtgtc cggccagggc gatagcctgc acgagcacat tgccaatctg gccggcagcc 3120
ccgccattaa gaagggcatc ctgcagacag tgaaggtggt ggacgagctc gtgaaagtga 3180
tgggccggca caagcccgag aacatcgtga tcgaaatggc cagagagaac cagaccaccc 3240
agaagggaca gaagaacagc cgcgagagaa tgaagcggat cgaagagggc atcaaagagc 3300
tgggcagcca gatcctgaaa gaacaccccg tggaaaacac ccagctgcag aacgagaagc 3360
tgtacctgta ctacctgcag aatgggcggg atatgtacgt ggaccaggaa ctggacatca 3420
accggctgtc cgactacgat gtggacgcta tcgtgcctca gagctttctg aaggacgact 3480
ccatcgataa caaagtgctg actcggagcg acaagaaccg gggcaagagc gacaacgtgc 3540
cctccgaaga ggtcgtgaag aagatgaaga actactggcg ccagctgctg aatgccaagc 3600
tgattaccca gaggaagttc gacaatctga ccaaggccga gagaggcggc ctgagcgaac 3660
tggataaggc cggcttcatc aagagacagc tggtggaaac ccggcagatc acaaagcacg 3720
tggcacagat cctggactcc cggatgaaca ctaagtacga cgagaacgac aaactgatcc 3780

-continued gggaagtgaa agtgatcacc ctgaagtcca agctggtgtc cgatttccgg aaggatttcc 3840
agttttacaa agtgcgcgag atcaacaact accaccacgc ccacgacgcc tacctgaacg 3900
ccgtcgtggg aaccgccctg atcaaaaagt accctaagct ggaaagcgag ttcgtgtacg 3960
gcgactacaa ggtgtacgac gtgcggaaga tgatcgccaa gagcgagcag gaaatcggca 4020
aggctaccgc caagtacttc ttctacagca acatcatgaa ctttttcaag accgagatta 4080
ccctggccaa cggcgagatc cggaagcggc ctctgatcga gacaaacggc gaaacaggcg 4140
agatcgtgtg ggataagggc cgggactttg ccaccgtgcg gaaagtgctg tctatgcccc 4200
aagtgaatat cgtgaaaaag accgaggtgc agacaggcgg cttcagcaaa gagtctatcc 4260
tgcccaagag gaacagcgac aagctgatcg ccagaaagaa ggactgggac cctaagaagt 4320
acggcggctt cgacagcccc accgtggcct attctgtgct ggtggtggcc aaagtggaaa 4380
agggcaagtc caagaaactg aagagtgtga aagagctgct ggggatcacc atcatggaaa 4440
gaagcagctt cgagaagaat cccatcgact ttctggaagc caagggctac aaagaagtga 4500
aaaaggacct gatcatcaag ctgcctaagt actccctgtt cgagctggaa aacggccgga 4560
agagaatgct ggcctctgcc ggcgaactgc agaagggaaa cgaactggcc ctgccctcca 4620
aatatgtgaa cttcctgtac ctggccagcc actatgagaa gctgaagggc tcccccgagg 4680
ataatgagca gaaacagctg tttgtggaac agcacaaaca ctacctggac gagatcatcg 4740
agcagatcag cgagttctcc aagagagtga tcctggccga cgctaatctg gacaaggtgc 4800
tgagcgccta caacaagcac agagacaagc ctatcagaga gcaggccgag aatatcatcc 4860
acctgtttac cctgaccaat ctgggagccc ctgccgcctt caagtacttt gacaccacca 4920
tcgaccggaa gaggtacacc agcaccaaag aggtgctgga cgccaccctg atccaccaga 4980
gcatcaccgg cctgtacgag acacggatcg acctgtctca gctgggaggc gacgccgact 5040
ataaggacca cgacggagac tacaaggatc atgatattga ttacaaagac gatgacgata 5100
agagcctggg cagcggctcc cccaagaaaa aacgcaaggt ggaagatcct aagaaaaagc 5160
ggaaagtgtg ataagctagc agatcttttt ccctctgcca aaaattatgg ggacatcatg 5220
aagccccttg agcatctgac ttctggctaa taaaggaaat ttattttcat tgcaatagtg 5280
tgttggaatt ttttgtgtct ctcactcgga aggacata 5318

<210> SEQ ID NO 22
<211> LENGTH: 50
<212> TYPE: DNA
<213> ORGANISM: Artificial sequence
<220> FEATURE:
<223> OTHER INFORMATION: Homology arm for insertion at position: chr9:107,422,356 / hg38

<400> SEQUENCE: 22
gcttctccag ccctggcctg ggtcaatcct tggggcccag actgagcacg 50

<210> SEQ ID NO 23
<211> LENGTH: 400
<212> TYPE: DNA
<213> ORGANISM: Artificial sequence
<220> FEATURE:
<223> OTHER INFORMATION: Homology arm for insertion at position: chr9:107,422,356 / hg38

<400> SEQUENCE: 23
gttttatcag ttttggagga tgtacataaa tatatagaat gagagtctca aaactaatct 60
tgtagctacg cctgtgatgg gctaattgat gaatcagtgc tggagaatgg gtcacagtgg 120
caaatgaggc tggagaggcc cgtgagctgc tgtcccagag ggcctgggat gtcctgcagg 180
gagcttggca tgagaaacct tggagagttt taagcaaggg ctgatgtggg ctgcctagaa 240
aggcatggat gagagaagcc tggagacagg gatcccaggg aaacgcccat gcaattagtc 300
tatttctgct gcaagtaagc atgcatttgt aggcttgatg ctttttttct gcttctccag 360
ccctggcctg ggtcaatcct tggggcccag actgagcacg 400

<210> SEQ ID NO 24
<211> LENGTH: 50
<212> TYPE: DNA
<213> ORGANISM: Artificial sequence
<220> FEATURE:
<223> OTHER INFORMATION: Homology arm for insertion at position: chr9:107,422,356 / hg38

<400> SEQUENCE: 24
tgatggcaga ggaaaggaag ccctgcttcc tccagagggc gtcgcaggac 50

<210> SEQ ID NO 25
<211> LENGTH: 400
<212> TYPE: DNA
<213> ORGANISM: Artificial sequence
<220> FEATURE:
<223> OTHER INFORMATION: Homology arm for insertion at position: chr9:107,422,356 / hg38

<400> SEQUENCE: 25
tgatggcaga ggaaaggaag ccctgcttcc tccagagggc gtcgcaggac agcttttcct 60
agacaggggc tagtatgtgc agctcctgca ccgggatact ggttgacaag tttggctggg 120
ctggaagcca gcacctaggg aggtccctgg aaggggccag cctcaccagg agaggaggga 180
cctggccctt cagggtcgag ctcaacagag gaaaagatct cagggcaccc agagcccagt 240
ggctttcagc acctgcatga aaatcagaga tcaaccagat taccccatat tgcccaagag 300
aaaactgagg ccagaaagtg atggagcttg cccaggaccc cagagggtgt tagaggcagg 360
ccagaaccag aggacagctc tgtcccagca cttgccctcc 400

<210> SEQ ID NO 26
<211> LENGTH: 51
<212> TYPE: DNA
<213> ORGANISM: Artificial sequence
<220> FEATURE:
<223> OTHER INFORMATION: Homology arm for insertion at position: chr1:179,826,688/ hg38

<400> SEQUENCE: 26
caccctcctc cacccaccca aatcctacct gtccttcaaa ccttgtccag g 51

<210> SEQ ID NO 27
<211> LENGTH: 401
<212> TYPE: DNA
<213> ORGANISM: Artificial sequence
<220> FEATURE:
<223> OTHER INFORMATION: Homology arm for insertion at position: chr1:179,826,688/ hg38

<400> SEQUENCE: 27
tcactggggt agaccccaca gccttctctc caggccttgc tgcactgggc catctcctcg 60
tggtcccagg atgtcccagc aagcggagca ctgaccacag gagtaggggt gagggaacaa 120
accaggcata cactcctggc atcgccagac cttggccctg aaccccaccc aaacggatcc 180

-continued

```
atttaaatga tcctgaggtc taggaacccg ctgggattcg acagaaatgt gagcccatca    240

ggtattcaaa aagggtctgt gccagtcccc caaatagttt aaaaacaaca acactagaaa    300

ttttctctat ccacctggaa tgagttttcg gttacaattc tgaccccatg caccctcctc    360

cacccaccca aatcctacct gtccttcaaa ccttgtccag g                        401


<210> SEQ ID NO 28
<211> LENGTH: 50
<212> TYPE: DNA
<213> ORGANISM: Artificial sequence
<220> FEATURE:
<223> OTHER INFORMATION: Homology arm for insertion at position:
      chr1:179,826,688/ hg38

<400> SEQUENCE: 28

attctatgat ttattcccct gaggcccctg gaagcaatca ctccctttc                 50


<210> SEQ ID NO 29
<211> LENGTH: 400
<212> TYPE: DNA
<213> ORGANISM: Artificial sequence
<220> FEATURE:
<223> OTHER INFORMATION: Homology arm for insertion at position:
      chr1:179,826,688/ hg38

<400> SEQUENCE: 29

attctatgat ttattcccct gaggcccctg gaagcaatca ctcccttttc tggataagca     60

aaacatcctc tctccacctc cccgcgtgtt gctggattgc tggtatctgg catgccctat    120

attttccctt gcggacaggt tgttccttga ggctggattc cccactgcac tggccccagc    180

acccaacaca ggccttgcac acgctttaca gccagccaaa gccagctgaa ggaaccagat    240

gcactcctgt ctttcatagg ctggagggtt tttttttttc ttttcaatgt ctttcactgt    300

ggtaaaatac acatataaag cttatcacct tcaccattaa gtgggcagca gttcagtggt    360

atcaagcaca ttcataatgt gtgaccgtca ccaccatcca                          400
```